United States Patent
Labelle et al.

(10) Patent No.: US 10,221,139 B2
(45) Date of Patent: Mar. 5, 2019

(54) INHIBITORS OF HISTONE DEMETHYLASES

(71) Applicant: Gilead Sciences, Inc., Foster City, CA (US)

(72) Inventors: Marc Labelle, Basking Ridge, NJ (US); Thomas Boesen, Copenhagen (DK); Mukund Mehrotra, Winnipeg (CA); Qasim Khan, Winnipeg (CA); Farman Ullah, Winnipeg (CA)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/436,055

(22) Filed: Feb. 17, 2017

(65) Prior Publication Data

US 2017/0320827 A1 Nov. 9, 2017

Related U.S. Application Data

(63) Continuation of application No. 14/472,059, filed on Aug. 28, 2014, which is a continuation of application No. 14/381,558, filed as application No. PCT/EP2013/070457 on Oct. 1, 2013, now abandoned.

(60) Provisional application No. 61/770,050, filed on Feb. 27, 2013, provisional application No. 61/708,806, filed on Oct. 2, 2012.

(30) Foreign Application Priority Data

Oct. 2, 2012 (DK) .................... 2012 00599
Feb. 27, 2013 (DK) .................... 2013 70112

(51) Int. Cl.
| | |
|---|---|
| *A61K 31/44* | (2006.01) |
| *C07D 213/79* | (2006.01) |
| *C07D 401/12* | (2006.01) |
| *C07D 405/12* | (2006.01) |
| *C07D 413/12* | (2006.01) |
| *A61K 31/443* | (2006.01) |
| *A61K 31/4439* | (2006.01) |
| *A61K 31/4545* | (2006.01) |
| *A61K 31/496* | (2006.01) |
| *C07D 401/06* | (2006.01) |
| *A61K 31/444* | (2006.01) |

(52) U.S. Cl.
CPC ............ *C07D 213/79* (2013.01); *A61K 31/44* (2013.01); *A61K 31/443* (2013.01); *A61K 31/444* (2013.01); *A61K 31/4439* (2013.01); *A61K 31/4545* (2013.01); *A61K 31/496* (2013.01); *C07D 401/06* (2013.01); *C07D 401/12* (2013.01); *C07D 405/12* (2013.01); *C07D 413/12* (2013.01)

(58) Field of Classification Search
None
See application file for complete search history.

(56) References Cited

U.S. PATENT DOCUMENTS

| | | |
|---|---|---|
| 4,100,274 A | 7/1978 | Dutta et al. |
| 4,636,505 A | 1/1987 | Tucker |
| 4,659,516 A | 4/1987 | Bowler et al. |
| 4,866,076 A | 9/1989 | Gribble |
| 5,010,099 A | 4/1991 | Gunasekera et al. |
| 5,843,901 A | 12/1998 | Roeske |
| 5,874,438 A | 2/1999 | Schohe-Loop et al. |
| 6,194,181 B1 | 2/2001 | Hofmann et al. |
| 6,620,811 B2 | 9/2003 | Flohr et al. |
| 7,696,210 B2 | 4/2010 | Garrick et al. |
| 9,062,032 B2 | 6/2015 | Miura et al. |
| 9,221,801 B2 | 12/2015 | Labelle et al. |
| 9,650,339 B2 | 5/2017 | Labelle et al. |
| 2008/0177082 A1 | 7/2008 | Wallace et al. |
| 2009/0246274 A1 | 10/2009 | Bateman et al. |
| 2011/0224190 A1 | 9/2011 | Huang et al. |

(Continued)

FOREIGN PATENT DOCUMENTS

| | | | |
|---|---|---|---|
| CN | 102585150 | * | 7/2012 |
| EP | 2578569 A1 | | 4/2013 |

(Continued)

OTHER PUBLICATIONS

P. Ettmayer et al. J. Med. Chem. (2004) 47(10), pp. 2393-2404.*
Testa, B. et al. Lessons Learned from Marketed and Investigational Prodrugs. J. Med. Chem. 2004, vol. 47(10), p. 2393.*
Kocienski, PJ. et al. Protecting Groups. Thieme. 2005, p. 395.*
H.-K. Han. AAPS Pharmsci. (2000) 2(1), article 6, pp. 1-11.*
Hatch et al. "Assessing histone demethylase inhibitors in cells: lessons learned." Epigenetics & Chromatin, 2017, vol. 10, No. 9, pp. 1-17. (Year: 2017).*
Hardman et al., "Goodman & Gilnnan's The Pharmacological Basis of Therapeutics," 9th ed., 1996, pp. 51 and 57-58 (Year: 1996).*
Chang, et al., (2011), "Inhibition of Histone Demethylases by 4-Carboxy-2.2'-Bipyridyl Compounds", ChemMedChem, 6:759-64.

(Continued)

*Primary Examiner* — Shengjun Wang
(74) *Attorney, Agent, or Firm* — Joel Silver; Donna Gressler

(57) ABSTRACT

The present application discloses compounds capable of modulating the activity of histone demethylases (HDMEs), which are useful for prevention and/or treatment of diseases in which genomic dysregulation is involved in the pathogenesis, such as e.g. cancer. The present application also discloses pharmaceutical compositions comprising said compounds and the use of such compounds as a medicament. The compounds take the form

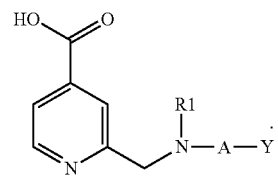

13 Claims, No Drawings

(56) References Cited

U.S. PATENT DOCUMENTS

| | | |
|---|---|---|
| 2012/0282179 A1 | 11/2012 | Aftab et al. |
| 2014/0171432 A1 | 6/2014 | Kanouni et al. |
| 2014/0371195 A1 | 12/2014 | Labelle et al. |
| 2014/0371214 A1 | 12/2014 | Labelle et al. |
| 2015/0065522 A1 | 3/2015 | Albrecht et al. |
| 2015/0203453 A1 | 7/2015 | Labelle et al. |
| 2017/0320827 A1 | 11/2017 | Labelle et al. |

FOREIGN PATENT DOCUMENTS

| | | |
|---|---|---|
| WO | WO-1998/08849 A1 | 3/1998 |
| WO | WO-1998/10121 A1 | 3/1998 |
| WO | WO-1998/22461 A1 | 5/1998 |
| WO | WO-1998/25929 A1 | 6/1998 |
| WO | WO-1999/17804 A1 | 4/1999 |
| WO | WO-1999/43653 A1 | 9/1999 |
| WO | WO-2000/31247 A2 | 6/2000 |
| WO | WO-2002/22577 A2 | 3/2002 |
| WO | WO-2008/002671 A2 | 1/2008 |
| WO | WO-2009/119088 A1 | 10/2009 |
| WO | WO-2010/056549 A1 | 5/2010 |
| WO | WO-2011/017583 A1 | 2/2011 |
| WO | WO-2011/148888 A1 | 12/2011 |
| WO | WO-2012/007007 A | 1/2012 |
| WO | WO-2012/042042 A1 | 4/2012 |
| WO | WO-2012/047156 A1 | 4/2012 |
| WO | WO-2012/071469 A2 | 5/2012 |
| WO | WO-2012/135113 A2 | 10/2012 |
| WO | WO-2013/025805 A1 | 2/2013 |
| WO | WO-2013/081091 A1 | 6/2013 |
| WO | WO-2013/123411 A1 | 8/2013 |
| WO | WO-2013/129435 A1 | 9/2013 |
| WO | WO-2014/053491 A1 | 4/2014 |
| WO | WO-2014/089364 A1 | 6/2014 |
| WO | WO-2014/100818 A1 | 6/2014 |
| WO | WO-2014/131777 A1 | 9/2014 |
| WO | WO-2014/151106 A1 | 9/2014 |
| WO | WO-2015/153498 A1 | 10/2015 |

OTHER PUBLICATIONS

Cloos, et al., (2008), "Erasing the Methyl Mark: Histone Demethylases at the Center of Cellula Differentiation and Disease", Genes & Dev., 22:1115-40.

Database Registry [Online] Retrieved from STN, date of publication: Sep. 13, 2010, retrieved on: Jul. 12, 2017, CAS Registry No. 1240620-13-6.

Database Registry [Online] Retrieved from STN, date of publication: on or before Jun. 13, 2006, retrieved on: Jul. 12, 2017, CAS Registry No. 1027829-00-0, 1027376-83-5, 1026865-28-0, 1026799-49-4, 1026039-97-3, 1025883-36-6.

European Search Report issued for EP16186022.6 dated Feb. 9, 2017, 9pgs.

International Search Report and Written Opinion issued by the International Searching Authority for PCT/EP2013/070457, dated Jan. 14, 2014.

International Search Report and Written Opinion issued by the International Searching; Authority for Application No. PCT/US2015/046921, dated Nov. 2, 2015, 13 pages.

International Search Report and Written Opinion issued by the International Searching Authority for PCT/EP2014/053674, dated Mar. 31, 2014, 4 pages.

International Search Report and Written Opinion issued by the International Searching Authority for PCT/US2015/023407, dated Jul. 31, 2015, 4 pages.

Kojima, et al., (2007), "Synthesis and Characterization of Mononuclear Ruthenium(III) Pyridylamine Complexes and Mechanistic Insights into Their Catalytic Alkane Functionalization with m-Chloroperbenzoic Acid", Chemistry European Journal, 13:8212-22.

Lohse, et al., (2011), "Inhibitors of Histone Demethylases", Bioorganic & Medicinal Chemistry, 19:3625-36.

Morton, et al., (2007), "Establishment of Human Tumor Xenografts in Immunodeficient Mice", Nature Protocols, 2:247-50.

Queguiner, et al., (1969), "Reduction Selective des Pyridinedicarboxylates d'Ethyle; Dissymetriques", Comptes Rendus des Seances de l'Academie des Sciences, Serie C: Sciences Chimiques, 268:182-5, (with English translation).

Rehse, et al., (1988), "Antiaggregatorische uno Anticoagulante; Eigenschaften Von Oligoaminen. 8. MITT.: Oligoamine MIT Nheterocyclischen; Teilstrukturen", Arch Pharm. (Weinheim), 321:533-6, (with English translation).

Roy, et al., (2011), "AiphaLISA JMJD2A Histone H3-Lysine 9 Demethylase Assay", PerkinEime Technical Note: AlphaLISA #12, Apr. 2 pages.

Seydel, J., et al., (1976), "Mode of action and quantitative structure-activity correlations of tuberculostatic drugs of the isonicotinic acid hydrazide type", *J Med Chem*, 19:483-92.

Testa, (2004), "Prodrug research: futile or fertile?", Biochem Pharmacol, 68:2097-106.

\* cited by examiner

INHIBITORS OF HISTONE DEMETHYLASES

CROSS REFERENCE TO RELATED APPLICATIONS

The present application is a Continuation of U.S. application Ser. No. 14/472,059, filed Aug. 28, 2014, which is a Continuation of U.S. application Ser. No. 14/381,558, filed on Aug. 27, 2014, which is a National Stage Entry of PCT/EP2013/070457, filed Oct. 1, 2013, which claims priority from U.S. Provisional App. No. 61/770,050, filed Feb. 27, 2013 and from U.S. Provisional App. No. 61/708,806, filed Oct. 2, 2012, the disclosures of which are herein incorporated by reference in their entirety.

FIELD OF THE INVENTION

The present invention relates to compounds capable of modulating the activity of histone demethylases (HDMEs), which compounds are useful for the prevention and/or the treatment of diseases in which genomic dysregulation is involved in the pathogenesis, such as e.g. cancer.

BACKGROUND OF THE INVENTION

The DNA of eukaryotic cells is packaged into chromatin by winding of the DNA around histone proteins to form nucleosomes, the basic unit of chromatin. One of the important functions of chromatin is to determine regions of active and silenced transcription by changing the ordered chromatin structure. Such changes have profound effects on cellular function since they affect fundamental processes as differentiation, proliferation and apoptosis, and are often referred collectively to as "epigenetic" since they can lead to heritable changes that do not involve changes in gene sequences (Quina, A. S. et al. (2006), Biochem. Pharmacol. 72; 1563-1569)

These highly controlled chromatin changes are mediated by alterations histone proteins associated with DNA in the nucleosome. Most notably, the N-terminal histone tail of Histone H3 and histone H4 are subject to such covalent changes, which include changes in methylation, acetylation, phosphorylation and ubiquitination. The addition or removal of these groups on histones is mediated by specific enzymes, e.g. histone methyl transferases and histone demethylases for methyl groups, histone acetyltransferases and histone deacetylases for acetyl groups, etc. In the event that the activity or expression of these "epigenetic" enzymes is not correctly controlled and regulated it may lead to disease. Cancer, in particular, is an area of high importance in relation to dysregulated epigenetic enzyme activity due to the role of epigenetics in cell differentiation, proliferation and apoptosis, but epigenetics may also play a role in other diseases like metabolic, inflammatory, neurodegenerative and cardiovascular diseases. Therefore the selective modulation of aberrant action of epigenetic enzymes may hold great promise for the treatment of human disease (Kelly, T. K. et al. (2010), Nat. Biotechnol. 28; 1069-1078, and Cloos, P. a. C. et al. (2008), Genes. Dev. 22; 115-1140).

Methylation and demethylation of lysine residues on the histone H3 tail constitute important epigenetic marks delineating transcriptionally active and inactive chromatin. For example, methylation of lysine 9 on histone H3 (H3K9) is usually associated with epigenetically silenced chromatin (Fischle, W., et. al. (2003), Curr. Opinion Cell Biol. 15, 172-83; Margueron, R., et al. (2005), Curr. Opinion Genet. Dev. 15, 163-76) while methylation of lysine 4 on histone 3 is associated with transcriptionally active chromatin. Similarly, the lysine 27 histone H3 (H3K27) mark is repressive in its di- and tri-methylated states whereas the lysine 36 histone H3 mark is found in association with gene activation (Barski, A. et al. (2007), Cell, 129, 823-37; Vakoc, C. et al. (2006) Mol. Cell. Biol. 26, 9185-95; Wagner, E. J. & Carpenter, P. B. (2012) Nature Mol. Cell Biol 13, 115-26). There are, however, many exemptions from these general rules of association between methylation states of epigenetic marks and the effect they have on transcription.

As documented by studies of the SUV39H1 knockout mouse, loss of the tri-methyl variant of the H3K9 mark results in chromosomal aberrations and predisposes to cancer (Peters, A. H. et al., Cell 107, 323-37, 2001). The JMJD2C protein (KDM4C, GASC1) has been identified as an eraser of the H3K9 mark (a histone demethylase) and may therefore promote cancer if its expression and activity is not tightly controlled (Cloos, P. et al. (2006), Nature 442, 307-11; Klose, R. J. et al. (2006), Nature 442, 312-16; Liu, G. et al. (2009), Oncogene 28, 4491-500). For example, JMJD2C has been shown to induce transformed phenotypes like growth factor independent growth, anchorage independent growth and mammosphere formation, if it is overexpressed in cells (Liu, G. et al. (2009), Oncogene 28, 4491-500). These findings are supported by the overexpression of JMJD2C in a range of human tumours like squamous cell carcinoma, metastatic lung carcinoma, prostate cancer, breast cancer and several others (Yang, Z. Q. et al. (2000) Cancer Res. 60, 4735-39; Yang, Z. Q. et al. (2001) Jpn. J. Cancer Res. 92, 423-28; Hu, N. et al. (2005) Cancer Res. 65, 2542-46; Liu, G. et al. (2009) Oncogene 28, 4491-500; Wissmann, M. et al. (2007) Nat. Cell Biol. 9, 347-53), indicating the potential importance of JMJD2C as an oncogene.

The JMJD2A protein (KDM4A, JHDM3A) shows similar properties to JMJD2C. JMJD2A shows high sequence identity to JMJD2C in its JmjC catalytic domain, is an eraser of the H3K9 mark and has also been shown to be overexpressed in prostate cancer (Cloos, P. Et al., Nature 442, 307-11, 2006). JMJD2A has been shown to interact with the estrogen receptor alpha (ER-alpha) and overexpression of JMJD2A enhances estrogen-dependent transcription and the down-regulation of JMJD2A reduced transcription of a seminal ER-alpha target gene, cyclin D1 (Kawazu et al., (2011) PLoS One 6; Berry et al., (2012) Int J Oncol 41). Additionally, it has been shown that catalytically inactive JMJD2A is compromised in its ability to stimulate ER-alpha mediated transcription, suggesting that inhibitors of JMJD2A may be beneficial for the treatment of ER-alpha positive breast tumours (Berry et al., (2012) Int J Oncol 41).

Likewise, an eraser of the tri-methyl variant of the H3K4 mark, JARID1B (KDM5B, PLU1) has also been identified as potential oncogene. In cancer JARID1B most likely acts as a repressor of tumour repressor genes via removal of the H3K4 tri-methylation leading to decreased transcriptional activation in the affected chromatin regions. The oncogenic potential of JARID1B is demonstrated by its stimulation of proliferation in cell lines and further validated by shRNA knockdown studies of JARID1B expression showing inhibition of proliferation in MCF7 human breast cancer cells, in SW780 and RT4 bladder cancer cells, in A549 and LC319 lung cancer cells and in 4T1 mouse tumour cells in vitro and/or in mouse xenograft experiments (Yamane K. et al. (2007), Mol. Cell 25, 801-12; Hayami S. et al. (2010) Mol. Cancer 9, 59; Catchpole S et al. (2011), Int. J. Oncol. 38, 1267-77). Finally, JARID1B is overexpressed in prostate cancer and is associated with malignancy and poor prognosis (Xiang Y. et al. (2007) PNAS 104).

JARID1A (KDM5A, RBP2) is also an eraser of the tri- and di-methyl variant of the H3K4 mark. JARID1A is overexpressed in gastric cancer (Zeng et al., (2010) Gastroenterology 138) and its gene is amplified in cervix carcinoma (Hidalgo et al, (2005) BMC Cancer 5). It has been suggested that JARID1A is fine-tuning progesterone receptor expression control by estrogens (Stratmann and Haendler (2011) FEBS J 278). Together with JARID1B, JARID1A has been implicated in the maintenance of a slow-growing population of cancer cells that are required for continuous tumor growth and that are resistant to cytotoxic and targeted therapy (Roesch, et al, (2010) Cell 141; Sharma, et al., (2010) Cell 141). JARID1A is required for the tumor initiation and progression in Rb+/− and Men1-defective mice (Lin, et al., (2011) PNAS 108). Data from Pasini show that JARID1A binds to Polycomb group protein target genes which are involved in regulating important cellular processes such as embryogenesis, cell proliferation, and stem cell self-renewal through the transcriptional repression of genes determining cell fate decisions (Pasini et al., (2008) Genes & Dev 22). Additionally, JARID1A were also shown to binds the PRC2 complex and being regulator of PRC2 target genes (Pasini et al., (2008) Genes & Dev 22).

Another potential oncogene, an eraser of the di-methyl variant of the H3K36 mark, JHDM1B (KDM2B, FBXL10) has been shown to be highly expressed in human cancers (Tzatsos A et al. (2009), PNAS 106 (8), 2641-6; He, J. et al. (2011), Blood 117 (14), 3869-80). Knock-down of FBXL10 causes senescence in mouse embryonic fibroblasts (MEFs), which can be rescued by expression of catalytic active (but not catalytic inactive) JHDM1B (Pfau R et al. (2008), PNAS 105(6), 1907-12; He J et al. (2008), Nat Struct Mol Biol 15, 1169-75). JHDM1B demethylates H3K36me2 on the tumor-suppressor gene Ink4b (p15$^{Ink4b}$), and thereby silences the expression of this senescence-mediating gene in MEFs and in leukemic cells (He, J. et al. (2008), Nat Struct Mol Biol 15, 1169-75; He, J. et al. (2011), Blood 117 (14), 3869-80). The catalytic dependency of JHDM1B is further shown by He et al. as catalytic activity is required for development of leukemia in a mouse AML model.

Inhibitors of the histone demethylase class of epigenetic enzymes, and in particular the potential oncogenes JARID1B, JARID1A, JMJD2C, JMJD2A, and JHDM1B, would present a novel approach for intervention in cancers and other proliferative diseases. Being one of the most devastating diseases, affecting millions of people worldwide, there remains a high need for efficacious and specific compounds against cancer.

Embodiments of the invention provide novel series of compounds capable of modulating the activity of histone demethylases (HDMEs), at least some of which compounds are useful for the prevention and/or the treatment of diseases in which genomic disregulation is involved in the pathogenesis, such as e.g. cancer. By way of further example, malnutrition or poor nutrition is thought to have an adverse epigenetic effect and the compounds of the invention may therefore be expected to have beneficial effect in treating such effects of poor nutrition. Furthermore, epigenetic changes have been found to be linked to behaviour. Accordingly, compounds according to the invention may be useful in behaviour modification. Alternatively or additionally such compounds may be useful for exploring the extent to which different demethylases are inhibited by similar compounds as an investigation of the structure and functionality and mechanism of action of the demethylases.

SUMMARY OF THE INVENTION

Accordingly, the invention provides a compound of the general Formula (I)

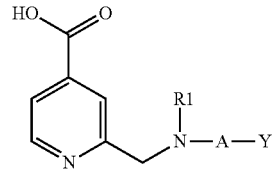

wherein

A is selected from —CHR$^2$C(O)—, C$_{1-8}$ alkylene, C$_{2-8}$ alkenylene, C$_{2-8}$ alkynylene, C$_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more R$^3$;

Y is selected from —H, —NR$^6$R$^7$, —OR$^7$, C$_{1-8}$ alkyl, C$_{2-8}$ alkenyl, C$_{2-8}$ alkynyl, C$_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R$^3$ and may form a cyclic structure with R$^2$;

R$^1$ is selected from —H, C$_{1-8}$ alkyl, C$_{2-8}$ alkenyl, C$_{2-8}$ alkynyl, C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl; or more preferably is selected from —H and C$_{1-4}$ alkyl; or with -A-Y forms a nitrogen containing optionally substituted heterocyclic group where the optional substitution may be C$_{1-8}$ alkyl, C$_{2-8}$ alkenyl, C$_{2-8}$ alkynyl, or C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl;

R$^2$ is selected from —H, C$_{1-8}$ alkyl, C$_{2-8}$ alkenyl, C$_{2-8}$ alkynyl, and C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl, and may form a cyclic structure with Y;

each R$^3$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$;

Z is selected from a single bond, C$_{1-4}$ alkylene, heterocyclylene and C$_{3-6}$ cycloalkylene;

each R$^4$ is independently selected from C$_{1-6}$ alkyl, C$_{1-4}$ fluoroalkyl, C$_{1-4}$ hydroxyalkyl, C$_{1-4}$ alkoxy, C$_{3-10}$ cycloalkyl, —N(R$^1$)$_2$, carbamoyl, and —OH;

each R$^5$ is independently selected from C$_{1-6}$ alkyl, C$_{1-4}$ fluoroalkyl, C$_{1-4}$ hydroxyalkyl, C$_{1-4}$ alkoxy, C$_{3-6}$ cycloalkyl, —CN, —F, —Cl, —Br, carbamoyl and —OH;

each of R$^6$ and R$^7$ is independently selected from —H, C$_{1-8}$ alkyl, C$_{1-4}$ fluoroalkyl, C$_{1-4}$ perfluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

with the proviso that Y is not H when A is —$CH_2$—;

or an isomer or a mixture of isomers thereof, or a pharmaceutically acceptable salt, solvate or prodrug thereof.

Where $R^1$ forms with -A-Y an optionally substituted heterocyclic group, it is preferably an optionally substituted $C_{3-7}$ for instance $C_{3-6}$ or $C_{5-6}$ heterocyclic group.

Where $R^2$ forms a cyclic structure with Y, $R^2$ is preferably $C_1$-$C_2$ alkylene. The cyclic structure is preferably an optionally substituted (with one or more $R^3$) 5 or 6 membered, optionally heterocyclic, ring.

A preferred aspect of the present invention relates to a compound of the Formula (I)

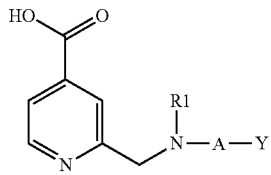

wherein

A is selected from —$CHR^2C(O)$—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more $R^3$;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$;

$R^1$ is selected from —H and $C_{1-4}$ alkyl;

$R^2$ is selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —$N(R^1)_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

with the proviso that Y is not H when A is —CH$_2$—;

or an isomer or a mixture of isomers thereof, or a pharmaceutically acceptable salt, solvate or prodrug thereof.

In an alternative aspect, the invention relates to a compound of the Formula 1 wherein A is selected from —CHR$^2$C(O)—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylen, alkynylene, cycloalkylene, heterocyclylene, heteroarylene and arylene may optionally be substituted with one or more $R^3$;

Y is selected from —H, —NR$^6$R$^7$, —OR$^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$;

$R^1$ is selected from —H and $C_{1-4}$ alkyl;

$R^2$ is selected from —H, $C_{1-4}$ alkyl and $C_{1-4}$ hydroxyalkyl;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—OR$^7$, halogen, —Z—SR$^7$, —Z—SOR$^7$, —Z—SO$_2$R$^7$ and —Z—COOR$^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene, each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N(R$^1$)$_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^2$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Y-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with a N-atom to which they are attached form an N-heterocyclic ring optionally substituted with one or more $R^4$ as defined above;

with the proviso that Y is not H when A is —CH$_2$—; or an isomer or a mixture of isomers thereof, or a pharmaceutically acceptable salt, solvate or prodrug thereof.

A further aspect of the present invention relates to pharmaceutical compositions comprising at least one compound of Formula (I) as defined herein, and optionally one or more pharmaceutically acceptable excipients, diluents and/or carriers.

A further aspect of the present invention relates to a compound of Formula (I) as defined herein for use as a medicament.

A further aspect of the present invention relates to a compound of Formula (I) as defined herein for use in the treatment of a HDME dependent disease, such as for the treatment of cancer.

A further aspect of the present invention relates to a compound of Formula (I) as defined herein for use in the preparation of a pharmaceutical composition for the treatment of a HDME dependent disease, such as cancer.

A further aspect of the invention relates to a method of treating a HDME dependent disease in a subject, said method comprises administering to said subject a therapeutically effective amount of at least one compound of Formula (I) as defined herein.

Compounds of Formula (I) as defined herein can be used in the treatment of HDME dependent diseases by inhibiting HDMEs. Inhibiting HDMEs would provide a novel approach to the prevention and treatment of cancer and other proliferative diseases. Administered alone or optionally in combination with anti-neoplastic compounds, the compounds of the invention increase the efficacy of the treatment of HDME dependent diseases. As will be shown below, compounds of the invention have a cytostatic or antiproliferative action against cancer cells.

DETAILED DISCLOSURE OF THE INVENTION

Compounds of Formula (I)

As mentioned above, the present invention relates to compounds of Formula (I)

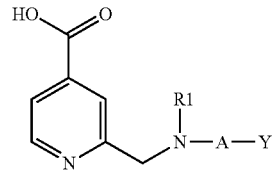

The above definition of the compounds of Formula (I) is referred to herein by the expressions "compounds of Formula (I)" as defined herein, "compound of Formula (I) as defined herein", or simply "compounds of Formula (I)", etc. It should be understood, that such references are intended to encompass not only the above general formula, but also each and and every one of the embodiments, etc. discussed above or in the following. It should also be understood, that unless the opposite is stated, such references also encompass isomers, mixtures of isomers, pharmaceutically acceptable salts, solvates and prodrugs of the compounds of Formula (I).

Without being bound by any particular theory, the current results and X-ray crystallography studies give reasons to believe that the HOOC-pyridine-$CH_2$—N< motif, cf. Formula (I), plays an important role when designing compounds capable of modulating the activity of histone demethylases (HDMEs). Furthermore, it is believed that the substituent combination -A-Y plays a role in establishing affinity for said histone demethylases. Histone demethylases contain an iron atom on which their activity depends. It is furthermore believed that the pyridine nitrogen and the nitrogen atom of Formula (I) also play a role in the binding of a particular cavity of the histone demethylases where the iron atom lies, probably by chelation of the iron itself.

It is also believed that the A-Y chain, itself and through its substituents, interacts with the area of the demethylase known to accommodate the lysine chain of the substrate. As the experimental results presented below in the examples clearly demonstrate, there is a wide range of possibilities for the -A-Y group that modulate activity at various demethylases, imparting selective inhibition. Some demethylases have the lysine chain area lined with acidic residues and compounds with basic groups in Y show enhanced potency on these enzymes. Similarly, some demethylases are better inhibited by compounds with apolar groups in the Y chain. Yet other demethylases are better inhibited by compounds with non-charged polar groups in the Y chain. Yet other demethylases are better inhibited by compounds with non-charged polar groups in the Y chain.

More particularly, it is believed that the carboxylic acid substituent of the pyridine ring plays a role in binding to a particular cavity of histone demethylases.

A is typically selected from —$CHR^2C(O)$—, $C_{1-8}$ alkylene, $C_{2-8}$ alkenylene, $C_{2-8}$ alkynylene, $C_{3-10}$ cycloalkylene, heterocyclylene, heteroarylene and arylene.

The alkylene, alkenylene, alkynylene, cycloalkylene, heterocyclylene, heteroarylene and arylene as A may optionally be substituted with one or more $R^3$ (see further below).

In one embodiment, A is selected from —$CHR^2C(O)$—, $C_{1-8}$ alkylene, $C_{3-10}$ cycloalkylene, heterocyclylene, heteroarylene and arylene, in particular from —$CHR^2C(O)$—, $C_{1-8}$ alkylene and heterocyclylene, such as —$CHR^2C(O)$—, or $C_{1-8}$ alkylene, or heterocyclylene. In this context, $R^2$ may take any of the sets of values given for it above or below.

In particular, A may be —$CH_2C(O)$— or —$CH_2$—$CH_2$—.

Y is typically selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl. Preferred values for $R^6$ and $R^7$ are defined further below.

The alkyl, alkenyl, alkynyl, cycloalkyl, heterocyclyl, heteroaryl and aryl as Y may optionally be substituted with one or more $R^3$ (see further below);

In one embodiment, Y is —$NR^6R^7$. In one variant, A is —$CHR^2C(O)$—, especially —$CH_2C(O)$—, and Y is —$NR^6R^7$.

In particular, -A-Y may take any of the values illustrated in the compounds of Table 1 below and any value of —Y shown there may be combined with any illustrated value for -A.

In another variant, A is $C_{1-8}$ alkyl and Y is —$NR^6R^7$. In one scenario within this embodiment and these variants, —$NR^6R^7$ represents an N-heterocyclic ring optionally substituted with one or more independently selected $R^8$, preferably substituted with one to two independently selected $R^8$. In another scenario within this embodiment and these variants wherein Y is —$NR^6R^7$, one of $R^6$ and $R^7$ represents —H or $C_{1-6}$ alkyl. In still another scenario within this embodiment and these variants wherein Y is —$NR^6R^7$, $R^6$ and $R^7$ are independently selected from $C_{1-8}$ alkyl, $C_{1-4}$ fluoroalkyl, $C_{1-4}$ hydroxyalkyl, $C_{2-8}$ alkenyl, and $C_{2-8}$ alkynyl, e.g. such that $R^6$ and $R^7$ are the same. In still another scenario within this embodiment and these variants wherein Y is —$NR^6R^7$, one of $R^6$ and $R^7$ is selected from heterocyclyl, heteroaryl and aryl.

In another embodiment, Y is —H. In one variant, A is selected from $C_{1-8}$ alkylene, $C_{2-8}$ alkenylene, $C_{2-8}$ alkynylene, and $C_{3-10}$ cycloalkylene. In another variant, A is selected from heterocyclyl.

In still another embodiment, Y is selected from heterocyclyl, heteroaryl and aryl. In one variant hereof, A is selected from $C_{1-8}$ alkylene, $C_{2-8}$ alkenylene, $C_{2-8}$ alkynylene, in particular from $C_{1-8}$ alkylene, such as from $C_{1-6}$ alkylene, in particular from $C_{1-4}$ alkylene.

$R^1$ is typically selected from —H and $C_{1-4}$ alkyl (such as methyl, ethyl, propyl and butyl), in particular from —H and methyl, H being preferred.

$R^2$ is typically selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl. In some embodiments, $R^2$ is selected from —H, $C_{1-4}$ alkyl (such as methyl, ethyl, propyl and butyl) and $C_{1-4}$ hydroxyalkyl (such as hydroxymethyl, hydroxyethyl, hydroxypropyl and hydroxybutyl), in particular from —H, methyl and hydroxymethyl, with H being preferred.

The $R^3$ (possible substituents to some of the meanings of A and Y) is typically independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$. In another embodiment, $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-aryl, —Z-heteroaryl, —Z—$NR^6R^7$, —Z—C(=O)—$NR^6R^7$, —Z—$OR^7$, halogen, —Z—$SR^7$, —Z—$SOR^7$, —Z—$SO_2R^7$ and —Z—$COOR^7$, wherein any heterocyclyl may be substituted with one or more $R^4$, and wherein any heteroaryl and any aryl may be substituted with one or more $R^5$.

Z is typically selected from a single bond, $C_{1-4}$ alkylene, heterocyclylene and $C_{3-6}$ cycloalkylene. In one embodiment, Z is selected from $C_{1-4}$ alkylene. In another embodiment, Z is selected from a single bond. It should be understood that the group Z may appear several times in Formula (I) and that such Z's are independently selected.

Each $R^4$ (possible substituents of heterocyclyl) is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —$N(R^1)_2$, carbamoyl, and —OH.

Each $R^5$ (possible substituents of heteroaryl and aryl) is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH.

Each of $R^6$ and $R^7$ (e.g. of the moiety —$NR^6R^7$) is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$.

Each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{16}R^{11}$, —Z—C(=O)—$NR^{10}R^{11}$, —Z—$OR^9$, halogen, —CN, —Z—$SR^9$, —Z—$SOR^9$, —Z—$SO_2R^8$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above.

Each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above. In one embodiment, each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-aryl, and —Z-heteroaryl, wherein any heterocyclyl may be substituted with one or more $R^4$ as defined above, and wherein any heteroaryl and any aryl may be substituted with one or more $R^5$ as defined above.

Each of $R^{10}$ and $R^{11}$ (of the moiety —$NR^{10}R^{11}$) is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above.

It is to be understood that in the Formula (I), Y is not H when A is —$CH_2$—. Generally speaking, it is believed to be advantageous if the moiety -A-Y has a certain "size" with respect to the number of atom (disregarding hydrogen atoms) and/or the molecular weight. Also a limited flexibility of the moiety -A-Y appears to play a certain role.

Hence, it is believed that the moiety -A-Y should preferably consist of at the most 40 heavy atoms, such as at the most 30 heavy atoms, such as at the most 25 heavy atoms, or at the most 20 heavy atoms. Preferably, the moiety -A-Y will consist of at least 3, or at least 4, or at least 8 or at least 10 heavy atoms. In some embodiments, the moiety -A-Y preferably consists of 3-40 heavy atoms, such as 4-30 heavy atoms, or 4-25 heavy atoms, or 4-20, or 8-30, or 8-20, or 8-15 heavy atoms. By the term "heavy atom" is meant all atoms in the moiety except the hydrogen atom(s).

Moreover, it is believed that the compounds of Formula (I) should preferably have a molecular weight of at least 130, or at least 150, or at least 180, or at least 250, but not more than 1000, or not more than 800, or not more than 500, or not more than 400 and may be within any range constructable from these preferred upper and lower limits, such as 130-1,000 g/mol, or 150-1,000 g/mol, such as 180-800 g/mol, e.g. 225-600 g/mol or 250-500 g/mol, or 250 to 400.

In some embodiments, and in order to introduce a limited flexibility of the moiety -A-Y, the moiety includes 1-4 rings, i.e. rings derived from cycloalkyl, cycloalkenyl, heterocyclyl, heteroaryl and/or aryl. In some variant, the moiety -A-Y includes 1-3 cyclic moieties selected from monocylic cycloalkyl, monocyclic heterocyclyl, monocylic heteroaryl, dicyclic heteroaryl and monocyclic aryl. Small substituents such as alkyls groups or hydroxyl on alkyl chains also reduce flexibility and favor certain conformations.

It may be preferable that if -A-Y does not include a ring, it includes at least one, for instance from 1 to 3, branches, each of which independently may be of from one heavy atom to six heavy atoms, for instance from one to three heavy atoms, or from one to two heavy atoms. It is preferred that -A-Y should contain at least one hetero-atom, preferably at least one nitrogen atom or at least one oxygen.

Options independently adoptable include that:

Y is

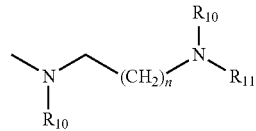

wherein n is from 1 to 3 and each of $R_{10}$ and $R_{11}$ independently is as defined above.

Y is

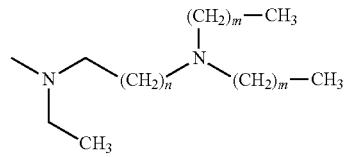

wherein n is from 1 to 3 and each m independently is from 0 to 2.

Y is selected from heterocyclyl, heteroaryl and aryl, which may be optionally substituted with one or more $R^3$.

Based on the studies conducted and the results obtained so far, it is believed that the following compounds (numbered 1 to 45), including isomers, mixtures of isomers, as well as pharmaceutically acceptable salts, solvates and prodrugs thereof, are particularly interesting:

1  2-({[3-(1H-imidazol-1-yl)propyl]amino}methyl)pyridine-4-carboxylic acid
2  2-({[2-(dimethylamino)ethyl]amino}methyl)pyridine-4-carboxylic acid 3  2-({[(2R)-2,3-dihydroxypropyl]amino}methyl)pyridine-4-carboxylic acid
4  2-{[(cyclopropylmethyl)amino]methyl}pyridine-4-carboxylic acid
5  2-{[(cyclopropylmethyl)amino]methyl}pyridine-4-carboxylic acid
6  2-({[2-(dimethylamino)ethyl](methyl)amino}methyl)pyridine-4-carboxylic acid
7  2-{[methyl(prop-2-yn-1-yl)amino]methyl}pyridine-4-carboxylic acid
8  2-{[(2-fluoroethyl)amino]methyl}pyridine-4-carboxylic acid
9  2-{[(furan-2-ylmethyl)amino]methyl}pyridine-4-carboxylic acid
10  2-({[(5-phenylfuran-2-yl)methyl]amino}methyl)pyridine-4-carboxylic acid
11  2-({[(2,4-dimethoxyphenyl)methyl]amino}methyl)pyridine-4-carboxylic acid
12  2-({[2-(methylsulfanyl)ethyl]amino}methyl)pyridine-4-carboxylic acid
13  2-({[2-oxo-2-(pyrrolidin-1-yl)ethyl]amino}methyl)pyridine-4-carboxylic acid
14  2-[({[butyl(methyl)carbamoyl]methyl}amino)methyl]pyridine-4-carboxylic acid
15  2-({[(1-methyl-1H-1,3-benzodiazol-2-yl)methyl]amino}methyl)pyridine-4-carboxylic acid
16  2-[({2-[4-(2-methoxyethyl)piperazin-1-yl]-2-oxoethyl}amino)methyl]pyridine-4-carboxylic acid
17  2-[({[bis(prop-2-en-1-yl)carbamoyl]methyl}amino)methyl]pyridine-4-carboxylic acid
18  2-[({2-oxo-2-[(2R)-2-(pyrrolidin-1-ylmethyl)pyrrolidin-1-yl]ethyl}amino)methyl]-pyridine-4-carboxylic acid
19  2-({[(3R)-1-[(tert-butoxy)carbonyl]pyrrolidin-3-yl]amino}methyl)pyridine-4-carboxylic acid
20  2-({[(3R)-1-[(tert-butoxy)carbonyl]pyrrolidin-3-yl]amino}methyl)pyridine-4-carboxylic acid
21  2-{[(3-{3-(pyrrolidin-1-yl)propyl]amino}propyl)amino]methyl}pyridine-4-carboxylic acid
22  2-{[(3-methylbutyl)amino]methyl}pyridine-4-carboxylic acid
23  2-[({[(2-carbamoylethyl)(methyl)carbamoyl]methyl}amino)methyl]pyridine-4-carboxylic acid
24  2-[({2-[2-(hydroxymethyl)piperidin-1-yl]-2-oxoethyl}amino)methyl]pyridine-4-carboxylic acid
25  2-{[({methyl[3-(1-methyl-1H-imidazol-2-yl)propyl]carbamoyl}methyl)amino]methyl}-pyridine-4-carboxylic acid
26  2-{[({[(1-ethylpyrrolidin-2-yl)methyl]carbamoyl}methyl)amino]methyl}pyridine-4-carboxylic acid
27  2-{[({(methyl[(1-methyl-1H-pyrazol-5-yl)methyl]carbamoyl}methyl)amino]-methyl}pyridine-4-carboxylic acid
28  2-({[(3R)-1-(3-phenylpropyl)pyrrolidin-3-yl]amino}methyl)pyridine-4-carboxylic acid
29  2-({[({1-[(2-methoxyphenyl)methyl]piperidin-4-yl}carbamoyl)methyl]amino}-methyl)-pyridine-4-carboxylic acid
30  2-{[({[1-(3-phenylpropyl)piperidin-4-yl]carbamoyl}methyl)amino]methyl}pyridine-4-carboxylic acid
31  2-{[({[1-(furan-2-ylmethyl)piperidin-4-yl]carbamoyl}methyl)amino]methyl}pyridine-4-carboxylic acid
32  2-({[({1-[(5-phenylfuran-2-yl)methyl]piperidin-4-yl}carbamoyl)methyl]amino}-methyl)pyridine-4-carboxylic acid
33  2-[({[(2-cyanoethyl)(ethyl)carbamoyl]methyl}amino)methyl]pyridine-4-carboxylic acid
34  2-({[2-(1-butylpyrrolidin-2-yl)ethyl]amino}methyl)pyridine-4-carboxylic acid
35  2-{[({[1-(3,7-dimethyloct-6-en-1-yl)pyrrolidin-3-yl]carbamoyl}methyl)amino]-methyl}pyridine-4-carboxylic acid
36  2-{[(3-{[(2-fluorophenyl)methyl](methyl)amino}propyl)amino]methyl}pyridine-4-carboxylic acid
37  2-({[(1R)-2-hydroxy-1-{methyl[3-(1-methyl-1H-imidazol-2-yl)propyl]carbamoyl}-ethyl]amino}methyl)pyridine-4-carboxylic acid
38  2-[({2-[3-(1H-1,3-benzodiazol-2-ylmethyl)piperidin-1-yl]-2-oxoethyl}amino)methyl]-pyridine-4-carboxylic acid
39  2-{[({[1-(2-phenylethyl)pyrrolidin-3-yl]carbamoyl}methyl)amino]methyl}pyridine-4-carboxylic acid
40  2-({[3-(4-benzylpiperidin-1-yl)propyl]amino}methyl)pyridine-4-carboxylic acid
41  2-[({3-[(2-phenoxyethyl)amino]propyl}amino)methyl]pyridine-4-carboxylic acid
42  2-[({[methyl({4-[(4-methylpiperazin-1-yl)methyl]phenyl}methyl)carbamoyl]methyl}-amino)methyl]pyridine-4-carboxylic acid
43  2-({[2-(2-benzylpyrrolidin-1-yl)-2-oxoethyl]amino}methyl)pyridine-4-carboxylic acid
44  2-({[({4-[benzyl(cyclopropyl)amino]butyl}(methyl)carbamoyl)methyl]-amino}methyl)pyridine-4-carboxylic acid
45  2-[({2-[(2S)-1-benzylpyrrolidin-2-yl]ethyl}amino)methyl]pyridine-4-carboxylic acid
46  2-({[3-(pyrrolidin-1-yl)propyl]amino}methyl)pyridine-4-carboxylic acid
47  methyl 2-({[3-(pyrrolidin-1-yl)propyl]amino}methyl)pyridine-4-carboxylate
48  2-({[4-(diethylamino)butyl]amino}methyl)pyridine-4-carboxylic acid
49  2-{[({[2-(dimethylamino)ethyl](ethyl)carbamoyl}methyl)amino]methyl}pyridine-4-carboxylic acid
50  (5-methyl-2-oxo-2H-1,3-dioxol-4-yl)methyl 2-({[4-(diethylamino)butyl]amino}methyl)pyridine-4-carboxylate
51  4-methoxyphenyl 2-({[4-(diethylamino)butyl]amino}methyl)pyridine-4-carboxylate
52  2-(ethoxycarbonyl)phenyl 2-({[4-(diethylamino)butyl]amino}methyl)pyridine-4-carboxylate
53  2-(dimethylamino)ethyl 2-({[4-(diethylamino)butyl]amino}methyl)pyridine-4-carboxylate
54  3-(dimethylamino)propyl 2-({[4-(diethylamino)butyl]amino}methyl)pyridine-4-carboxylate
55  {4-{[(ethoxycarbonyl)amino]phenyl}methyl 2-({[4-(diethylamino)butyl]amino}methyl)pyridine-4-carboxylate
56  2,6-dimethoxyphenyl 2-({[4-(diethylamino)butyl]amino}methyl)pyridine-4-carboxylate
57  2,6-dimethylphenyl 2-({[4-(diethylamino)butyl]amino}methyl)pyridine-4-carboxylate
58  4-methoxyphenyl 2-{[({[2-(dimethylamino)ethyl](ethyl)carbamoyl}methyl)amino]methyl}pyridine-4-carboxylate
59  2-(ethoxycarbonyl)phenyl 2-{[({[2-(dimethylamino)ethyl](ethyl)carbamoyl}methyl)amino]methyl}pyridine-4-carboxylate
60  {4-[(ethoxycarbonyl)(methyl)amino]phenyl}methyl 2-({[4-(diethylamino)butyl]amino}methyl)pyridine-4-carboxylate 61 4-tert-butylphenyl 2-{[({2-(dimethylamino)ethyl](ethyl)carbamoyl}methyl)amino]methyl}pyridine-4-carboxylate
62 4-oxopentan-2-yl 2-{[({2-(dimethylamino)ethyl](ethyl)carbamoyl}methyl)amino]methyl}pyridine-4-carboxylate
63 4-(trifluoroacetamido)butan-2-yl 2-{[({2-(dimethylamino)ethyl](ethyl)carbamoyl}methyl)amino]methyl}pyridine-4-carboxylate
64 4-(2,2,2-trifluoro-N-methylacetamido)butan-2-yl 2-{[({2-(dimethylamino)ethyl](ethyl)carbamoyl}methyl)amino]methyl}pyridine-4-carboxylate
65 ethyl 2-{[({2-(dimethylamino)ethyl](ethyl)carbamoyl}methyl)amino]methyl}pyridine-4-carboxylate
66 5-(trifluoroacetamido)pent-1-en-3-yl 2-{[({2-(dimethylamino)ethyl](ethyl)carbamoyl}methyl)amino]methyl}pyridine-4-carboxylate
67 5-(2,2,2-trifluoro-N-methylacetamido)pent-1-en-3-yl 2-{[({2-(dimethylamino)ethyl](ethyl)carbamoyl}methyl)amino]methyl}pyridine-4-carboxylate
68 2-(2-{[({2-(dimethylamino)ethyl](ethyl)carbamoyl}methyl)amino]methyl}pyridine-4-carbonyloxy)-3-(hexadecanoyloxy)propyl hexadecanoate
69 1-(2-{[({2-(dimethylamino)ethyl](ethyl)carbamoyl}methyl)amino]methyl}pyridine-4-carbonyloxy)-3-(hexadecanoyloxy)propan-2-yl hexadecanoate
70 methyl 2-{[({2-(dimethylamino)ethyl](ethyl)carbamoyl}methyl)amino]methyl}pyridine-4-carboxylate
71 2-{[({2-(dimethylamino)ethyl](ethyl)carbamoyl}methyl)amino]methyl}-N-methanesulfonyl-N-methylpyridine-4-carboxamide
72 N-[2-(dimethylamino)ethyl]-N-ethyl-2-({[4-(2-oxo-1,3-oxazolidine-3-carbonyl)pyridin-2-yl]methyl}amino)acetamide
73 propan-2-yl 3-(2-{[({2-(dimethylamino)ethyl](ethyl)carbamoyl}methyl)amino]methyl}pyridine-4-carbonyloxy)-4-(trifluoroacetamido)butanoate
74 propan-2-yl 3-(2-{[({2-(dimethylamino)ethyl](ethyl)carbamoyl}methyl)amino]methyl}pyridine-4-carbonyloxy)-5-(trifluoroacetamido)pentanoate
75 2-{[({2-(dimethylamino)ethyl](ethyl)carbamoyl}methyl)amino]methyl}-N-(pyridin-4-yl)pyridine-4-carboxamide
76 2-{[({2-(dimethylamino)ethyl](ethyl)carbamoyl}methyl)amino]methyl}-N-(5-methyl-1,3,4-oxadiazol-2-yl)pyridine-4-carboxamide
77 2-{[({2-(dimethylamino)ethyl](ethyl)carbamoyl}methyl)amino]methyl}-N-(1-methyl-1H-pyrazol-5-yl)pyridine-4-carboxamide
78 2-(piperidin-1-ylmethyl)pyridine-4-carboxylic acid
79 2-(azetidin-1-ylmethyl)pyridine-4-carboxylic acid
80 2,2,2-trifluoroethyl 2-{[({2-(dimethylamino)ethyl](ethyl)carbamoyl}methyl)amino]methyl}pyridine-4-carboxylate
81 2-({ethyl[2-oxo-2-(piperidin-1-yl)ethyl]amino}methyl)pyridine-4-carboxylic acid
82 2-({butyl[2-oxo-2-(piperidin-1-yl)ethyl]amino}methyl)pyridine-4-carboxylic acid
83 2-({benzyl[2-oxo-2-(piperidin-1-yl)ethyl]amino}methyl)pyridine-4-carboxylic acid
84 2-{[({2-(dimethylamino)ethyl](ethyl)carbamoyl}methyl)amino]methyl}-N-(1,3-oxazol-2-yl)pyridine-4-carboxamide
85 2,6-bis(propan-2-yloxy)phenyl 2-{[({2-(dimethylamino)ethyl](ethyl)carbamoyl}methyl)amino]methyl}pyridine-4-carboxylate
86 2-{[(2-methylpropyl)[2-oxo-2-(piperidin-1-yl)ethyl]amino]methyl}pyridine-4-carboxylic acid
87 2-({[2-oxo-2-(piperidin-1-yl)ethyl](propyl)amino}methyl)pyridine-4-carboxylic acid
88 2-({[2-oxo-2-(piperidin-1-yl)ethyl](propan-2-yl)amino}methyl)pyridine-4-carboxylic acid
89 2-{[({2-(dimethylamino)ethyl](ethyl)carbamoyl}methyl)amino]methyl}-N-(1-methyl-1H-imidazol-2-yl)pyridine-4-carboxamide
90 2-fluoroethyl 2-{[({2-(dimethylamino)ethyl](ethyl)carbamoyl}methyl)amino]methyl}pyridine-4-carboxylate
91 2,2-difluoroethyl 2-{[({2-(dimethylamino)ethyl](ethyl)carbamoyl}methyl)amino]methyl}pyridine-4-carboxylate
92 2-({[(1S)-1-(tert-butylcarbamoyl)-3-methylbutyl]amino}methyl)pyridine-4-carboxylic acid
93 2-({methyl[(2S)-4-methyl-1-oxo-1-(piperidin-1-yl)pentan-2-yl]amino}methyl)pyridine-4-carboxylic acid Further compounds of particular interest are illustrated in Table 1 below and in the other examples.

Definitions

The term "alkyl" as used herein refers to a saturated, straight or branched hydrocarbon chain. The hydrocarbon chain preferably contains from one to 8 carbon atoms ($C_{1-8}$-alkyl), more preferred from one to six carbon atoms ($C_{1-6}$-alkyl), in particular from one to four carbon atoms ($C_{1-4}$-alkyl), including methyl, ethyl, propyl, isopropyl, butyl, isobutyl, secondary butyl, tertiary butyl, pentyl, isopentyl, neopentyl, tertiary pentyl, hexyl, isohexyl, heptyl and octyl. In a preferred embodiment "alkyl" represents a $C_{1-4}$-alkyl group, which may in particular include methyl, ethyl, propyl, isopropyl, butyl, isobutyl, secondary butyl, and tertiary butyl. Correspondingly, the term "alkylene" means the corresponding biradical (-alkyl-).

The term "cycloalkyl" as used herein refers to a cyclic alkyl group, preferably containing from three to ten carbon atoms ($C_{3-10}$-cycloalkyl), such as from three to eight carbon atoms ($C_{3-8}$-cycloalkyl), preferably from three to six carbon atoms ($C_{3-6}$-cycloalkyl), including cyclopropyl, cyclobutyl, cyclopentyl, cyclohexyl, cycloheptyl and cyclooctyl. Furthermore, the term "cycloalkyl" as used herein may also include polycyclic groups such as for example bicyclo[2.2.2]octyl, bicyclo[2.2.1]heptanyl, decalinyl and adamantyl. Correspondingly, the term "cycloalkylene" means the corresponding biradical (-cycloalkyl-).

The term "alkenyl" as used herein refers to a straight or branched hydrocarbon chain or cyclic hydrocarbons containing one or more double bonds, including di-enes, tri-enes and poly-enes. Typically, the alkenyl group comprises from two to eight carbon atoms ($C_{2-8}$-alkenyl), such as from two to six carbon atoms ($C_{2-6}$-alkenyl), in particular from two to four carbon atoms ($C_{2-4}$-alkenyl), including at least one double bond. Examples of alkenyl groups include ethenyl; 1- or 2-propenyl; 1-, 2- or 3-butenyl, or 1,3-but-dienyl; 1-, 2-, 3-, 4- or 5-hexenyl, or 1,3-hex-dienyl, or 1,3,5-hextrienyl; 1-, 2-, 3-, 4-, 5-, 6-, or 7-octenyl, or 1,3-octadienyl, or 1,3,5-octatrienyl, or 1,3,5,7-octatetraenyl, or cyclohexenyl. Correspondingly, the term "alkenylene" means the corresponding biradical (-alkenyl-).

The term "alkynyl" as used herein refers to a straight or branched hydrocarbon chain containing one or more triple bonds, including di-ynes, tri-ynes and poly-ynes. Typically, the alkynyl group comprises of from two to eight carbon atoms ($C_{2-8}$-alkynyl), such as from two to six carbon atoms ($C_{2-6}$-alkynyl), in particular from two to four carbon atoms ($C_{2-4}$-alkynyl), including at least one triple bond. Examples of preferred alkynyl groups include ethynyl; 1- or 2-propynyl; 1-, 2- or 3-butynyl, or 1,3-but-diynyl; 1-, 2-, 3-, 4- or 5-hexynyl, or 1,3-hex-diynyl, or 1,3,5-hex-triynyl; 1-, 2-, 3-, 4-, 5-, 6-, or 7-octynyl, or 1,3-oct-diynyl, or 1,3,5-oct-triynyl, or 1,3,5,7-oct-tetraynyl. Correspondingly, the term "alkynylene" means the corresponding biradical (-alkynyl-).

The terms "halo" and "halogen" as used herein refer to fluoro, chloro, bromo or iodo. Thus a trihalomethyl group represents e.g. a trifluoromethyl group, or a trichloromethyl group. Preferably, the terms "halo" and "halogen" designate fluoro or chloro.

The term "fluoroalkyl" as used herein refers to an alkyl group as defined herein which is substituted one or more times with one or more fluorohalo, preferably perfluorated. The term "perfluoroalkyl" as used herein refers to an alkyl group as defined herein wherein all hydrogen atoms are replaced by fluoro atoms. Preferred fluoroalkyl groups include trifluoromethyl, pentafluoroethyl, etc.

The term "alkoxy" as used herein refers to an "alkyl-O—" group, wherein alkyl is as defined above.

The term "hydroxyalkyl" as used herein refers to an alkyl group (as defined hereinabove), which alkyl group is substituted one or more times with hydroxy. Examples of hydroxyalkyl groups include HO—$CH_2$—, HO—$CH_2$—$CH_2$— and $CH_3$—CH(OH)—.

The term "oxy" as used herein refers to an "—O—" group.

The term "oxo" as used herein refers to an "=O" group.

The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "carbamoyl" as used herein refers to a "$H_2N$(C=O)—" group.

The term "aryl", as used herein, unless otherwise indicated, includes carbocyclic aromatic ring systems derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, biphenyl, indenyl, naphthyl, anthracenyl, phenanthrenyl, pentalenyl, azulenyl, and biphenylenyl. Preferred "aryl" is phenyl, naphthyl or indanyl, in particular phenyl, unless otherwise stated. Any aryl used may be optionally substituted. Correspondingly, the term "arylene" means the corresponding biradical (-aryl-).

The term "heteroaryl", as used herein, refers to aromatic groups containing one or more heteroatoms selected from O, S, and N, preferably from one to four heteroatoms, and more preferably from one to three heteroatoms. Heteroaryl furthermore includes bi-, tri- and polycyclic groups, wherein at least one ring of the group is aromatic, and at least one of the rings contains a heteroatom selected from O, S, and N. Heteroaryl also include ring systems substituted with one or more oxo moieties. Examples of preferred heteroaryl moieties include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, phteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, azaindolyl, pyrazolinyl, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-).

The term "heterocyclyl" as used herein, refers to cyclic non-aromatic groups containing one or more heteroatoms selected from O, S, and N, preferably from one to four heteroatoms, and more preferably from one to three heteroatoms. Heterocyclyl furthermore includes bi-, tri- and polycyclic non-aromatic groups, and at least one of the rings contains a heteroatom selected from O, S, and N. Heterocyclyl also include ring systems substituted with one or more oxo moieties. Examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholinyl, thiomorpholinyl, 1,4-oxathianyl, benzofuranyl, isobenzofuranyl, indazolyl, benzimidazolyl, quinolinyl, isoquinolinyl, chromayl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocyclylene" means the corresponding biradical (-heterocyclyl-).

The term "N-heterocyclic ring" as used herein, refers to a heterocyclyl or a heteroaryl as defined hereinabove having at least one nitrogen atom, and being bound via a nitrogen atom. Examples of such N-heterocyclic rings are pyrrolidinyl, pyrrolyl, 3H-pyrrolyl, pyrazolyl, pyrazolidinyl, imidazolyl, imidazolidinyl, 3H-pyrazolyl, 1,2-oxazolyl, 1,2-thiazolyl, 1,3-thiazolyl, piperidinyl, pyridinyl, pyridazinyl, pyrazinyl, piperazinyl, morpholinyl, pyridinyl, pyridazinyl, pyrimidinyl, pyrazolyl, pyrazinyl, tetrazolyl, etc.

Isomers

The compounds of Formula (I) may exist as geometric isomers (i.e. cis-trans isomers), optical isomers or stereoisomers, such as diastereomers, as well as tautomers. Accordingly, it should be understood that the definition of compounds of Formula (I) includes each and every individual isomers corresponding to the structural formula: Formula (I), including cis-trans isomers, stereoisomers and tautomers, as well as racemic mixtures of these and pharmaceutically acceptable salts thereof. Hence, the definition of compounds of Formula (I) is also intended to encompass all R- and S-isomers of a chemical structure in any ratio, e.g. with enrichment (i.e. enantiomeric excess or diastereomeric excess) of one of the possible isomers and corresponding smaller ratios of other isomers.

Diastereoisomers, i.e. non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula (I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula (I) can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

Pharmaceutically Acceptable Salts

The compound of Formula (I) may be provided in any form suitable for the intended administration, in particular including pharmaceutically acceptable salts, solvates and prodrugs of the compound of Formula (I).

Pharmaceutically acceptable salts refer to salts of the compounds of Formula (I), which are considered to be acceptable for clinical and/or veterinary use. Typical pharmaceutically acceptable salts include those salts prepared by reaction of the compounds of Formula (I) a mineral or organic acid or an organic or inorganic base. Such salts are known as acid addition salts and base addition salts, respectively. It will be recognized that the particular counter-ion forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology.

Examples of pharmaceutically acceptable addition salts include acid addition salts formed with inorganic acids e.g. hydrochloric, hydrobromic, sulfuric, nitric, hydroiodic, metaphosphoric, or phosphoric acid; and organic acids e.g. succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts.

Solvates

The compound of Formula (I) may be provided in dissoluble or indissoluble forms together with a pharmaceutically acceptable solvent such as water, ethanol, and the like. Dissoluble forms may also include hydrated forms such as the mono-hydrate, the dihydrate, the hemihydrate, the trihydrate, the tetrahydrate, and the like.

Prodrugs

The compound of Formula (I) may be provided as a prodrug. The term "prodrug" used herein is intended to mean a compound which—upon exposure to certain physiological conditions—will liberate the compound of Formula (I) which then will be able to exhibit the desired biological action. A typical example is a labile ester of a carboxylic acid, in particular the pyridine carboxylic acid group of the compound of formula (I), which e.g. is capable of liberating the latent carboxylic acid group.

Illustrative examples of esters of a carboxylic acid group (in particular the pyridine carboxylic acid) are C1-6 alkyl esters, e.g. methyl esters, ethyl esters, 2-propyl esters, phenyl esters, 2-aminoethyl esters, etc., including (5-methyl-2-oxo-2H-1,3-dioxol-4-yl)methyl esters, 4-methoxyphenyl esters, 2-(ethoxycarbonyl)phenyl esters, {4-[(ethoxycarbonyl)(methyl)amino]phenyl}methyl esters, 2-(dimethylamino)ethyl esters, 3-(dimethylamino)propyl esters, [(ethoxycarbonyl)amino]phenylmethyl esters, 2,6-dimethoxyphenyl esters, 2,6-dimethylphenyl esters, 4-tert-butylphenyl esters, 4-oxopentan-2-yl esters, 4-(trifluoroacetamido)butan-2-yl esters, 4-(2,2,2-trifluoro-N-methylacetamido)butan-2-yl esters, 5-(trifluoroacetamido)pent-1-en-3-yl esters, 5-(2,2,2-trifluoro-N-methylacetamido)pent-1-en-3-yl esters, 1,3-bis(hexadecanoyloxy)propan-2-yl esters, 2,3-bis(hexadecanoyloxy)propyl esters, 4-oxo-4-(propan-2-yloxy)-1-(trifluoroacetamido)butan-2-yl esters, 1-oxo-1-(propan-2-yloxy)-5-(trifluoroacetamido)pentan-3-yl esters 2,2,2-trifluoethyl esters, 2,6-bis(propan-2-yloxy)phenyl esters, 2-fluoroethyl esters, 2,2-difluoroethyl esters, etc.

In particular, a prodrug according to the invention may be of the form

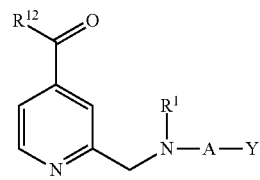

wherein $R^{12}$ is of the form $(R^{13})_2N—$ or of the form $R^{13}O—$, where each $R^{13}$ independently may be consistent with any of the examples of prodrugs given above or shown below. In particular, each $R^{13}$ independently may be selected from $C_{1-8}$ alkyl, $C_{2-8}$ alkenyl, $C_{2-8}$ alkynyl, $C_{3-10}$ cycloalkyl, and aryloxy which alkyl, alkenyl, alkynyl, cycloalkyl and aryloxy may be optionally substituted with one or more selected from —OH, aryl, $C_{1-6}$ alkoxy, heteroaryl, aryloxy, heteroaryloxy, F, a sulphonamide moiety, and $C_{3-6}$ cycloalkyl; and one $R^{13}$ in $(R^{13})_2N—$ may be, and preferably is, —H.

Methods for the Preparation of Compounds of Formula (I)

The compounds of Formula (I) as defined herein may be prepared by conventional methods of chemical synthesis, e.g. those described in the working examples, and starting from readily available starting materials. The starting materials for the processes described in the present application are known or may readily be prepared by conventional methods from commercially available chemicals.

The final products of the reactions described herein may be isolated by conventional techniques, e.g. by extraction, crystallisation, distillation, chromatography, etc.

In the following are described some of the possible routes to the compounds of Formula (I).

The compounds of the Formula (I) may be prepared as described in the following. Useful steps that may be used in the preparation steps of the compounds will be known to the skilled person. The methods below are given as non-limiting examples on how the compounds may be prepared.

Method A through C show the preparation of the compounds of this invention. Useful methods for the generation of intermediates are described afterwards.

Preparation of Compounds of Formula (I)

Scheme 1

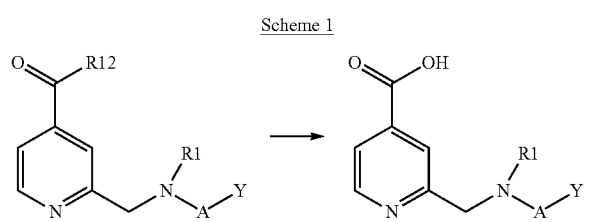

Method A

The compound of Formula (I) may be prepared according to Scheme 1 at room temperature, or by heating for up to several hours by use of a solvent such as DMSO, an alcohol, or tetrahydrofuran, and a base such as LiOH, KOH, or NaOH. A purification method such as silica gel chromatography is employed if needed.

Method B

The compound of Formula (I) may be prepared according to Scheme 1 at room temperature, or by heating for up to several hours by use of a solvent such as water, DMSO, an alcohol, or tetrahydrofuran, and an aqueous acid. A purification method such as silica gel chromatography is employed if needed.

Scheme 2

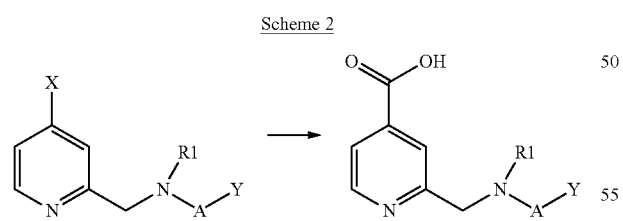

Method C

The compound of Formula (I) may be prepared from halides or triflates (X=halogen, OTf) according to Scheme 2 either at room temperature or by heating for up to several hours by use of a solvent such as toluene or tetrahydrofuran, a base such as cesium carbonate or potassium t-butoxide, a catalyst such as Pd complex optionally a salt such as lithium chloride and carbon monoxide. A purification method such as silica gel chromatography is employed if needed.

Preparation of Intermediates for Compounds of Formula (I)

Scheme 3

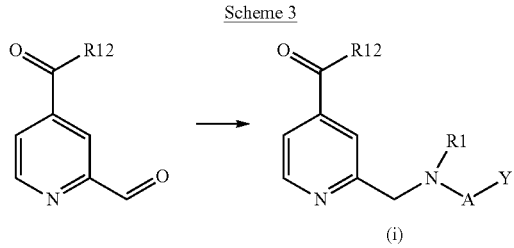

Method D

Intermediates (i) may be prepared from 2-formyl pyridines according to Scheme 3 in one-pot or by a stepwise procedure by mixing with an amine, optionally containing orthogonal protected reactive sites, and a reducing agent such as $NaBH_4$, $NaBH(OAc)_3$, $NaCNBH_3$, or $Et_3SiH$, either at room temperature or by heating for up to several hours by use of a solvent such as an alcohol, DCE, DCM, water, or toluene, optionally adding a catalyst such as an acid or a Lewis acid. Optionally, protecting groups may be removed and a purification method such as silica gel chromatography is employed if needed.

Scheme 4

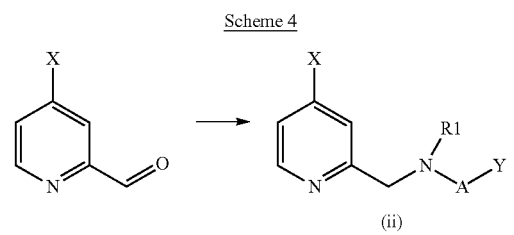

Method E

Intermediates (ii) may be prepared from 2-formyl pyridines according to Scheme 4 analogously to Method D.

Scheme 5

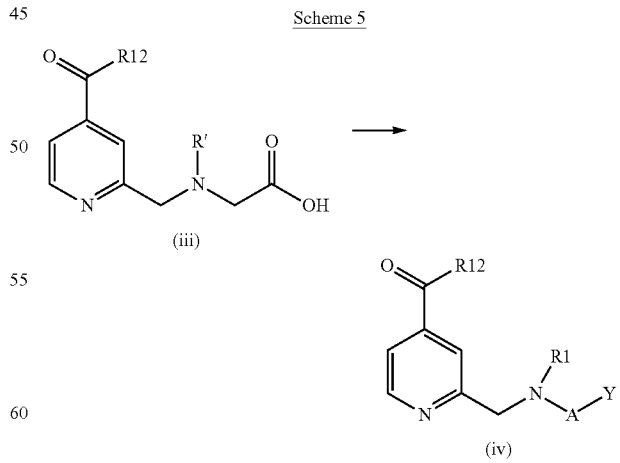

Method F

Intermediates (iv) be prepared from (iii) according to scheme 5, where R' is a suitable protecting group or R1, by use of a solvent such as DMF or THF, a base such as a

Scheme 6

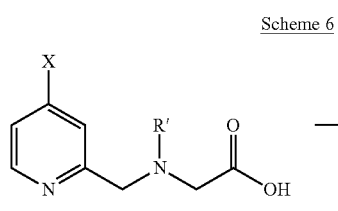

Method G

Intermediates (vi) may be prepared from (v) according to Scheme 6 analogously to Method F.

Scheme 7

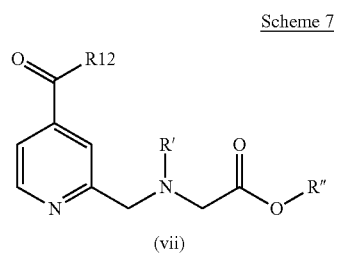

Method H

Intermediates (viii) be prepared according to scheme 7 from (vii), where R' is a suitable protecting group or R1 and R" is an orthogonal protecting group, which may be selectively removed, such as removal of R": $^t$Bu in presence of R': $CF_3CO$ by treating with trifluoroacetic acid in a solvent such as dichloromethane at room temperature for several hours. A purification method such as silica gel chromatography is employed if needed.

Scheme 8

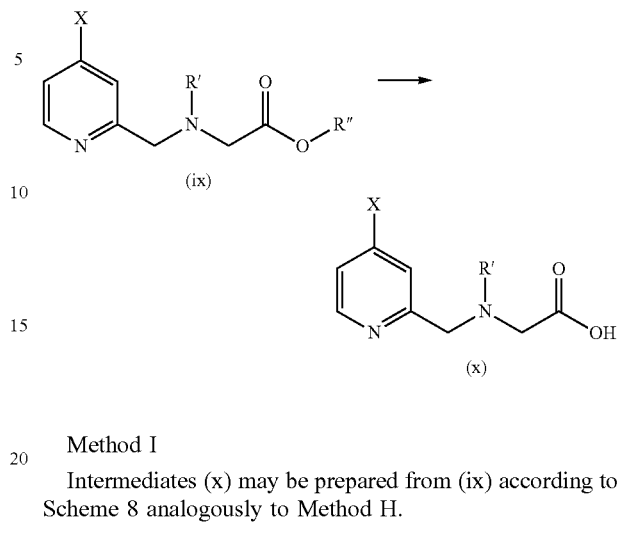

Method I

Intermediates (x) may be prepared from (ix) according to Scheme 8 analogously to Method H.

Scheme 9

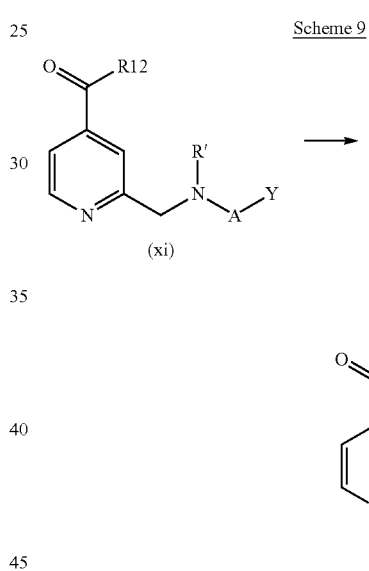

Method J

Intermediates (xii) may be prepared from aldehydes and intermediates (xi) according to Scheme 9 in one-pot or by a stepwise procedure by mixing with the amine (R': R1 or a suitable protecting group) and a reducing agent such as NaBH4, NaBH(OAc)$_3$, NaCNBH$_3$, or Et$_3$SiH, either at room temperature or by heating for up to several hours by use of a solvent such as an alcohol, DCE, DCM, water, or toluene, optionally adding a catalyst such as an acid or a Lewis acid. Optionally, protecting groups may be removed and a purification method such as silica gel chromatography is employed if needed.

Method K

Intermediates (xii) may be prepared from (xi) according to Scheme 9 by use of a solvent such as DMF or THF, optionally a base, and a suitable electrophilic species such as an epoxide, an aliphatic, allylic or benzylic bromide, chloride, or sulfonate. A purification method such as silica gel chromatography is employed if needed.

Scheme 10

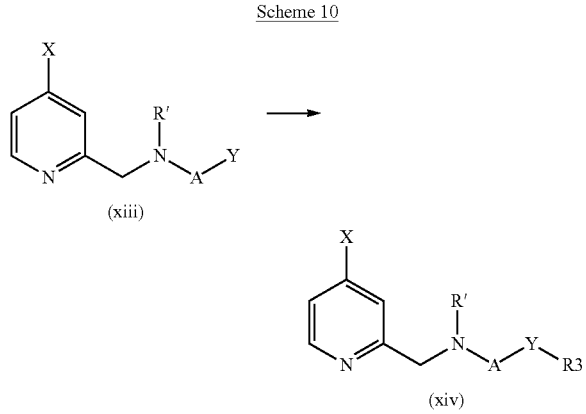

Method L

Intermediates (xiv) may be prepared from (xiii) according to Scheme 10 analogously to Method J.

Method M

Intermediates (xiv) may be prepared from (xiii) according to Scheme 10 analogously to Method K.

Scheme 11

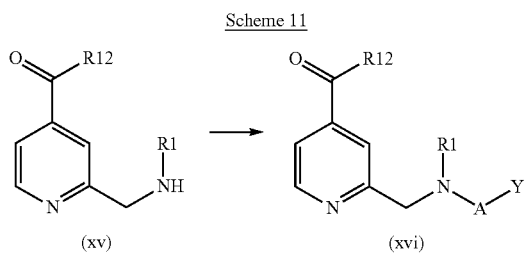

Method N

Intermediates (xvi) may be prepared from intermediates (xv) according to Scheme 11 in one-pot or by a stepwise procedure by mixing with an amine, optionally containing orthogonal protected reactive sites, and a reducing agent such as $NaBH_4$, $NaBH(OAc)_3$, $NaCNBH_3$, or $Et_3SiH$, either at room temperature or by heating for up to several hours by use of a solvent such as an alcohol, DCE, DCM, water, or toluene, optionally adding a catalyst such as an acid or a Lewis acid. Optionally, protecting groups may be removed and a purification method such as silica gel chromatography is employed if needed.

Scheme 12

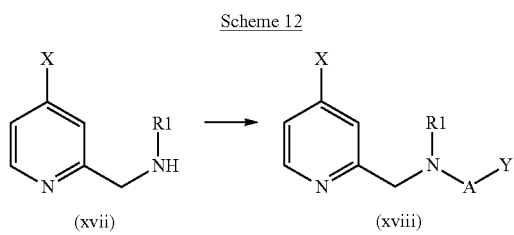

Method O

Intermediates (xviii) may be prepared from intermediates (xvii) according to Scheme 12 analogously to Method N.

Inhibitory Effect

The inventors have surprisingly found that compounds of Formula (I) as defined herein have an inhibitory effect on the activity of one or more HDMEs. In this respect said one or more HDMEs may be any HDME, however preferably the one or more HDMEs are selected from the JmjC (Jumonji) family, more preferably said one or more HDME(s) are HDME of the human JmjC family and even more preferably are HDME belonging to the KDM6, KDM5, KDM4 or KDM2 families. The present invention also relates to a compound of Formula (I) as defined herein in a method for inhibiting HDMEs. The method includes contacting a cell with a compound of Formula (I). In a related embodiment, the method further provides that the compound is present in an amount effective to produce a concentration sufficient to inhibit the demethylation of a histone in the cell.

Thus, preferably in an assay for demethylation of a histone substrate by said HDME, then preferred compounds of Formula (I) are compounds capable of reducing or preferably inhibiting said demethylation by said HDME. Said histone substrate may be any histone, but preferably is histone H3 or a fragment thereof, even more preferred: a fragment comprising K4, K9, K27, or K36 of H3. Preferably, said inhibition is determined as the $IC_{50}$ of said compound of Formula (I) in respect of the said demethylation assay.

Preferred compounds of Formula (I) which have an $IC_{50}$ at or below 1 µM, more preferably less than 300 nM, for example less than 100 nM, such as less than 50 nM in respect of demethylation of any of said histone substrates by any of said HDME. Thus very preferred compounds of Formula (I) which have an $IC_{50}$ at or below 1 µM, more preferably less than 500 nM, for example less than 100 nM, such as less than 50 nM in respect of demethylation of histone H3 methylated at least on one lysine.

In a preferred embodiment $IC_{50}$ is determined as described in Example 2 herein below. Thus, particularly preferred are compounds of Formula (I) which have an $IC_{50}$ at or below 1 µM, more preferably less than 500 nM, for example less than 100 nM, such as less than 50 nM when said $IC_{50}$ is determined as described in and one of the Examples herein below.

Particularly preferred compounds of Formula (I) are compounds that lead to a decreased tumour size and/or decreased number of metastases when tested in a xenograft model (Morton and Houghton, Nature Protocols, 2 (2) 247-250, 2007).

Pharmaceutical Compositions

In one aspect of this invention, there is provided a pharmaceutical composition comprising at, as an active ingredient, at least one compound of Formula (I) as defined herein and optionally one or more pharmaceutically acceptable excipients, diluents and/or carriers. The compounds of Formula (I) may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

The pharmaceutical compositions formed by combining a compound of Formula (I) as defined herein with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of Formula (I) as defined herein may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum, sodium starch glycolate, crospovidone, croscarmellose sodium or the like. Additional excipients for capsules include macrogols or lipids.

For the preparation of solid compositions such as tablets, the active compound of Formula (I) is mixed with one or more excipients, such as the ones described above, and other pharmaceutical diluents such as water to make a solid pre-formulation composition containing a homogenous mixture of a compound of Formula (I). The term "homogenous" is understood to mean that the compound of Formula (I) is dispersed evenly throughout the composition so that the composition may readily be subdivided into equally effective unit dosage forms such as tablets or capsules.

Liquid compositions for either oral or parenteral administration of the compound of Formula (I) include, e.g., aqueous solutions, syrups, elixirs, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. For parenteral administration, solutions containing a compound of Formula (I) in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

The preparation of all these solutions under sterile conditions is readily accomplished by standard pharmaceutical techniques well known to those skilled in the art.

Depot injectable compositions are also contemplated as being within the scope of the present invention.

In addition to the aforementioned ingredients, the compositions of a compound of Formula (I) may include one or more additional ingredients such as diluents, buffers, flavouring agents, colourant, surface active agents, thickeners, preservatives, e.g. methyl hydroxybenzoate (including antioxidants), emulsifying agents and the like.

A suitable dosage of the compound of Formula (I) will depend on the age and condition of the patient, the severity of the disease to be treated and other factors well known to the practicing physician. The compound may be administered for example either orally, parenterally or topically according to different dosing schedules, e.g. daily or with intervals, such as weekly intervals. In general a single dose will be in the range from 0.01 to 100 mg/kg body weight, preferably from about 0.05 to 75 mg/kg body weight, more preferably between 0.1 to 50 mg/kg body weight, and most preferably between 0.1 to 25 mg/kg body weight. The compound may be administered as a bolus (i.e. the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

The compounds of Formula (I) may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances, or preferably an active substance as described in the section "combination treatment" herein below.

Clinical Conditions and Other Uses of Compounds

The compounds according to Formula (I) as defined herein are useful for treatment of a HDME dependent disease, disorder or condition. The treatment may include administering to a mammal, preferably a human, more preferably a human suffering from a HDME dependent disease, a therapeutically effective amount of a compound according to Formula (I) as defined herein.

Said HDME may be any HDME, however preferably the HDME of the present method is selected from the JmjC (Jumonji) family, as described in Cloos et. al., Genes & Development 22, 1115-1140, 2008. More preferably said HDME is a HDME of the human JmjC family.

The present invention also relates to a compound of Formula (I) as defined herein for use in the treatment of a HDME dependent disease, such as for the treatment of cancer.

By the term "HDME dependent disease" is meant any disease characterized by elevated HDME expression and/or activity in at least in some instances of the disease, or a disease which is ameliorated by lowering the activity of HDMEs. Thus, the disease to be treated with the inhibitors of HDME, i.e. compounds of Formula (I), may be a proliferative or hyperproliferative disease, which includes benign or malignant tumors, for example a proliferative or hyperproliferative disease selected from the group consisting of a carcinoma of the brain, kidney, liver, adrenal gland, bladder, breast, stomach (for example gastric tumors), ovaries, esophagus, colon, rectum, prostate, pancreas, lung, vagina, thyroid, sarcoma, glioblastomas, multiple myeloma or gastrointestinal cancer, for example, colon carcinoma or colorectal adenoma, or a tumor of the neck and head, an epidermal hyperproliferation, for example, psoriasis, prostate hyperplasia, a neoplasia, including a neoplasia of epithelial character, including mammary carcinoma, and a leukemia.

In one embodiment, compounds of Formula (I) as defined herein are useful in the treatment of one or more cancers. The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma, (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcfnoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcorna, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (acute myeloid leukemia, chronic myeloid leukemia, acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

In one embodiment, the compounds of Formula (I) as defined herein are useful in the treatment of one or more cancers selected from the group consisting of: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In another very preferred embodiment, the compound of Formula (I) as defined herein are useful for the treatment of squamous cell carcinomas. Preferably said squamous cell carcinomas are cancers of the carcinoma type of squamous epithelium that may occur in many different organs, including the skin, lips, mouth, esophagus, urinary bladder, prostate, lungs, vagina, and cervix; brain cancer, that is neuroblastoma, glioblastoma and other malignant and benign brain tumors; breast cancer, pancreatic cancer, and multiple myeloma.

In yet another embodiment, the compounds of Formula (I) as defined herein are useful for treatment of brain cancer, tumors of adults such as head and neck cancers (e.g., oral, laryngeal and esophageal), genito urinary cancers (e.g., prostate, bladder, renal, uterine, ovarian, testicular, rectal and colon), and breast cancer.

Other cancer forms for which the compounds of Formula (I) are useful as treatment can be found in Stedman's Medical Dictionary (Lippincott Williams & Wilkins, 28$^{th}$ Ed., 2005), which is incorporated herein by reference in its entirety.

In still another related embodiment, the disease to be treated by compounds of Formula (I) as defined herein is selected from persistent proliferative or hyperproliferative conditions such as angiogenesis, such as psoriasis; Kaposi's sarcoma; restenosis, e.g., stent-induced restenosis; endometriosis; Hodgkin's disease; leukemia; hemangioma; angiofibroma; eye diseases, such as neovascular glaucoma; renal diseases, such as glomerulonephritis; malignant nephrosclerosis; thrombotic microangiopathic syndromes; transplant rejections and glomerulopathy; fibrotic diseases, such as cirrhosis of the liver; mesangial cell-proliferative diseases; injuries of the nerve tissue; and inhibiting the re-occlusion of vessels after balloon catheter treatment, for use in vascular prosthetics or after inserting mechanical devices for holding vessels open, such as, e.g., stents, as immune-suppressants, as an aid in scar-free wound healing, and treating age spots and contact dermatitis.

The compounds of Formula (I) are suitable as active agents in pharmaceutical compositions that are efficacious particularly for treating cellular proliferative or hyperproliferative ailments and/or ailments associated with dysregulated gene expression. Such pharmaceutical compositions have a therapeutically effective amount of the compound of Formula (I) along with other pharmaceutically acceptable excipients, carriers, and diluents and. The phrase, "therapeutically effective amount" as used herein indicates an amount necessary to administer to a host, or to a cell, tissue, or organ of a host, to achieve a therapeutic effect, such as an ameliorating or alternatively a curative effect, for example an anti-tumor effect, e.g. reduction of or preferably inhibition of proliferation of malignant cancer cells, benign tumor cells or other proliferative cells, or of any other HDME dependent disease.

Another aspect of the invention is a pharmaceutical composition comprising a therapeutically effective amount of at least one compound of Formula (I) as defined herein, or a pharmaceutically acceptable salt, solvate or prodrug thereof, in combination with at least one further anti-neoplastic compound, and a pharmaceutically acceptable excipient, carrier or diluent.

Method of Treatment

In a further aspect the present invention relates to a method of treating a diseases in a subject, said method comprises administering to said subject a therapeutically effective amount of at least one compound of Formula (I) as defined herein. The disease may be any disease or disorder as mentioned herein, such as for example mentioned in the section "HDME dependent diseases", and the compound may be administered alone or in a pharmaceutical composition, such as for example mentioned in the section "Pharmaceutical compositions".

Hence, the invention also relates to a compound of Formula (I) as defined herein for use as a medicament.

The term "treating" and "treatment", as used herein, unless otherwise indicated, refers to reversing, alleviating, inhibiting the process of, or preventing the disease, disorder or condition to which such term applies, or one or more symptoms of such disease, disorder or condition and includes the administration of a compound of Formula (I) to prevent the onset of the symptoms or the complications, or alleviating the symptoms or the complications, or eliminating the disease, condition, or disorder. Preferably treatment is curative or ameliorating.

In a preferred embodiment of this aspect of the invention the method is a method of treating a HDME dependent disease in a subject, said method comprises administering to said subject a therapeutically effective amount of a compound of Formula (I) as defined herein to a subject in need of such treatment. The HDME dependent disease may be any HDME dependent disease as described herein above. Preferably the HDME dependent disease is squamous cell carcinomas or any other of the cancer conditions mentioned above.

Hence, the invention also relates to a compound of Formula (I) as defined herein for use in the treatment of a HDME dependent disease, such as for the treatment of cancer.

Further, the invention relates to the use of a compound of Formula (I) as defined herein for the preparation of a pharmaceutical composition for the treatment of a HDME dependent disease.

In one embodiment of the method of treatment of a HDME dependent disease, the compound of Formula (I) as defined herein is administered in combination with one or more further active substances. The active substances may be any active substances, and preferably an active substance as described herein above in the section "combination treatment". More preferably the one or more additional active substances are selected from the group consisting of anti-proliferative or anti-neoplastic agents.

Combination Treatment

A compound of Formula (I) may also be used to advantage in combination with one or more other anti-proliferative or anti-neoplastic agents. Such anti-proliferative agents include, but are not limited to other HDME inhibitors, proteasome inhibitors, including bortezomib (Valcade) and Carfilzomib, aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; angiostatic steroids; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMOD AL®); leucovorin; immune stimulating agents, such as BCG, IL-2 or IFN-α, antibodies, such as rituximab or herceptin and cancer vaccines.

A compound of Formula (I) as defined herein may also be used to advantage in combination with known therapeutic processes, e.g., the administration of hormones or tumor cell damaging approaches, especially ionizing radiation.

A compound of Formula (I) as defined herein may also be used as a radiosensitizer, including, for example, the treatment of tumors which exhibit poor sensitivity to radiotherapy.

By the term "combination", is meant either a fixed combination in one dosage unit form, or a kit of parts for the combined administration where a compound of Formula (I) and a combination partner may be administered independently at the same time or separately within time intervals that especially allow that the combination partners show a cooperative, e.g., synergistic, effect, or any combination thereof.

The phrase, "aromatase inhibitor" as used herein relates to a compound which inhibits the estrogen production, i.e., the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LEN- TARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "antiestrogen" as used herein relates to a compound that antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen" as used herein relates to any substance which is capable of inhibiting the biological effects of androgenic hormones and includes, but is not limited to, bicalutamide (CASODEX), which can be formulated, e.g., as disclosed in U.S. Pat. No. 4,636,505.

The phrase, "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The phrase, "topoisomerase I inhibitor" as used herein includes, but is not limited to topotecan, gimatecan, irinotecan, camptothecan and its analogues, 9-nitrocamptothecin and the macromolecular camptothecin conjugate PNU-166148 (compound AI in WO99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The phrase, "topoisomerase II inhibitor" as used herein includes, but is not limited to the anthracyclines such as doxorubicin (including liposomal formulation, e.g., CAELYX), daunorubicin, epirubicin, idarubicin and nemorubicin, the anthraquinones mitoxantrone and losoxantrone, and the podophyllotoxins etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The phrase, "microtubule active agent" relates to microtubule stabilizing, microtubule destabilizing agents and microtublin polymerization inhibitors including, but not limited to taxanes, e.g., paclitaxel and docetaxel, vinca alkaloids, e.g., vinblastine, including vinblastine sulfate, vincristine including vincristine sulfate, and vinorelbine, discodermolides, cochicine and epothilones and derivatives thereof, e.g., epothilone B or D or derivatives thereof. Paclitaxel may be administered e.g., in the fo[pi]n as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Included are Epothilone A and/or B.

The phrase, "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The phrase, "histone deacetylase inhibitors" or "HDAC inhibitors" relates to compounds which inhibit at least one example of the class of enzymes known as a histone deacetylase, and which compounds generally possess antiproliferative activity. Previously disclosed HDAC inhibitors include compounds disclosed in, e.g., WO 02/22577, including N-hydroxy-3-[4-{[(2-hydroxyethyl)[2-(IH-indol-3-yl) ethyl]-amino]methyl]phenyl]-2E-2-propenamide, N-hydroxy-3-[4-[[[2-(2-methyl-IH-indol-3-yl)-ethylJ-amino] methyl]phenyl]-2E-2-propenamide and pharmaceutically acceptable salts thereof. It further includes Suberoylanilide hydroxamic acid (SAHA). Other publicly disclosed HDAC inhibitors include butyric acid and its derivatives, including sodium phenylbutyrate, thalidomide, trichostatin A and trapoxin.

The term "antineoplastic antimetabolite" includes, but is not limited to, 5-Fluorouracil or 5-FU, capecitabine, gemcitabine, DNA demethylating agents, such as 5-azacytidine and decitabine, methotrexate and edatrexate, and folic acid antagonists such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The phrase, "platin compound" as used herein includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

Tumor cell damaging approaches refer to approaches such as ionizing radiation. The phrase, "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See, e.g., Hellman, Principles of Radiation Therapy, Cancer, in Principles and Practice of Oncology, Devita et al., Eds., 4th Edition, Vol. 1, pp. 248-275 (1993).

The phrase, "angiostatic steroids" as used herein refers to agents which block or inhibit angiogenesis, such as, e.g., anecortave, triamcinolone, hydrocortisone, 11-[alpha]-epi-hydrocotisol, cortexolone, 17[alpha]-hydroxyprogesterone, corticosterone, desoxycorticosterone, testosterone, estrone and dexamethasone.

Other chemotherapeutic agents include, but are not limited to, plant alkaloids, hormonal agents and antagonists; biological response modifiers, preferably lymphokines or interferons; antisense oligonucleotides or oligonucleotide derivatives; or miscellaneous agents or agents with other or unknown mechanism of action.

The structure of the active agents identified by code numbers, generic or trade names may be taken from the actual edition of the standard compendium "The Merck Index" or from databases, e.g., Patents International (e.g., IMS World Publications).

The above-mentioned compounds, which can be used in combination with a compound of Formula (I), can be prepared and administered as described in the art such as in the documents cited above.

Furthermore, the compounds of the invention may be used in a method of profiling the functional and structural similarity of histone demethylases comprising taking a panel of at least two histone demethylases and a panel of at least two compounds of formula 1 and determining the extent to which each said compound of formula 1 inhibits the activity of each of said histone demethylases, and generating a similarity index reflecting the degree of similarity between the histone demethylases in respect of their inhibition by said compounds.

EXAMPLES

Example 1: Examples of Compounds of Formula (I)

General Methods and Materials

Table 1 below shows examples of compounds according to the invention and indicates routes that may be employed in their synthesis. All chemicals were purchased from Sigma-Aldrich, Alfa Aesar, Matrix, Combiblock, Oakwood, and Chembridge. Anhydrous solvents were Aldrich Sure/Seal™ brand. All reactions were carried out under a dry nitrogen atmosphere using dry solvents. Reactions were monitored by thin-layer chromatography carried out on Sigma-Aldrich 0.25 mm silica gel plates (60 Å, fluorescent indicator). Spots were visualized under UV light (254 nm). Flash column chromatography was performed on Biotage SNAP Flash System, or silica gel 60 (particle size 0.032-0.063 mm) obtained from Silicycle, Inc. Low-resolution ES (electrospray) mass spectra were obtained using a Micromass Quattro Ultima mass spectrometer in the electrospray positive (ES+) or negative (ES−) ion mode. 1H-NMR spectra were recorded on a Bruker AM-300 spectrometer and were calibrated using residual nondeuterated solvent as internal reference. Spectra were processed using Spinworks version 2.5 (developed by Dr. Kirk Marat, Department of Chemistry, University of Manitoba). Preparative HPLC was performed on Waters 2996 with Photodiode Array Detector, Waters 600 Controller, Waters 100 pump, and Waters 717 auto sampler, with UV detection at 254 and 280 nm. Flow rate: 15 mL/minute, run time 30 minutes. Solvents: 0-100% ($H_2O$-MeOH), with and without added TFA (0.1%). Column used was Supelco C18, 25 cm×21.2 mm, particle size 10 micrometer.

Ethyl 2-formylpyridine-4-carboxylate was prepared analogously to Queguiner, G. and Pastour, P. (Comptes Rendus des Seances de l'Academie des Sciences, Serie C: Sciences Chimiques (1969), 268(2), 182-5).

TABLE 1

| Structure | # | Name | Synthetic Route | NMR |
|---|---|---|---|---|
| 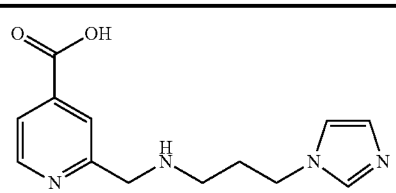 | 1 | 2-({[3-(1H-imidazol-1-yl)propyl]amino}methyl)pyridine-4-carboxylic acid | A | $^1$H NMR (300 MHz, $CD_3OD$), δ ppm: 8.10 (s, 1H), 7.98 (dd, 1H), 7.80 (t, 1H), 7.65 (t, 1H), 4.58 (s, 2H), 4.50 (t, 2H). |
| 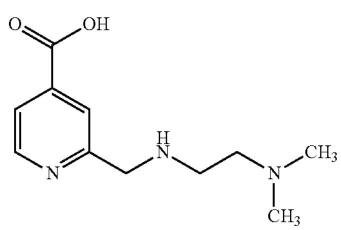 [SMILES: CN(C)CCNCc1cc(C(=O)O)ccn1] | 2 | 2-({[2-(dimethylamino)ethyl]amino}methyl)pyridine-4-carboxylic acid | A | $^1$H NMR (300 MHz, $CD_3OD$), δ ppm: 8.03 (s, 1H), 4.58 (s, 2H), 3.63 (m, 4H), 3.0 (s, 6H). |
| 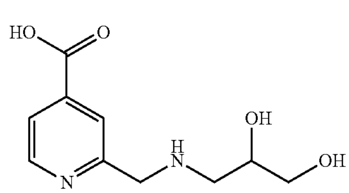 [SMILES: O=C(O)c1ccnc(CNCC(O)CO)c1] | 3 | 2-({[(2R)-2,3-dihydroxypropyl]amino}methyl)pyridine-4-carboxylic acid | A | $^1$H NMR (300 MHz, $CD_3OD$), δ ppm: 8.12 (s, 1H), 4.04 (m, 1H), 3.62 (m, 2H), 3.35 (m, 1H), 3.18 (dd, 1H). |

TABLE 1-continued

| Structure | # | Name | Synthetic Route | NMR |
|---|---|---|---|---|
| 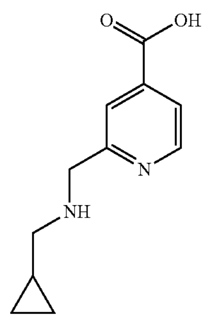 [SMILES: O=C(O)c1ccnc(CNCC2CC2)c1] | 4 | 2-{[(cyclopropyl-methyl)amino]methyl}pyridine-4-carboxylic add | A | $^1$H NMR (300 MHz, CD$_3$OD), δ ppm: 4.56 (s, 2H), 3.08 (d, 2H), 1.21 (m, 1H), 0.75 (m, 2H), 0.47 (m, 2H). |
| 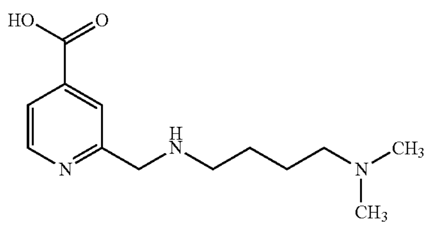 [SMILES: CN(C)CCCCNCc1cc(C(=O)O)ccn1] | 5 | 2-{[(cyclopropyl-methyl)amino]methyl}pyridine-4-carboxylic acid | A | $^1$H-NMR (300 MHz, CD$_3$OD), δ ppm: 8.0 (s, 1H), 4.42 (s, 2H), 2.80 (s, 6H). |
| 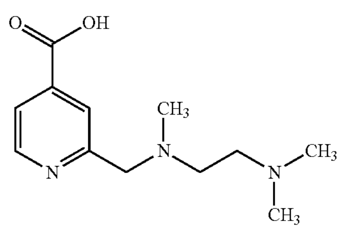 [SMILES: CN(C)CCN(C)Cc1cc(C(=O)O)ccn1] | 6 | 2-({[2-(dimethylamino)ethyl](methyl)amino}methyl)pyridine-4-carboxylic acid | A | $^1$H NMR (300 MHz, CD$_3$OD), δ ppm: 8.16 (s, 1H), 4.76 (s, 2H), 3.80 (s, 4H). |
| 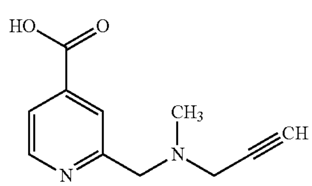 | 7 | 2-{[methyl(prop-2-yn-1-yl)amino]methyl}pyridine-4-carboxylic acid | A | $^1$H NMR (300 MHz, CD$_3$OD), δ ppm: 7.93 (s, 1H), 3.77 (s, 2H), 3.39 (s, 2H). |
| 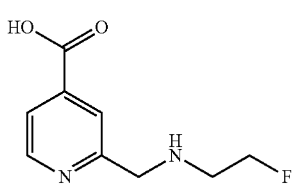 [SMILES: O=C(O)c1ccnc(CNCCF)c1] | 8 | 2-{[(2-fluoroethyl)amino]methyl}pyridine-4-carboxylic acid | A | $^1$H NMR (300 MHz, CD$_3$OD), δ ppm: 7.85 (s, 1H), 4.65 (t, 1H), 4.49 (t, 1H), 4.02 (s, 2H). |
| 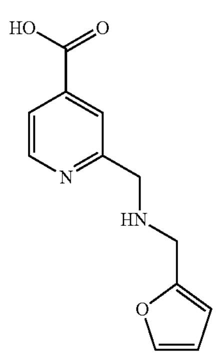 [SMILES: O=C(O)c1ccnc(CNCc2ccco2)c1] | 9 | 2-{[(furan-2-ylmethyl)amino]methyl}pyridine-4-carboxylic acid | A | $^1$H NMR (300 MHz, CD$_3$OD), δ ppm: 7.72 (s, 1H), 6.30 (d, 1H), 6.22 (d, 1H), 3.78 (s, 2H). |

TABLE 1-continued

| Structure | # | Name | Synthetic Route | NMR |
|---|---|---|---|---|
| 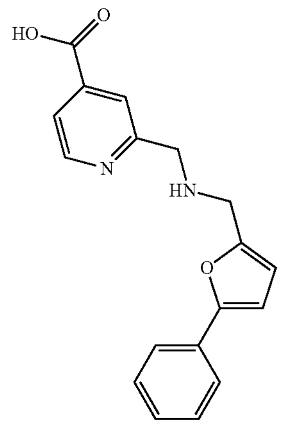 [SMILES: O=C(O)c1ccnc(CNCc2ccc(-c3ccccc3)o2)c1] | 10 | 2-({[(5-phenyl-furan-2-yl)methyl]amino}methyl)pyridine-4-carboxylic acid | A | ¹H NMR (300 MHz, CD₃OD), δ ppm: 7.75 (s, 1H), 6.68 (s, 1H), 6.38 (s, 1H), 3.85 (s, 2H). |
| 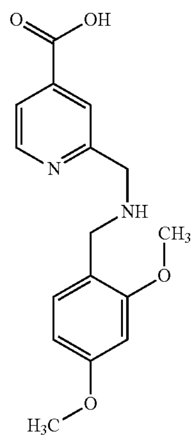 [SMILES: COc1ccc(CNCc2cc(C(=O)O)ccn2)c(OC)c1] | 11 | 2-({[(2,4-dimethoxyphenyl)methyl]amino}methyl)pyridine-4-carboxylic acid | A | ¹H NMR (300 MHz, CD₃OD), δ ppm: 7.84 (s, 1H), 7.15 (s, 1H), 3.85 (s, 2H), 3.70 (s, 2H). |
| 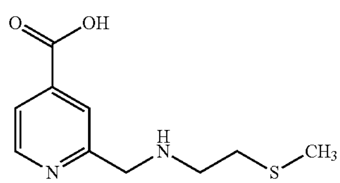 | 12 | 2-({[2-(methylsulfanyl)ethyl]amino}methyl)pyridine-4-carboxylic acid | A | ¹H NMR (300 MHz, CD₃OD), δ ppm: 7.85 (s, 1H), 3.96 (s, 2H), 2.82 (t, 2H), 2.67 (t, 2H). |
| 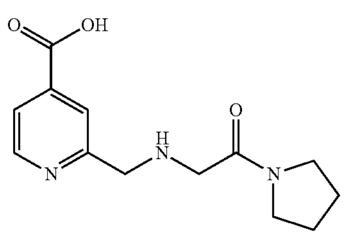 [SMILES: O=C(O)c1ccnc(CNCC(=O)N2CCCC2)c1] | 13 | 2-({[2-oxo-2-(pyrrolidin-1-yl)ethyl]amino}methyl)pyridine-4-carboxylic acid | B | ¹H-NMR (300 MHz, MeOH-d₄): δ ppm: 7.70 (s, 1H), 3.70 (s, 2H), 4.0 (s, 2H), 3.40 (m, 6H). |
| 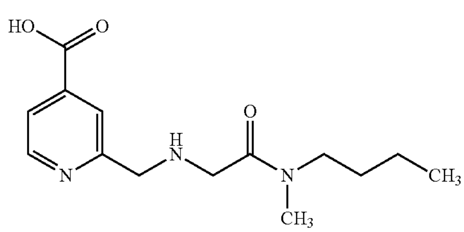 | 14 | 2-[({[butyl(methyl)carbamoyl]methyl}amino)methyl]pyridine-4-carboxylic acid | B | ¹H-NMR (300 MHz, MeOH-d₄), δ ppm: 7.7 (s, 1H), 3.7 (s, 2H), 3.4 (s, 2H) 3.2 (m, 2H). |

TABLE 1-continued

| Structure | # | Name | Synthetic Route | NMR |
|---|---|---|---|---|
| 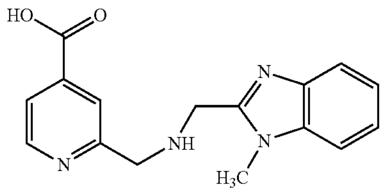 [SMILES: Cn1c(CNCc2cc(C(=O)O)ccn2)nc2ccccc21] | 15 | 2-({[(1-methyl-1H-1,3-benzodiazol-2-yl)methyl]amino}methyl)pyridine-4-carboxylic acid | A | ¹H NMR (300 MHz, CD₃OD), δ ppm: 7.84 (s, 1H), 4.16 (s, 2H), 4.02 (s, 2H), 3.90 (s, 3H). |
| 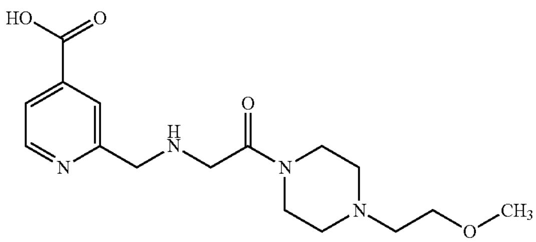 [SMILES: COCCN1CCN(C(=O)CNCc2cc(C(=O)O)ccn2)CC1] | 16 | 2-[({2-[4-(2-methoxyethyl)piperazin-1-yl]-2-oxoethyl}amino)methyl]pyridine-4-carboxylic acid | B | ¹H-NMR (300 MHz, MeOH-d₄), δ ppm: 7.7 (s, 1H), 3.7 (s, 2H), 3.3 (s, 3H), 1.8 (m, 8H). |
| 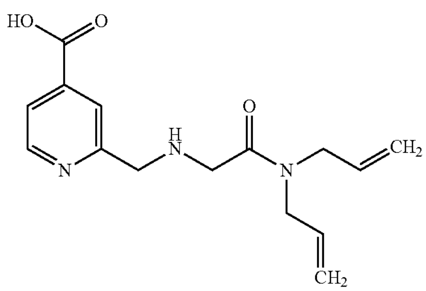 [SMILES: C=CCN(CC=C)C(=O)CNCc1cc(C(=O)O)ccn1] | 17 | 2-[({[bis(prop-2-en-1-yl)carbamoyl]methyl}amino)methyl]pyridine-4-carboxylic acid | B | ¹H-NMR (300 MHz, MeOH-d₄), δ ppm: 7.7 (s, 1H), 5.6 (m, 2H), 4.9 (m, 4H), 3.5 (s, 2H). |
| 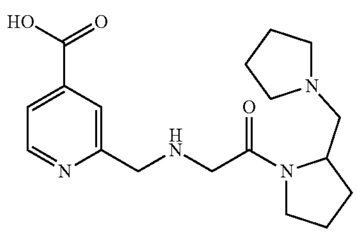 [SMILES: O=C(O)c1ccnc(CNCC(=O)N2CCCC2CN2CCCC2)c1] | 18 | 2-[({2-oxo-2-[(2R)-2-(pyrrolidin-1-ylmethyl)pyrrolidin-1-yl]ethyl}amino)methyl]pyridine-4-carboxylic acid | B | ¹H-NMR (300 MHz, MeOH-d₄), δ ppm: 7.7 (s, 1H), 4.2 (m, 1H), 3.4 (m, 6H), 3.0 (m, 1H). |
| 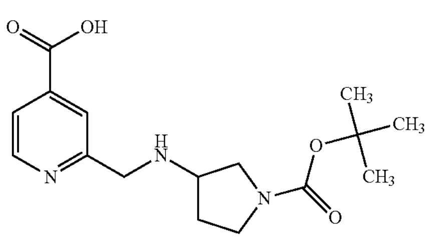 [SMILES: CC(C)(C)OC(=O)N1CCC(NCc2cc(C(=O)O)ccn2)C1] | 19 | 2-({[(3R)-1-[(tert-butoxy)carbonyl]pyrrolidin-3-yl]amino}methyl)pyridine-4-carboxylic acid | A | ¹H-NMR (300 MHz, MeOH-d₄), δ ppm: 7.75 (s, 1H), 3.85 (s, 1H), 1.50 (s, 9H). |
| 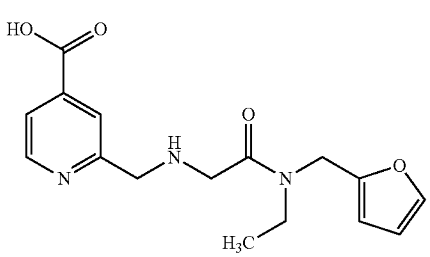 [SMILES: CCN(Cc1ccco1)C(=O)CNCc1cc(C(=O)O)ccn1] | 20 | 2-({[(3R)-1-((tert-butoxy)carbonyl]pyrrolidin-3-yl]amino}methyl)pyridine-4-carboxylic acid | B | ¹H NMR (300 MHz, CD₃OD), δ ppm: 7.72 (s, 1H), 6.32 (d, 1H), 6.20 (d, 1H), 4.00 (s, 2H), 3.84 (s, 2H). |

TABLE 1-continued

| Structure | # | Name | Synthetic Route | NMR |
|---|---|---|---|---|
| 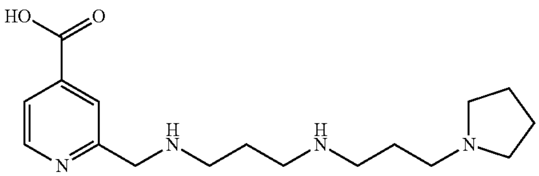 [SMILES: O=C(O)c1ccnc(CNCCCNCCCN2CCCC2)c1] | 21 | 2-{[(3-{[3-(pyrrolidin-1-yl)propyl]amino}propyl)amino]methyl}pyridine-4-carboxylic acid | C | ¹H NMR (300 MHz, D₂O), δ ppm: 7.96 (s, 1H), 4.48 (s, 2H), 2.92-3.25 (m, 8H). |
| 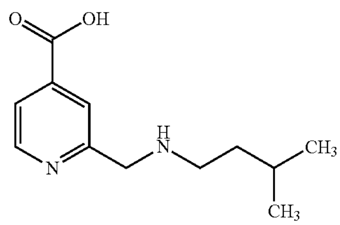 | 22 | 2-{[(3-methylbutyl)amino]methyl}pyridine-4-carboxylic acid | A | ¹H-NMR (300 MHz, CD₃OD), δ ppm: 7.80 (s, 1H), 3.90 (s, 2H), 2.60 (m, 2H), 0.92 (d, 6H). |
| 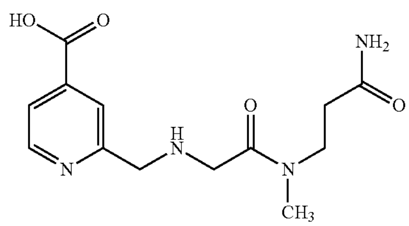 [SMILES: CN(CCC(N)=O)C(=O)CNCc1cc(C(=O)O)ccn1] | 23 | 2-[({[(2-carbamoylethyl)(methyl)carbamoyl]methyl}amino)methyl]pyridine-4-carboxylic acid | B | ¹H-NMR (300 MHz, MeOH-d₄), δ ppm: 7.9 (s, 1H), 3.8 (s, 2H), 3.5 (m, 4H), 2.3 (m, 2H). |
| 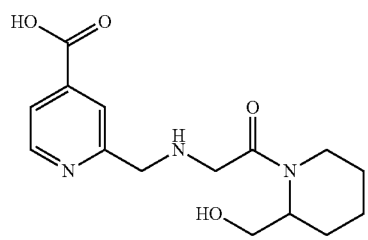 [SMILES: O=C(O)c1ccnc(CNCC(=O)N2CCCCC2CO)c1] | 24 | 2-[({2-[2-(hydroxymethyl)piperidin-1-yl]-2-oxoethyl}amino)methyl]pyridine-4-carboxylic acid | B | ¹H-NMR (300 MHz, MeOH-d₄), δ ppm: 7.9 (s, 1H), 3.9 (s, 2H), 3.5 (m, 2H). |
| 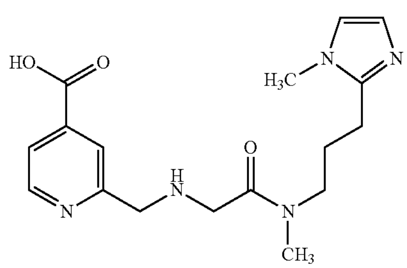 [SMILES: CN(CCCc1nccn1C)C(=O)CNCc1cc(C(=O)O)ccn1] | 25 | 2-{[({methyl[3-(1-methyl-1H-imidazol-2-yl)propyl]carbamoyl}methyl)amino]methyl}pyridine-4-carboxylic acid | B | ¹H-NMR (300 MHz, MeOH-d₄): δ 7.7 (s, 1H), 6.7 (d, 1H), 6.6 (d, 1H), 3.7 (s, 2H), 3.5 (s, 3H). |
| 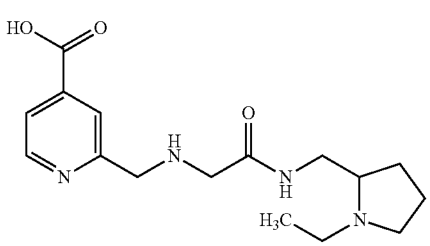 [SMILES: CCN1CCCC1CNC(=O)CNCc1cc(C(=O)O)ccn1] | 26 | 2-{[({[(1-ethylpyrrolidin-2-yl)methyl]carbamoyl}methyl)amino]methyl}pyridine-4-carboxylic acid | B | ¹H-NMR (300 MHz, MeOH-d₄), δ ppm: 7.7 (s, 1H), 3.7 (s, 2H), 3.4 (m, 2H), 3.3 (m, 3H), 1.0 (t, 3H). |

TABLE 1-continued

| Structure | # | Name | Synthetic Route | NMR |
|---|---|---|---|---|
| 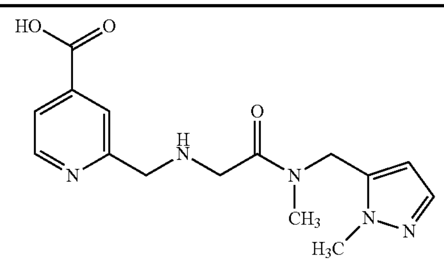 | 27 | 2-{[({methyl[(1-methyl-1H-pyrazol-5-yl)methyl]carbamoyl}methyl)amino]methyl}pyridine-4-carboxylic acid | B | $^1$H-NMR (300 MHz, MeOH-d$_4$), δ ppm: 7.7 (s, 1H), 7.6 (d, 1H), 7.3 (d, 1H), 6.3 (d, 1H), 4.6 (s, 2H), 4.0 (s, 2H). |
| 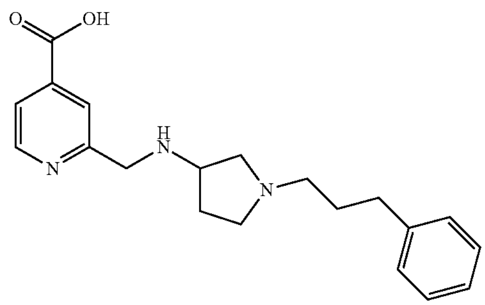 [SMILES: O=C(O)c1ccnc(CNC2CCN(CCCc3ccccc3)C2)c1] | 28 | 2-({[(3R)-1-(3-phenylpropyl)pyrrolidin-3-yl]amino}methyl)pyridine-4-carboxylic acid | D | $^1$H-NMR (300 MHz, MeOH-d$_4$), δ ppm: 7.80 (s, 1H), 7.20 (m, 5H), 3.85 (s, 2H). |
| 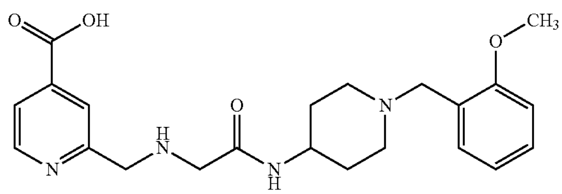 [SMILES: COc1ccccc1CN1CCC(NC(=O)CNCc2cc(C(=O)O)ccn2)CC1] | 29 | 2-({[({1-[(2-methoxyphenyl)methyl]piperidin-4-yl}carbamoyl)methyl]amino}methyl)pyridine-4-carboxylic acid | E | $^1$H-NMR (300 MHz, CD$_3$OD), δ ppm: 7.82 (s, 1H), 7.26 (m, 2H), 6.94 (m, 2H), 3.90 (s, 2H), 3.85 (s, 3H), 3.62 (s, 2H), 3.24 (s, 2H). |
| 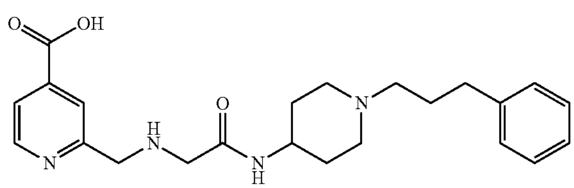 [SMILES: O=C(CNCc1cc(C(=O)O)ccn1)NC1CCN(CCCc2ccccc2)CC1] | 30 | 2-{[({[1-(3-phenylpropyl)piperidin-4-yl]carbamoyl}methyl)amino]methyl}pyridine-4-carboxylic acid | E | $^1$H-NMR (300 MHz, CD$_3$OD), δ ppm: 7.84 (s, 1H), 3.92 (s, 2H), 3.78 (m, 2H), 3.24 (s, 2H), 2.96 (m, 2H). |
| 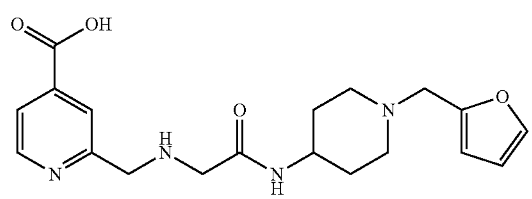 [SMILES: O=C(CNCc1cc(C(=O)O)ccn1)NC1CCN(Cc2ccco2)CC1] | 31 | 2-{[({[1-(furan-2-ylmethyl)piperidin-4-yl]carbamoyl}methyl)amino]methyl}pyridine-4-carboxylic acid | E | $^1$H-NMR (300 MHz, CD$_3$OD), δ ppm: 7.82 (s, 1H), 7.64 (d, 1H), 7.42 (s, 1H), 6.38 (d, 1H), 6.30 (d, 1H), 3.92 (s, 2H), 3.56 (s, 2H). |
| 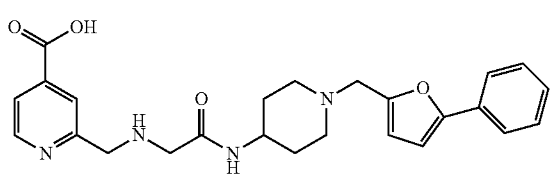 [SMILES: O=C(CNCc1cc(C(=O)O)ccn1)NC1CCN(Cc2ccc(-c3ccccc3)o2)CC1] | 32 | 2-({[({1-[(5-phenylfuran-2-yl)methyl]piperidin-4-yl}carbamoyl)methyl]amino}methyl)pyridine-4-carboxylic acid | E | $^1$H-NMR (300 MHz, CD$_3$OD), δ ppm: 7.82 (s, 1H), 6.70 (s, 1H), 6.40 (d, 1H), 3.92 (s, 2H). |
| 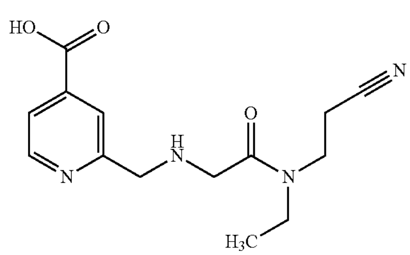 [SMILES: CCN(CCC#N)C(=O)CNCc1cc(C(=O)O)ccn1] | 33 | 2-[({[(2-cyanoethyl)(ethyl)carbamoyl]methyl}amino)methyl]pyridine-4-carboxylic acid | B | $^1$H-NMR (300 MHz, MeOH-d$_4$), δ ppm: 7.7 (s, 1H), 4.0 (s, 2H), 3.6 (m, 4H), 1.2 (t, 3H). |

TABLE 1-continued

| Structure | # | Name | Synthetic Route | NMR |
|---|---|---|---|---|
| 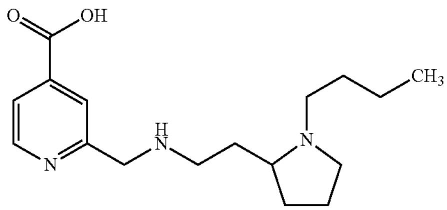 [SMILES: CCCCN1CCCC1CCNCc1cc(C(=O)O)ccn1] | 34 | 2-({[2-(1-butyl-pyrrolidin-2-yl)ethyl]amino}methyl)pyridine-4-carboxylic acid | D | ¹H NMR (300 MHz, Methanol-d₄), δ ppm: 8.00 (s, 1H), 4.53 (s, 2H), 3.58-3.13 (m, 6H), 1.01 (t, 3H). |
| 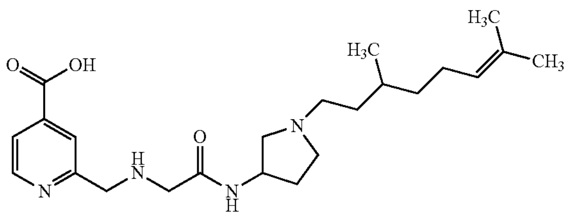 [SMILES: CC(C)=CCCC(C)CCN1CCC(NC(=O)CNCc2cc(C(=O)O)ccn2)C1] | 35 | 2-{[({1-(3,7-dimethyloct-6-en-1-yl)pyrrolidin-3-yl]carbamoyl}methyl)amino]methyl}pyridine-4-carboxylic acid | E | ¹H-NMR (300 MHz, CD₃OD), δ ppm: 7.72 (s, 1H), 5.10 (m, 1H), 4.36 (m, 1H), 3.90 (s, 2H), 3.28 (s, 2H). |
| 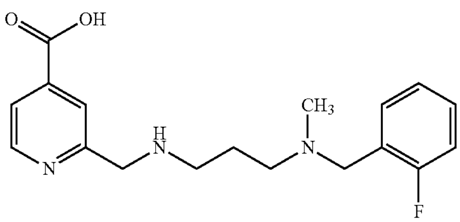 [SMILES: CN(CCCNCc1cc(C(=O)O)ccn1)Cc1ccccc1F] | 36 | 2-{[(3-{[(2-fluorophenyl)methyl](methyl)amino}propyl)amino]methyl}pyridine-4-carboxylic acid | C | ¹H-NMR (300 MHz, CD₃OD), δ ppm: 7.85 (s, 1H), 3.90 (s, 2H), 2.62 (t, 2H), 2.48 (t, 2H). |
| 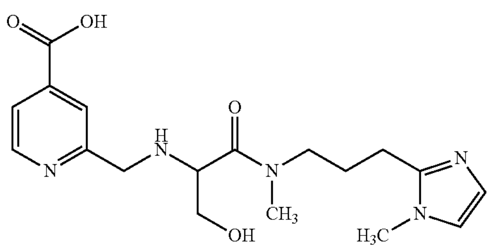 [SMILES: CN(CCCc1nccn1C)C(=O)C(CO)NCc1cc(C(=O)O)ccn1] | 37 | 2-({[(1R)-2-hydroxy-1-{methyl[3-(1-methyl-1H-imidazol-2-yl)propyl]carbamoyl}ethyl]amino}methyl)pyridine-4-carboxylic acid | A | ¹H-NMR (300 MHz, CD₃OD), δ ppm: 8.32 (s, 1H), 7.75 (d, 1H), 7.35 (d, 1H), 4.20 (s, 2H). |
| 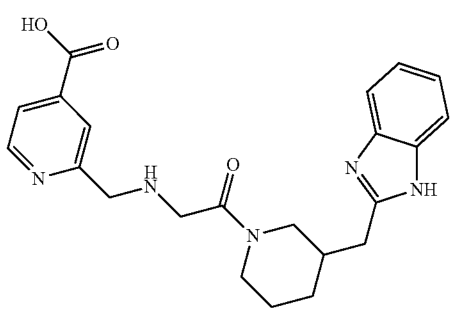 [SMILES: O=C(O)c1ccnc(CNCC(=O)N2CCCC(Cc3nc4ccccc4[nH]3)C2)c1] | 38 | 2-[({2-[3-(1H-1,3-benzodiazol-2-ylmethyl)piperidin-1-yl]-2-oxoethyl}amino)methyl]pyridine-4-carboxylic acid | B | ¹H-NMR (300 MHz, MeOH-d₄), δ ppm: 7.9 (s, 1H), 7.5 (m, 2H), 7.2 (m, 2H). |
| 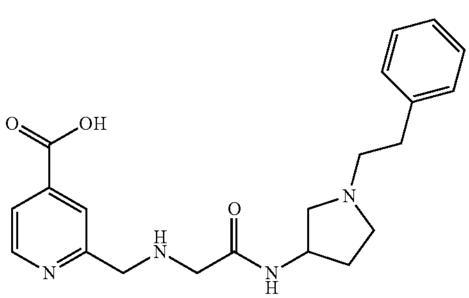 [SMILES: O=C(CNCc1cc(C(=O)O)ccn1)NC1CCN(CCc2ccccc2)C1] | 39 | 2-{[({1-(2-phenylethyl)pyrrolidin-3-yl]carbamoyl}methyl)amino]methyl}pyridine-4-carboxylic acid | E | ¹H-NMR (300 MHz, CD₃OD), δ ppm: 8.52 (d, 1H), 7.80 (s, 1H), 4.36 (m, 1H), 3.92 (m, 1H), 3.28 (m, 2H). |

TABLE 1-continued

| Structure | # | Name | Synthetic Route | NMR |
|---|---|---|---|---|
| 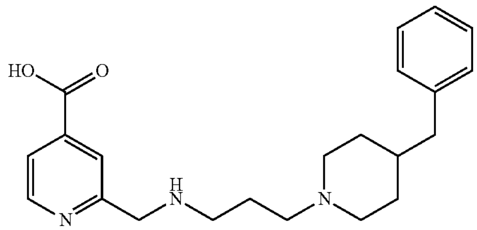 [SMILES: O=C(O)c1ccnc(CNCCCN2CCC(Cc3ccccc3)CC2)c1] | 40 | 2-({[3-(4-benzyl-piperidin-1-yl)propyl]amino}methyl)pyridine-4-carboxylic acid | C | ¹H-NMR (300 MHz, CD₃OD), δ ppm: 7.85 (s, 1H), 7.20 (m, 5H), 3.92 (s, 2H), 3.35 (s, 2H). |
| 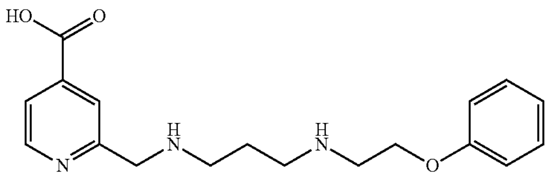 [SMILES: O=C(O)c1ccnc(CNCCCNCCOc2ccccc2)c1] | 41 | 2-[({3-[(2-phenoxyethyl)amino)propyl}amino)methyl]pyridine-4-carboxylic acid | C | ¹H-NMR (300 MHz, CD₃OD), δ ppm: 7.82 (s, 1H), 4.18 (t, 2H), 2.96 (t, 2H), 2.70 (m, 4H). |
| 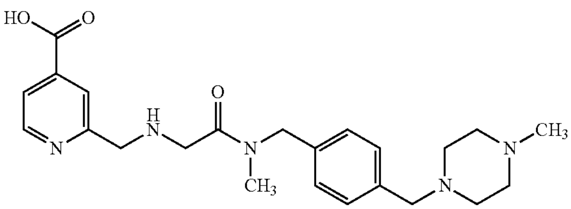 [SMILES: CN1CCN(Cc2ccc(CN(C)C(=O)CNCc3cc(C(=O)O)ccn3)cc2)CC1] | 42 | 2-[({[methyl({4-[(4-methyl-piperazin-1-yl)methyl]phenyl}methyl)carbamoyl]methyl}amino)methyl]pyridine-4-carboxylic acid | B | ¹H-NMR (300 MHz, MeOH-d₄), δ ppm: 7.7 (s, 1H), 4.4 (s, 2H), 4.0 (s, 2H), 3.6 (s, 2H). |
| 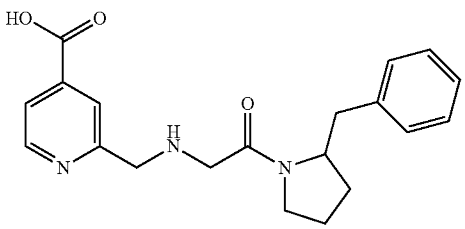 [SMILES: O=C(O)c1ccnc(CNCC(=O)N2CCCC2Cc2ccccc2)c1] | 43 | 2-({[2-(2-benzyl-pyrrolidin-1-yl)-2-oxoethyl]amino}methyl]pyridine-4-carboxylic acid | B | ¹H-NMR (300 MHz, MeOH-d₄), δ ppm: 7.7 (s, 1H), 7.2 (m, 4H), 4.4 (m, 1H), 3.5 (m, 4H), 3.4 (s, 2H). |
| 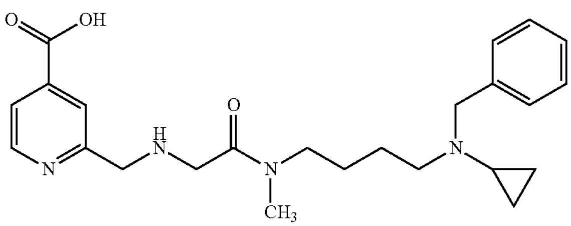 [SMILES: CN(CCCCN(Cc1ccccc1)C1CC1)C(=O)CNCc1cc(C(=O)O)ccn1] | 44 | 2-({[[({4-[benzyl(cyclopropyl)amino]butyl}(methyl)carbamoyl)methyl]amino}methyl)pyridine-4-carboxylic acid | F | ¹H-NMR (300 MHz, MeOH-d₄), δ ppm: 7.80 (s, 1H), 3.90 (s, 2H), 3.70 (s, 2H), 0.50 (m, 2H), 0.40 (m, 2H). |
| 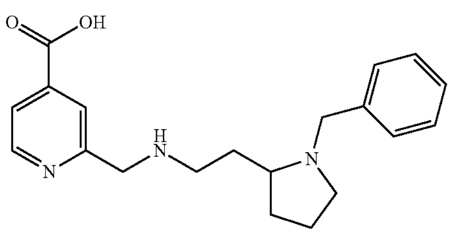 [SMILES: O=C(O)c1ccnc(CNCCC2CCCN2Cc2ccccc2)c1] | 45 | 2-[({2-[(2S)-1-benzylpyrrolidin-2-yl]ethyl}amino)methyl]pyridine-4-carboxylic acid | D | ¹H-NMR (300 MHz, MeOH-d₄), δ ppm: 7.74 (s, 1H), 7.50 (m, 2H), 7.42 (m, 3H), 4.38 (s, 2H). |
| 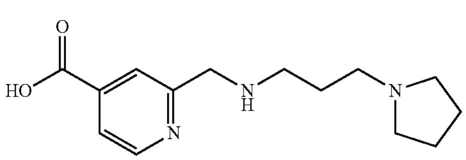 [SMILES: O=C(O)c1ccnc(CNCCCN2CCCC2)c1] | 46 | 2-({[3-(pyrrolidin-1-yl)propyl]amino}methyl)pyridine-4-carboxylic acid | A | ¹H-NMR (300 MHz, CD₃OD): δ 8.54 (d, 1H), 7.86 (s, 1H), 7.72 (dd, 1H), 3.92 (s, 2H), 3.36 (s, 2H), 2.66 (t, 2H), 2.58-2.50 (m, 4H), 1.90 (s, 2H), 1.83-1.73 (m, 4H). |

TABLE 1-continued

| Structure | # | Name | Synthetic Route | NMR |
|---|---|---|---|---|
| 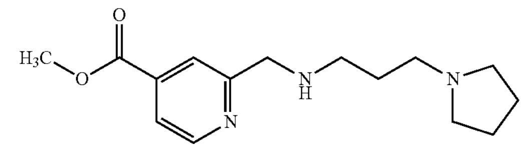 [SMILES: COC(=O)c1ccnc(CNCCCN2CCCC2)c1] | 47 | methyl 2-({[3-(pyrrolidin-1-yl)propyl]amino}methyl)pyridine-4-carboxylate | G | $^1$H-NMR (300 MHz, CD$_3$OD): δ 8.82 (d, 1H), 8.03 (s, 1H), 7.90 (dd, 1H), 4.43 (s, 2H), 3.98 (s, 3H), 3.46-3.36 (m, 6H), 3.22 (t, 2H), 2.29-2.39 (m, 2H), 2.14-2.09 (m, 4H). |
| 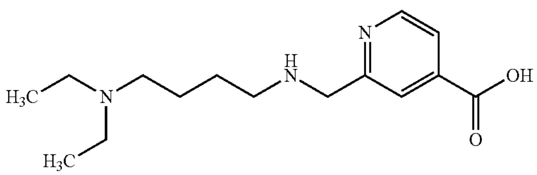 [SMILES: CCN(CC)CCCCNCc1cc(C(=O)O)ccn1] | 48 | 2-({[4-(diethylamino)butyl]amino}methyl)pyridine-4-carboxylic acid | A | $^1$H NMR (300 MHz,) CD$_3$OD 8.54 (dd, 1H), 7.85 (s, 1H), 7.72 (dd, 1H), 3.91 (s, 2H), 2.65-2.43 (m, 8H), 1.55-1.48 (m, 4H), 1.03 (t, 6H). |
| 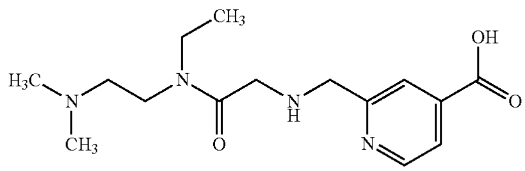 [SMILES: CCN(CCN(C)C)C(=O)CNCc1cc(C(=O)O)ccn1] | 49 | 2-{[({[2-(dimethylamino)ethyl](ethyl)carbamoyl}methyl)amino]methyl}pyridine-4-carboxylic acid | B | $^1$H-NMR (300 MHz, CD$_3$OD): δ 8.55 (d, 1H), 7.88 (s, 1H), 7.73 (d, 1H), 3.96 (s, 2H), 3.54 (s, 2H), 3.52-3.31 (m, 4H), 2.45-2.51 (m, 2H), 2.27 (m, 6H), 1.11-1.19 (m, 3H). |
| 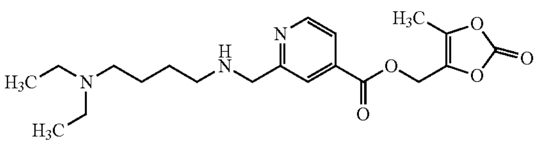 [SMILES: CCN(CC)CCCCNCc1cc(C(=O)OCc2oc(=O)oc2C)ccn1] | 50 | (5-methyl-2-oxo-2H-1,3-dioxol-4-yl)methyl 2-({[4-(diethylamino)butyl]amino}methyl)pyridine-4-carboxylate | G | $^1$H-NMR (300 MHz, CD$_3$OD): δ 8.80 (m, 1H), 7.98 (m, 1H), 7.82 (m, 2H), 5.20 (s, 2H), 4.48 (s, 2H), 3.10-3.40 (m, 8H), 1.70-1.98 (m, 4H), 1.25-1.40 (m, 6H). |
| 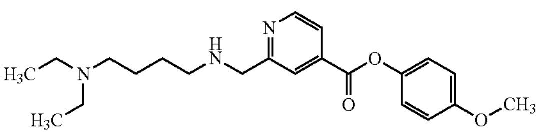 [SMILES: CCN(CC)CCCCNCc1cc(C(=O)Oc2ccc(OC)cc2)ccn1] | 51 | 4-methoxyphenyl 2-({[4-(diethyl-amino)butyl]amino}methyl)pyridine-4-carboxylate | G | $^1$H-NMR (300 MHz, CD$_3$OD): δ 8.88 (d, 1H), 8.13 (s, 1H), 8.05 (dd, 1H), 7.20-7.15 (m, 2H), 7.01-6.96 (m, 2H), 4.53 (s, 2H), 3.81 (s, 3H), 3.27-3.16 (m, 8H), 1.90-1.85 (m, 4H), 1.33 (t, 6H). |
| 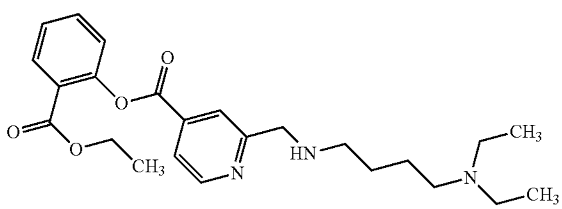 [SMILES: CCOC(=O)c1ccccc1OC(=O)c1ccnc(CNCCCCN(CC)CC)c1] | 52 | 2-(ethoxycarbonyl)phenyl 2-({[4-(diethylamino)butyl]amino}methyl)pyridine-4-carboxylate | G | $^1$H NMR (300 MHz, CD$_3$OD) δ 8.93 (dd, 1H), 8.18 (s 1H), 8.15-8.07 (m, 2H), 7.83-7.62 (m, 1H), 7.49 (dd, 1H), 7.33 (dd, 1H), 4.57 (s, 2H), 4.22 (q, 2H), 3.47-2.99 (m, 10H), 2.01-1.73 (m, 2H), 1.34 (td, 9H). |
| 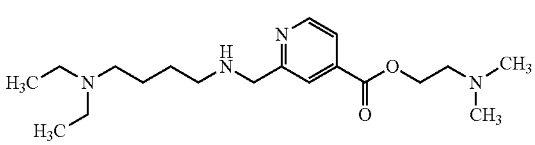 [SMILES: CCN(CC)CCCCNCc1cc(C(=O)OCCN(C)C)ccn1] | 53 | 2-(dimethylamino)ethyl 2-({[4-(diethylamino)butyl]amino}methyl)pyridine-4-carboxylate | G | $^1$H NMR (300 MHz, CD$_3$OD) δ 8.83 (d, 1H), 8.09 (s, 1H), 7.95 (d, 1H), 4.76 (t, 2H), 4.10 (s, 2H), 3.65 (t, 2H), 2.25 (m, 8H), 3.02 (s, 6H), 1.85 (m, 4H), 1.36 (t, 6H). |
| 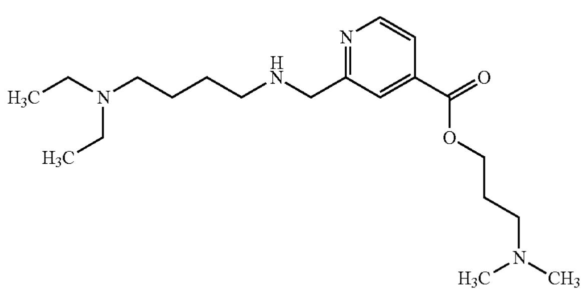 [SMILES: CCN(CC)CCCCNCc1cc(C(=O)OCCCN(C)C)ccn1] | 54 | 3-(dimethylamino)propyl 2-({[4-(diethylamino)butyl]amino}methyl)pyridine-4-carboxylate | G | $^1$H NMR (300 MHz, CD$_3$OD) δ 8.81 (d, 1H), 8.02 (s, 1H), 7.95 (d, 1H), 4.50 (m, 4H), 3.38 (m, 2H), 3.26 (m, 8H), 2.98 (s, 6H), 2.25 (m, 2H), 1.87 (m, 4H), 1.38 (t, 6H). |

TABLE 1-continued

| Structure | # | Name | Synthetic Route | NMR |
|---|---|---|---|---|
| 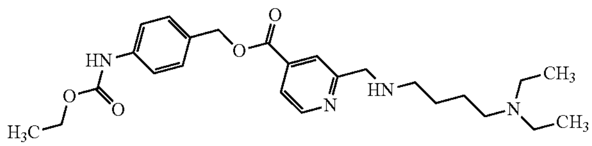 [SMILES: CCOC(=O)Nc1ccc(COC(=O)c2ccnc(CNCCCCN(CC)CC)c2)cc1] | 55 | {4-{[(ethoxycarbonyl)amino]phenyl}methyl 2-({[4-(diethylamino)butyl]amino}methyl)pyridine-4-carboxylate | G | $^1$H-NMR (300 MHz, CD3OD): δ 8.70 (d, 1H), 7.90 (s, 1H), 7.80 (d, 1H), 7.30-7.50 (m, 4H), 5.35 (s, 2H), 4.50 (s, 2H), 3.20 (m, 9H), 1.30 (m, 9H). |
| 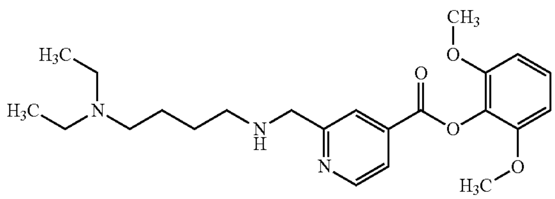 [SMILES: CCN(CC)CCCCNCc1cc(C(=O)Oc2c(OC)cccc2OC)ccn1] | 56 | 2,6-dimethoxyphenyl 2-({[4-(diethylamino)butyl)amino}methyl)pyridine-4-carboxylate | G | $^1$H NMR (300 MHz, CD3OD): δ 8.89 (dd, 1H), 8.15 (d, 1H), 8.05 (dd, 1H), 7.24 (t, 1H), 6.77 (d, 2H), 4.53 (s, 2H), 3.79 (s, 6H), 3.29-3.13 (d, 8H), 1.92-1.80 (m, 4H), 1.33 (t, 6H). |
| 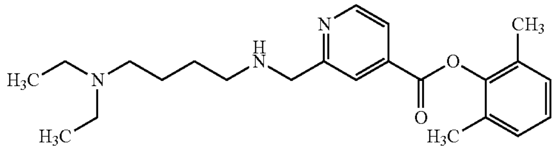 [SMILES: CCN(CC)CCCCNCc1cc(C(=O)Oc2c(C)cccc2C)ccn1] | 57 | 2,6-dimethylphenyl 2-({{(4-(diethylamino)butyl]amino}methyl)pyridine-4-carboxylate | G | $^1$H-NMR (300 MHz, CD3OD): δ 8.90 (d, 1H), 8.20 (s, 1H), 8.00 (d, 1H), 7.2 (s, 3H), 4.50 (s, 2H), 2.20 (s, 6H), 1.80 (m, 4H), 1.30 (m, 6H). |
| 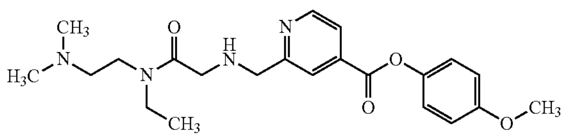 | 58 | 4-methoxyphenyl 2-{[({[2-(dimethylamino)ethyl](ethyl)carbamoyl}methyl)amino]methyl}pyridine-4-carboxylate | G | $^1$H-NMR (300 MHz, CD3OD): δ 8.90 (d, 1H), 8.10 (s, 1H), 8.05 (d, 1H), 7.10 (m, 2H), 7.00 (m, 2H), 4.50 (s, 2H), 4.30 (s, 2H), 3.80 (s, 3H), 3.30 (m, 6H), 2.95 (s, 6H), 1.20 (t, 3H) |
| 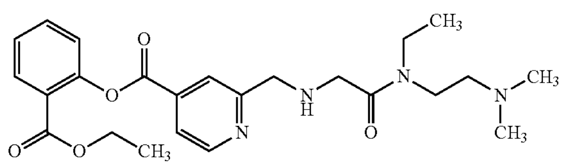 [SMILES: CCOC(=O)c1ccccc1OC(=O)c1ccnc(CNCC(=O)N(CC)CCN(C)C)c1] | 59 | 2-(ethoxycarbonyl)phenyl 2-{[({[2-(dimethylamino)ethyl](ethyl)carbamoyl}methyl)amino]methyl}pyridine-4-carboxylate | G | $^1$H-NMR (300 MHz, CD3OD): δ 8.90 (d, 1H), 8.20 (s, 1H), 8.05 (d, 1H), 7.75 (m, 1H), 7.45 (m, 1H), 7.30 (m, 1H), 4.60 (s, 2H), 4.30 (s, 2H), 3.80 (m, 2H), 3.00 (s, 6H), 1.25 (m, 6H) |
| 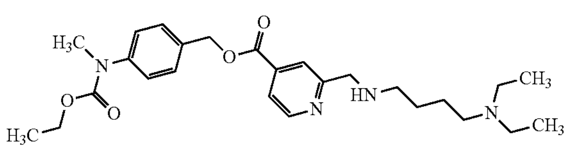 [SMILES: CCOC(=O)N(C)c1ccc(COC(=O)c2ccnc(CNCCCCN(CC)CC)c2)cc1] | 60 | {4-[(ethoxycarbonyl)(methyl)amino]phenyl}methyl 2-({[4-(diethylamino)butyl)amino}methyl)pyridine-4-carboxylate | G | $^1$H-NMR (300 MHz, CD3OD): δ 8.80 (d, 1H), 8.00 (s, 1H), 7.90 (d, 1H), 7.50 (d, 2H), 7.30 (d, 2H), 5.40 (s, 2H), 4.50 (s, 2H), 4.20 (m, 2H), 1.80 (m, 4H), 1.30 (m, 6H), 1.20 (t, 3H) |
| 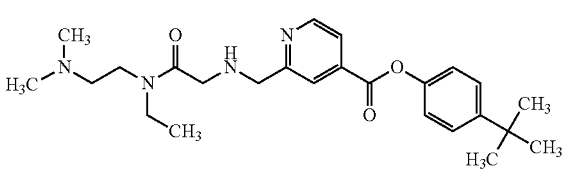 [SMILES: CCN(CCN(C)C)C(=O)CNCc1cc(C(=O)Oc2ccc(C(C)(C)C)cc2)ccn1] | 61 | 4-tert-butylphenyl 2-{[({[2-(dimethylamino)ethyl](ethyl)carbamoyl}methyl)amino]methyl}pyridine-4-carboxylate | G | $^1$H-NMR (300 MHz, CD3OD): δ 8.80 (d, 1H), 8.10 (s, 1H), 8.00 (d, 1H), 7.50 (d, 2H), 7.20 (d, 2H), 4.55 (s, 2H), 4.30 (s, 2H), 3.80 (m, 3H), 2.99 (s, 6H), 1.40 (s, 9H), 1.20 (t, 3H) |
| 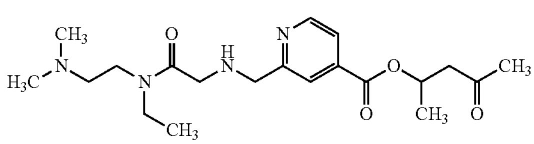 [SMILES: CCN(CCN(C)C)C(=O)CNCc1cc(C(=O)OC(C)CC(C)=O)ccn1] | 62 | 4-oxopentan-2-yl 2-{[({[2-(dimethylamino)ethyl](ethyl)carbamoyl}methyl)amino]methyl}pyridine-4-carboxylate | G | $^1$H-NMR (300 MHz, CD3OD): δ 8.75 (d, 1H), 7.90-8.10 (m, 2H), 5.50 (m, 1H), 4.50 (s, 2H), 4.25 (s, 2H), 3.75 (m, 2H), 1.20-1.50 (m, 6H). |

TABLE 1-continued

| Structure | # | Name | Synthetic Route | NMR |
|---|---|---|---|---|
| 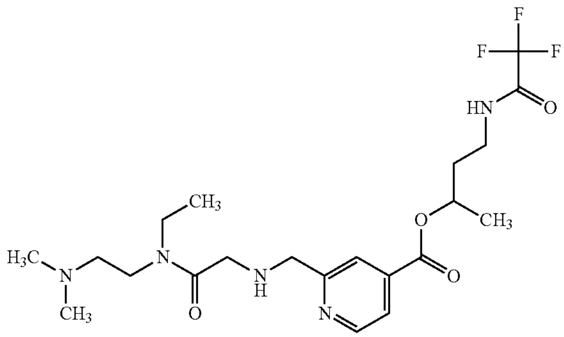 [SMILES: CCN(CCN(C)C)C(=O)CNCc1cc(C(=O)OC(C)CCNC(=O)C(F)(F)F)ccn1] | 63 | 4-(trifluoro-acetamido)butan-2-yl 2-{[({[2-(dimethylamino)ethyl](ethyl)carbamoyl}methyl)amino]methyl}pyridine-4-carboxylate | G | ¹H-NMR (300 MHz, CD₃OD): δ 8.80 (d, 1H), 7.98 (brs, 1H), 7.9 (d, 2H), 5.20 (m, 1H), 4.9 (s, 2H), 4.5 (s, 2H), 4.3 (s, 2H), 3.8 (m, 2H), 3.5-3.3 (m, 6H), 3.0 (s, 3H), 2.0 (m, 2H), 1.3 (d, 3H), 1.2 (t, 3H). |
| 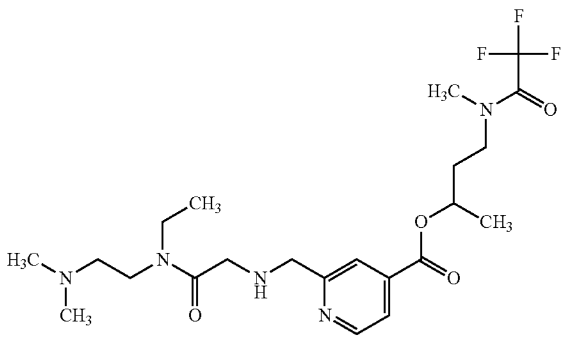 [SMILES: CCN(CCN(C)C)C(=O)CNCc1cc(C(=O)OC(C)CCN(C)C(=O)C(F)(F)F)ccn1] | 64 | 4-(2,2,2-trifluoro-N-methyl-acetamido)butan-2-yl 2-{[({[2-(dimethylamino)ethyl](ethyl)carbamoyl}methyl)amino]methyl}pyridine-4-carboxylate | G | ¹H-NMR (300 MHz, CD₃OD): δ 8.80 (d, 1H), 8.0 (m, 2H), 5.20 (m, 1H), 4.9 (s, 2H), 4.5 (s, 2H), 4.3 (s, 2H), 3.8 (m, 2H), 3.5-3.3 (m, 6H), 3.2 (s, 3H), 3.0 (s, 6H), 2.0 (m, 2H), 1.3 (d, 3H), 1.2 (t, 3H). |
| 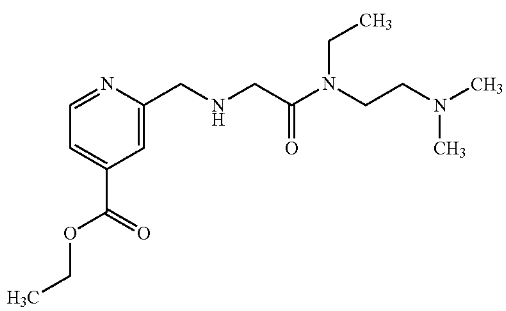 [SMILES: CCOC(=O)c1ccnc(CNCC(=O)N(CC)CCN(C)C)c1] | 65 | ethyl 2-{[({[2-(dimethylamino)ethyl](ethyl)carbamoyl}methyl)amino]methyl}pyridine-4-carboxylate | General Procedure B | ¹H-NMR (300 MHz, CDCl₃): δ 8.7 (d, 1H), 7.9 (s, 1H), 7.8 (d, 1H), 4.4 (q, 2H), 4.0 (s, 2H), 3.5-3.3 (m, 4H), 3.2 (m, 2H), 2.5 (m, 4H), 2.3 (s, 6H), 1.3 (t, 3H), 1.1 (t, 3H). |
| 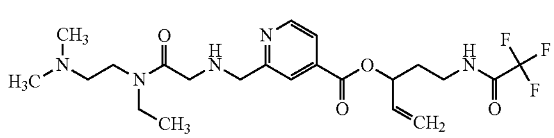 [SMILES: C=CC(CCNC(=O)C(F)(F)F)OC(=O)c1ccnc(CNCC(=O)N(CC)CCN(C)C)c1] | 66 | 5-(trifluoro-acetamido)pent-1-en-3-yl 2-{[({[2-(dimethyl-amino)ethyl](ethyl)carbamoyl}methyl)amino]methyl}pyridine-4-carboxylate | G | ¹H-NMR (300 MHz, CD₃OD): δ 8.84 (d, 1H), 8.02 (s, 1H), 7.96 (d, 1H), 6.04-5.93 (m, 1H), 5.38 (d, 1H), 5.29 (d, 1H), 2.98 (s, 6H), 1.25 (t, 3H). |
| 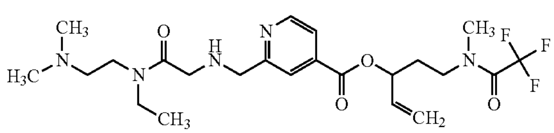 [SMILES: C=CC(CCN(C)C(=O)C(F)(F)F)OC(=O)c1ccnc(CNCC(=O)N(CC)CCN(C)C)c1] | 67 | 5-(2,2,2-trifluoro-N-methyl-acetamido)pent-1-en-3-yl 2-{[({[2-(dimethyl-amino)ethyl](ethyl)carbamoyl}methyl)amino]methyl}pyridine-4-carboxylat | G | ¹H-NMR (300 MHz, CD₃OD): δ 8.85 (d, 1H), 8.02 (s, 1H), 7.96 (d, 1H), 6.05-5.93 (m, 1H), 5.39 (d, 1H), 5.29 (d, 1H), 3.40 (m, 3H), 1.25 (t, 3H). |
| Below | 68 | 2-(2-{[({[2-(dimethylamino)ethyl](ethyl)carbamoyl}methyl)amino]methyl}pyridine-4-carbonyloxy)-3- | G | ¹H-NMR (300 MHz, CD3OD): δ 8.85 (d, 1H), 8.05 (s, 1H), 7.90 (d, 1H), 5.50 (m, 1H), 4.50 (s, 2H), 3.80 (m, 2H), 2.98 (s, 6H), 1.30 (m, 57H), 0.90 (m, 6H) |

TABLE 1-continued

| Structure | # | Name | Synthetic Route | NMR |
|---|---|---|---|---|
| | | (hexadecanoyloxy) propyl hexadecanoate | | |
| 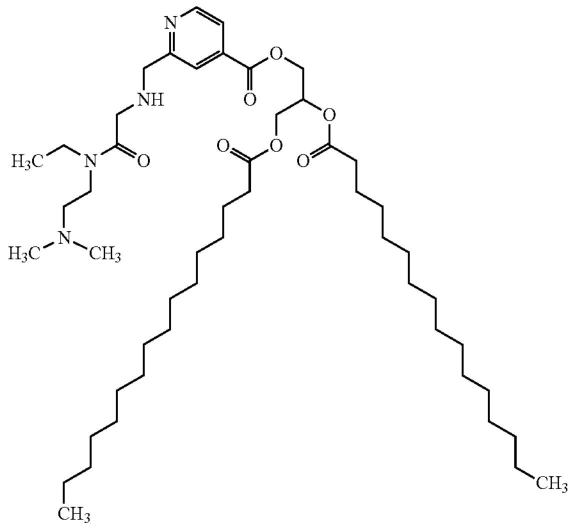 [SMILES: CCCCCCCCCCCCCCCC(=O)OCC(COC(=O)c1ccnc(CNCC(=O)N(CC)CCN(C)C)c1)OC(=O)CCCCCCCCCCCCCCC] | 69 | 1-(2-{[({[2-(dimethylamino) ethyl](ethyl) carbamoyl}methyl) amino]methyl} pyridine-4-carbonyloxy)-3-(hexadecanoyloxy) propan-2-yl hexadecanoate | G | $^1$H-NMR (300 MHz, CD3OD): δ 8.80 (d, 1H), 8.05 (s, 1H), 7.90 (d, 1H), 4.50 (s, 2H), 4.40 (m, 2H), 4.20 (s, 3H), 3.00 (s, 6H), 1.20-1.50 (m, 73H). |
| 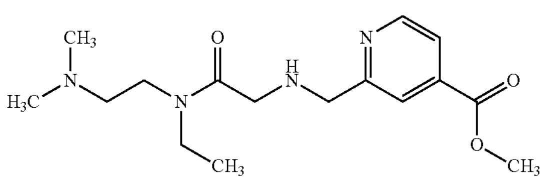 | 70 | methyl 2-{[({[2-(dimethylamino) ethyl](ethyl) carbamoyl}methyl) amino]methyl} pyridine-4-carboxylate | G | $^1$H-NMR (300 MHz, CD3OD): δ 8.80 (d, 1H), 8.10 (s, 1H), 8.00 (d, 1H), 4.70 (s, 2H), 4.40 (s, 2H), 4.00 (s, 3H), 3.00 (s, 6H), 1.25 (t, 3H). |
| 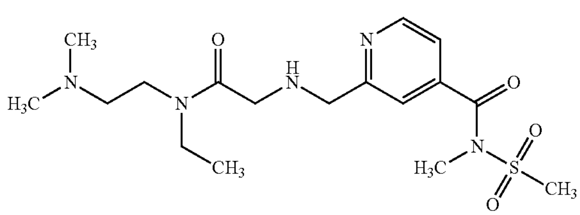 | 71 | 2-{[({[2-(dimethylamino) ethyl](ethyl) carbamoyl} methyl)amino] methyl}-N-methanesulfonyl-N-methylpyridine-4-carboxamide | G | $^1$H-NMR (300 MHz, D$_2$O): δ 8.71 (d, 1H), 7.61 (s, 1H), 7.58 (m, 1H), 4.48 (s, 2H), 4.20 (s, 2H), 3.70 (t, 2H), 3.41 (s, 3H), 3.30-3.24 (m, 4H), 3.20 (s, 3H), 2.86 (s, 6H), 1.10 (t, 3H). |
| 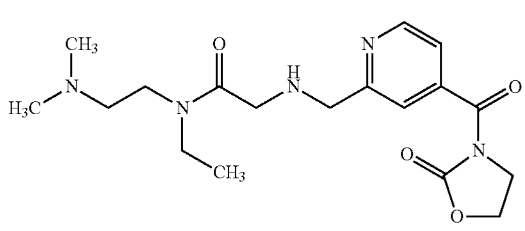 [SMILES: CCN(CCN(C)C)C(=O)CNCc1cc(C(=O)N2CCOC2=O)ccn1] | 72 | N-[2-(dimethylamino) ethyl]-N-ethyl-2-({[4-(2-oxo-1,3-oxazolidine-3-carbonyl)pyridin-2-yl]methyl} amino)acetamide | G | $^1$H-NMR (300 MHz, D$_2$O): δ 8.66 (d, 1H), 7.58-7.46 (m, 2H), 4.46 (s, 2H), 4.19 (s, 2H), 3.79 (t, 2H), 3.73-3.67 (m, 2H), 3.31-3.25 (m, 2H), 3.17-3.11 (m, 2H), 3.03-2.94 (m, 2H), 2.86 (s, 6H), 1.12-1.07 (m, 3H). |

TABLE 1-continued

| Structure | # | Name | Synthetic Route | NMR |
|---|---|---|---|---|
| 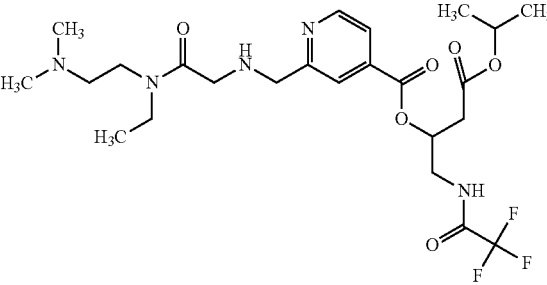 | 73 | propan-2-yl 3-(2-{[({[2-(dimethylamino)ethyl](ethyl)carbamoyl}methyl)amino]methyl}pyridine-4-carbonyloxy)-4-(trifluoroacetamido)butanoate | G | $^1$H-NMR (300 MHz, CD$_3$OD): δ 8.83 (d, 1H), 7.96 (s, 1H), 7.90 (d, 1H), 5.65 (m, 1H), 4.56 (s, 2H), 4.26 (s, 2H), 3.00 (s, 6H), 1.30-1.16 (m, 9H). |
| 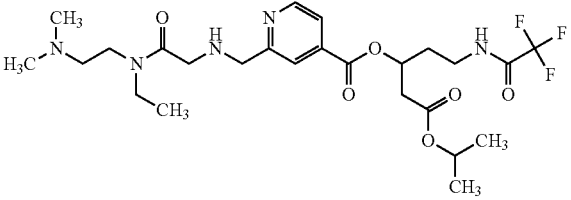 [SMILES: CCN(CCN(C)C)C(=O)CNCc1cc(C(=O)OC(CCNC(=O)C(F)(F)F)CC(=O)OC(C)C)ccn1] | 74 | propan-2-yl 3-(2-{[({[2-(dimethylamino)ethyl](ethyl)carbamoyl}methyl)amino]methyl}pyridine-4-carbonyloxy)-5-(trifluoroacetamido)pentanoate | G | $^1$H-NMR (300 MHz, CD$_3$OD): δ 8.83 (m, 1H), 7.99 (s, 1H), 7.93 (d, 1H), 4.95 (m, 1H), 4.56 (d, 2H), 4.38 (d, 2H), 4.27 (s, 2H), 3.80-3.69 (m, 4H), 3.00 (s, 6H), 1.40-1.36 (m, 9H). |
| 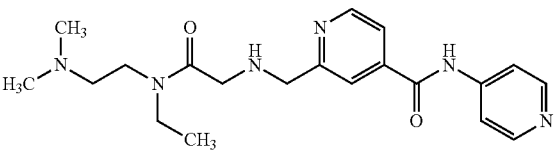 [SMILES: CCN(CCN(C)C)C(=O)CNCc1cc(C(=O)Nc2ccncc2)ccn1] | 75 | 2-{[({[2-(dimethylamino)ethyl](ethyl)carbamoyl}methyl)amino]methyl}-N-(pyridin-4-yl)pyridine-4-carboxamide | G | $^1$H-NMR (300 MHz, CD$_3$OD): δ 8.73 (d, 2H), 8.44 (d, 2H), 8.02 (d, 2H), 6.85 (d, 1H), 4.62 (s, 2H), 4.30 (s, 2H), 3.83 (t, 2H), 3.33-3.31 (m, 4H), 2.99 (s, 6H), 1.26 (t, 3H). |
| 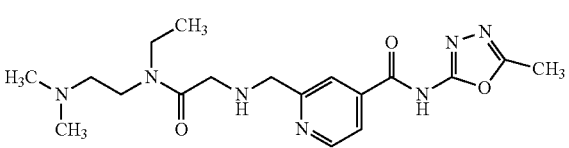 | 76 | 2-{[({[2-(dimethylamino)ethyl](ethyl)carbamoyl}methyl)amino]methyl}-N-(5-methyl-1,3,4-oxadiazol-2-yl)pyridine-4-carboxamide | G | $^1$H-NMR (300 MHz, CD$_3$OD): δ 8.84 (d, 1H), 7.99 (s, 1H), 7.94 (d, 1H), 4.58 (s, 2H), 4.28 (s, 2H), 3.84-3.79 (m, 2H), 3.43-3.36 (m, 2H), 3.32-3.28 (m, 2H), 2.98 (s, 6H), 2.52 (s, 3H), 1.27-1.22 (m, 3H). |
| 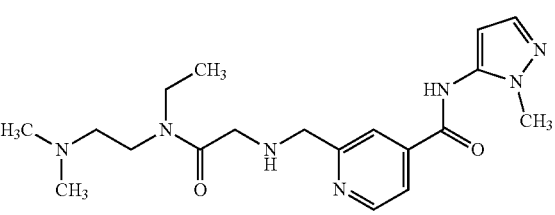 [SMILES: CCN(CCN(C)C)C(=O)CNCc1cc(C(=O)Nc2ccnn2C)ccn1] | 77 | 2-{[({[2-(dimethylamino)ethyl](ethyl)carbamoyl}methyl)amino]methyl}-N-(1-methyl-1H-pyrazol-5-yl)pyridine-4-carboxamide | G | $^1$H-NMR (300 MHz, CD$_3$OD): δ 8.84 (d, 1H), 7.96 (s, 1H), 7.91 (d, 1H), 7.56 (d, 1H), 6.40 (d, 1H), 4.59 (s, 2H), 4.28 (s, 2H), 3.84-3.80 (m, 2H), 3.41-3.35 (m, 4H), 3.82 (s, 3H), 2.98 (s, 6H), 1.26-1.21 (m, 3H). |
| 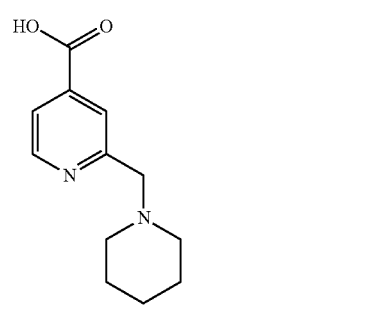 [SMILES: O=C(O)c1ccnc(CN2CCCCC2)c1] | 78 | 2-(piperidin-1-ylmethyl)pyridine-4-carboxylic acid | A | $^1$H-NMR (300 MHz, CD3OD): δ 8.50 (d, 1H), 7.40 (s, 1H), 7.65 (d, 1H), 3.65 (s, 2H), 2.50 (m, 4H), 1.60 (m, 4H), 1.40 (m, 2H) |

TABLE 1-continued

| Structure | # | Name | Synthetic Route | NMR |
|---|---|---|---|---|
| 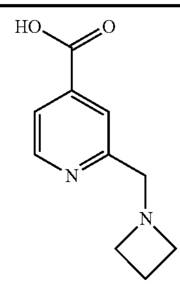 | 79 | 2-(azetidin-1-ylmethyl)pyridine-4-carboxylic acid | A | ¹H-NMR (300 MHz, CD3OD): δ 8.25 (d, 1H), 7.50 (s, 1H), 7.40 (d, 1H), 3.50 (s, 2H), 3.10 (m, 4H), 1.90 (m, 2H) ppm. |
| 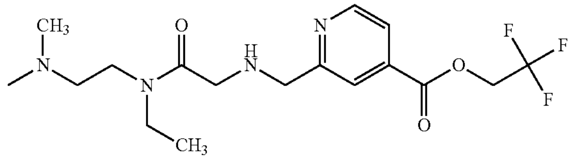 [SMILES: CCN(CCN(C)C)C(=O)CNCc1cc(C(=O)OCC(F)(F)F)ccn1] | 80 | 2,2,2-trifluoroethyl 2-{[({2-(dimethylamino)ethyl}(ethyl)carbamoyl}methyl)amino]methyl}pyridine-4-carboxylate | G | ¹H NMR (300 MHz, DMSO-$d_6$) δ 8.89 (d, 1H), 8.04 (s, 1H), 7.91 (d, 1H), 5.09 (q, 2H), 4.49 (s, 2H), 4.16 (s, 2H), 3.68 (t, 2H), 3.27 (q, 2H), 2.85 (s, 6H), 1.13 (t, 3H). |
| 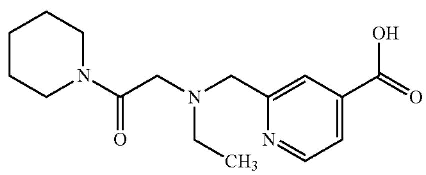 [SMILES: CCN(CC(=O)N1CCCCC1)Cc1cc(C(=O)O)ccn1] | 81 | 2-({ethyl[2-oxo-2-(piperidin-1-yl)ethyl]amino}methyl)pyridine-4-carboxylic acid | I | ¹H NMR (300 MHz, CD₃OD) δ 8.48 (d, 1H), 7.94 (s, 1H), 7.70 (d, 1H), 3.80 (s, 2H), 3.47 (m, 4H), 3.36 (s, 2H), 2.63 (q, 2H), 1.54 (m, 6H), 1.10 (t, 3H). |
| 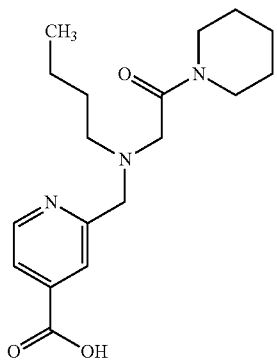 [SMILES: CCCCN(CC(=O)N1CCCCC1)Cc1cc(C(=O)O)ccn1] | 82 | 2-({butyl[2-oxo-2-(piperidin-1-yl)ethyl]amino}methyl)pyridine-4-carboxylic acid | I | ¹H NMR (300 MHz, CD₃OD) δ 8.50 (d, 1H), 7.94 (s, 1H), 7.71 (d, 1H), 3.80 (s, 2H), 3.46 (m, 4H), 3.35 (s, 2H), 2.54 (m, 2H), 1.51 (m, 8H), 1.28 (m, 2H), 0.88 (t, 3H). |
| 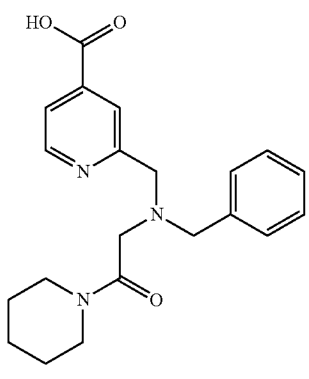 [SMILES: O=C(O)c1ccnc(CN(CC(=O)N2CCCCC2)Cc2ccccc2)c1] | 83 | 2-({benzyl[2-oxo-2-(piperidin-1-yl)ethyl]amino}methyl)pyridine-4-carboxylic acid | I | ¹H NMR (300 MHz, CD₃OD) δ 8.49 (d, 1H), 8.05 (s, 1H), 7.72 (d, 1H), 7.48-7.08 (m, 5H), 3.85 (s, 2H), 3.71 (s, 2H), 3.43 (m, 2H), 3.31 (m, 4H), 1.73-1.33 (m, 6H). |
| 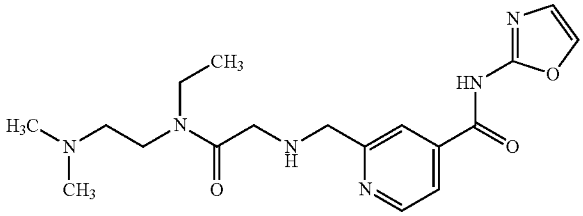 [SMILES: CCN(CCN(C)C)C(=O)CNCc1cc(C(=O)Nc2ncco2)ccn1] | 84 | 2-{[({2-(dimethylamino)ethyl}(ethyl)carbamoyl}methyl)amino]methyl}-N-(1,3-oxazol-2-yl)pyridine-4-carboxamide | G | ¹H-NMR (300 MHz, CD₃OD): δ 8.76 (d, 1H), 7.94 (s, 1H), 7.89 (d, 1H), 7.65 (s, 1H), 7.50 (s, 1H), 4.51 (s, 2H), 4.21 (s, 2H), 3.77-3.73 (m, 2H), 3.37-3.23 (m, 4H), 2.92 (s, 6H), 1.21-1.16 (m, 3H). |

TABLE 1-continued

| Structure | # | Name | Synthetic Route | NMR |
|---|---|---|---|---|
| 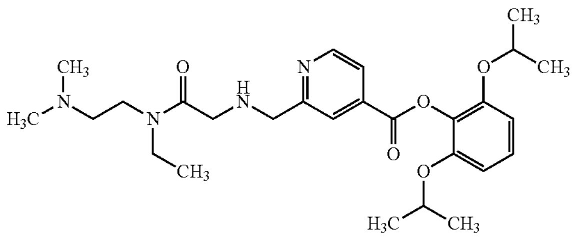 [SMILES: CCN(CCN(C)C)C(=O)CNCc1cc(C(=O)Oc2c(OC(C)C)cccc2OC(C)C)ccn1] | 85 | 2,6-bis(propan-2-yloxy)phenyl 2-{[({[2-(dimethylamino)ethyl](ethyl)carbamoyl}methyl)amino]methyl}pyridine-4-carboxylate | G | ¹H-NMR (300 MHz, CD₃OD): δ 8.94 (m, 1H), 8.16 (s, 1H), 8.11 (d, 1H), 7.18 (t, 1H), 6.75 (d, 2H), 4.60 (m, 2H), 4.30 (s, 2H), 3.00 (s, 6H), 1.30-1.00 (m, 15H). |
| 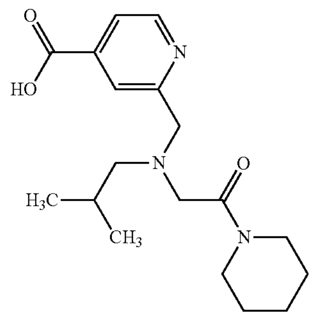 [SMILES: CC(C)CN(CC(=O)N1CCCCC1)Cc1cc(C(=O)O)ccn1] | 86 | 2-{[(2-methylpropyl)[2-oxo-2-(piperidin-1-yl)ethyl]amino]methyl}pyridine-4-carboxylic acid | I | ¹H NMR (300 MHz, CD₃OD): δ 8.48 (d, 1H), 7.99 (s, 1H), 7.71 (d, 1H), 3.79 (s, 2H), 3.55-3.37 (m, 4H), 3.32 (s, 2H), 2.34 (d, 2H), 1.82 (m, 1H), 1.56 (m, 6H), 0.88 (d, 6H). |
| 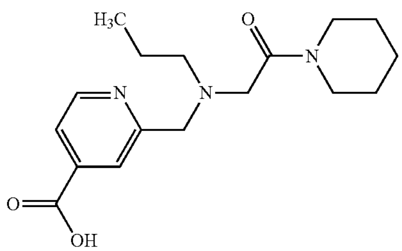 [SMILES: CCCN(CC(=O)N1CCCCC1)Cc1cc(C(=O)O)ccn1] | 87 | 2-({[2-oxo-2-(piperidin-1-yl)ethyl](propyl)amino}methyl)pyridine-4-carboxylic acid | I | ¹H NMR (300 MHz, CD₃OD): δ 8.48 (d, 1H), 7.97 (s, 1H), 7.71 (d, 1H), 3.80 (s, 2H), 3.47 (m, 4H), 3.35 (s, 2H), 2.69-2.26 (m, 2H), 1.75-1.45 (m, 8H), 0.87 (t, 3H). |
| 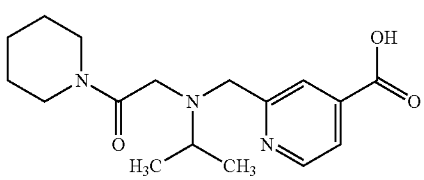 [SMILES: CC(C)N(CC(=O)N1CCCCC1)Cc1cc(C(=O)O)ccn1] | 88 | 2-({[2-oxo-2-(piperidin-1-yl)ethyl](propan-2-yl)amino}methyl)pyridine-4-carboxylic acid | I | ¹H NMR (300 MHz, CD₃OD) δ 8.45 (d, 1H), 8.00 (s, 1H), 7.69 (d, 1H), 3.76 (s, 2H), 3.45-3.37 (m, 4H), 3.34 (s, 2H), 3.12-2.93 (m, 1H), 1.73-1.36 (m, 6H), 1.13 (d, 6H). |
| 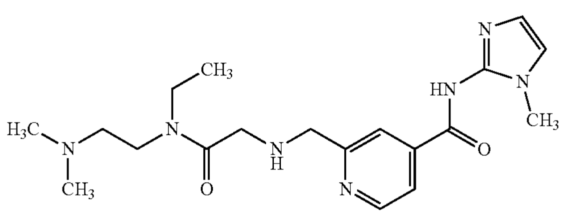 [SMILES: CCN(CCN(C)C)C(=O)CNCc1cc(C(=O)Nc2nccn2C)ccn1] | 89 | 2-{[({[2-(dimethylamino)ethyl](ethyl)carbamoyl}methyl)amino]methyl}-N-(1-methyl-1H-imidazol-2-yl)pyridine-4-carboxamide | G | ¹H-NMR (300 MHz, CD₃OD): δ 8.82 (s, 1H), 7.93 (s, 1H), 7.34 (s, 1H), 7.29 (s, 1H), 6.76 (s, 1H), 3.82-3.73 (m, 4H), 3.46-3.43 (m, 2H), 3.38-3.30 (m, 4H), 3.26 (s, 3H), 2.93 (s, 6H), 1.27-1.12 (m, 3H). |
| 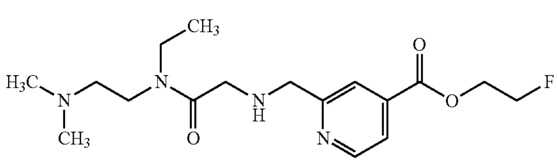 [SMILES: CCN(CCN(C)C)C(=O)CNCc1cc(C(=O)OCCF)ccn1] | 90 | 2-fluoroethyl 2-{[({[2-(dimethylamino)ethyl](ethyl)carbamoyl}methyl)amino]methyl}pyridine-4-carboxylate | G | ¹H-NMR (300 MHz, CDCl₃): δ 8.72 (dd, 1H), 7.96 (d, 1H), 7.73 (td, 1H), 4.45 (td, 1H), 4.04-4.03 (m, 2H), 3.95 (s, 2H), 3.52-3.49 (m, 4H), 3.52-3.49 (m, 4H), 3.47-3.38 (m, 2H), 2.52-2.39 (m, 3H), 2.30 (s, 6H), 1.17-1.11 (m, 3H). |
| 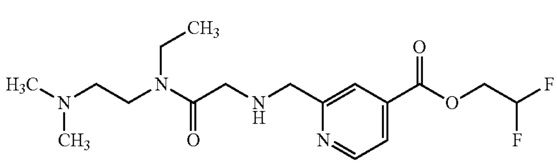 [SMILES: CCN(CCN(C)C)C(=O)CNCc1cc(C(=O)OCC(F)F)ccn1] | 91 | 2,2-difluoroethyl 2-{[({[2-(dimethylamino)ethyl](ethyl)carbamoyl}methyl)amino]methyl}pyridine-4-carboxylate | G | ¹H-NMR (300 MHz, CDCl₃): δ 8.72 (d, 1H), 7.98 (s, 1H), 7.76 (dd, 1H), 6.09 (m, 1H), 4.82 (m, 1H), 4.68-4.63 (m, 2H), 4.55 (m, 1H), 4.04 (s, 2H), 3.50 (s, 2H), 3.49-3.38 (m, 2H), 3.31-3.24 (m, 2H), 2.29 (s, 6H), 1.18-1.11 (m, |

TABLE 1-continued

| Structure | # | Name | Synthetic Route | NMR |
|---|---|---|---|---|
| 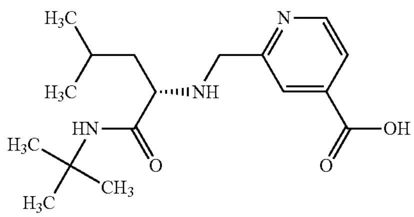 [SMILES: CC(C)C[C@H](NCc1cc(C(=O)O)ccn1)C(=O)NC(C)(C)C] | 92 | 2-({[(1S)-1-(tert-butylcarbamoyl)-3-methylbutyl]amino}methyl)pyridine-4-carboxylic acid | B | ¹H NMR (300 MHz, CD₃OD) δ 8.51 (d, 1H), 7.87 (s, 1H), 7.71 (d, 1H), 3.84 (d, 2H), 3.31 (s, 1H), 3.11 (dd, 1H), 1.82-1.64 (m, 1H), 1.53-1.40 (m, 2H), 1.32 (s, 9H), 0.90 (dd, 6H). 3H). |
| 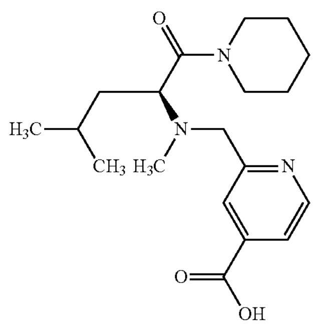 [SMILES: CC(C)C[C@@H](C(=O)N1CCCCC1)N(C)Cc1cc(C(=O)O)ccn1] | 93 | 2-({methyl[(2S)-4-methyl-1-oxo-1-(piperidin-1-yl)pentan-2-yl]amino}methyl)pyridine-4-carboxylic acid | A | ¹H NMR (300 MHz, CD₃OD) δ 8.46 (d, 1H), 7.96 (s, 1H), 7.70 (d, 1H), 3.98-3.65 (m, 3H), 3.57 (m, 3H), 2.81 (s, 1H), 2.28 (s, 3H), 1.95-1.79 (m, 1H), 1.76-1.41 (m, 6H), 0.93 (dd, 6H). |

Illustrative preparations of compounds within Table 1 are as follows.

2-({[2-(dimethylamino)ethyl]amino}methyl)pyridine-4-carboxylic acid (#2)

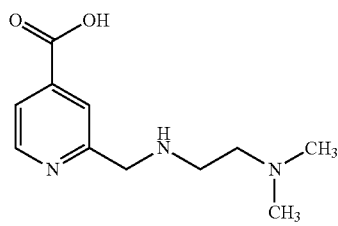 [SMILES: CN(C)CCNCc1cc(C(=O)O)ccn1]

Synthetic Route A

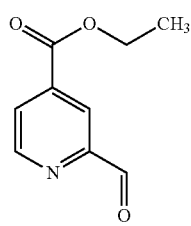

General Procedure B →

(a) General Procedure A → Title Compound

General Procedure A (Ester Hydrolysis)

The ester (Ethyl 2-({[2-(dimethylamino)ethyl]amino}methyl)pyridine-4-carboxylate (a)) was dissolved in MeOH-THF-H₂O (1:1:1) and LiOH (1.0 equiv) was added. The reaction mixture was stirred at room temperature and monitored by TLC. Solvents were removed in vacuo. Worked up by dissolving in water and extract with Et₂O. The aqueous basic layer was acidified with 1N HCl to pH 1, and the solution was concentrated to dryness to afford the hydrochloric acid salt of title compound as a colorless solid.

¹H NMR (300 MHz, Methanol-d₄), δ ppm: 8.82 (dd, 1H), 8.03 (s, 1H), 7.94 (dd, 1H), 4.58 (s, 2H), 3.63 (m, 4H), 3.0 (s, 6H).

ES-MS: 224 [M+1].

2-({[2-oxo-2-(pyrrolidin-1-yl)ethyl]amino}methyl)pyridine-4-carboxylic acid (#13)

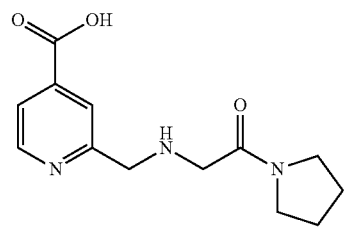 [SMILES: O=C(O)c1ccnc(CNCC(=O)N2CCCC2)c1]

Synthetic Route B

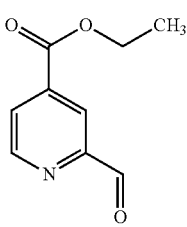

General Procedure B →

-continued

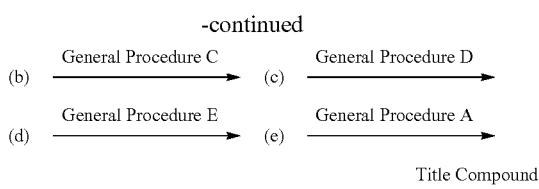

Prepared by General Procedure A from ethyl 2-({2,2,2-trifluoro-N-[2-oxo-2-(pyrrolidin-1-yl)ethyl]acetamido}methyl)pyridine-4-carboxylate (e). Worked up by trituration of the solid residue with Et$_2$O to give hydrochloric acid salt of the title compound as white powder.

$^1$H-NMR (300 MHz, MeOH-d$_4$): δ 8.4 (d, 1H), 7.7 (s, 1H), 7.6 (d, 1H), 3.7 (s, 2H), 4.0 (s, 2H), 3.4 (m, 6H), 1.5 (m, 4H).

2-{[(3-{[3-(pyrrolidin-1-yl)propyl]amino}propyl)amino]methyl}pyridine-4-carboxylic acid (#21)

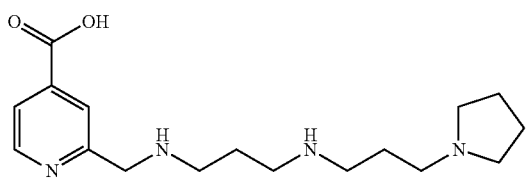 [SMILES: O=C(O)c1ccnc(CNCCCNCCCN2CCCC2)c1]

Synthetic Route C

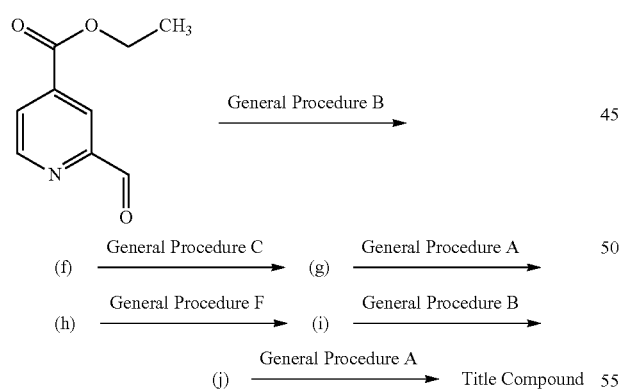

Prepared by General Procedure A from ethyl 2-{[2,2,2-trifluoro-N-(3-{[3-(pyrrolidin-1-yl)propyl]amino}propyl)acetamido] methyl}pyridine-4-carboxylate (j). Work up yielded hydrochloric acid salt of the title compound white sticky solid.

1H NMR (300 MHz, D2O): δ 8.72 (d, 1H), 7.96 (s, 1H), 7.90 (d, 1H), 4.48 (s, 2H), 3.60 (m, 4H), 2.92-3.25 (m, 8H), 1.84-2.25 (m, 8H).

ES-MS: 321.40 [M+H].

2-({[(3R)-1-(3-phenylpropyl)pyrrolidin-3-yl]amino}methyl)pyridine-4-carboxylic acid (#28)

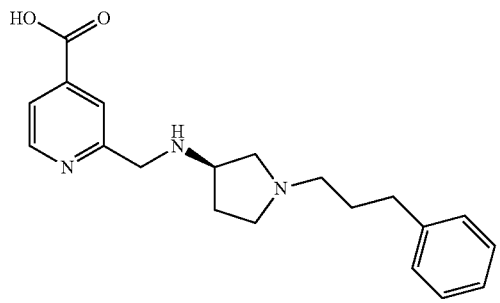 [SMILES: O=C(O)c1ccnc(CN[C@@H]2CCN(CCCc3ccccc3)C2)c1]

Synthetic Route D

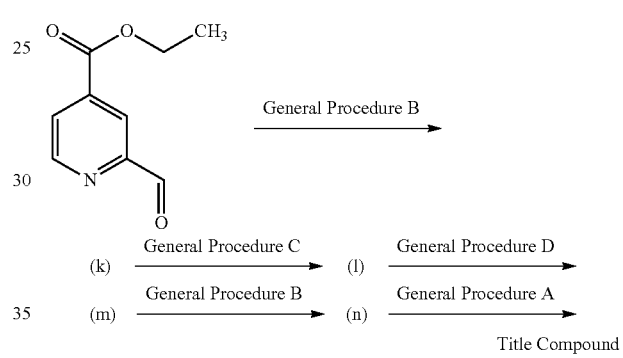

Prepared by General Procedure A from ethyl 2-({2,2,2-trifluoro-N-[(3R)-1-(3-phenylpropyl)pyrrolidin-3-yl]acetamido}methyl)pyridine-4-carboxylate (n). Isolated as lithium salt after work up by dissolving residue in minimum of water and extract with DCM. The aqueous phase was evaporated to dryness yielding the title compound as white solid.

$^1$H-NMR (300 MHz, CDCl$_3$): δ 8.50 (d, 1H), 7.80 (s, 1H), 7.65 (d, 1H), 7.20 (m, 5H), 3.85 (s, 2H), 3.1-2.4 (m, 8H), 2.25 (m, 1H), 2.20 (m, 1H), 1.90-1.55 (m, 3H).

ES-MS: 340 [M+1].

2-({[({1-[(2-methoxyphenyl)methyl]piperidin-4-yl}carbamoyl)methyl]amino}methyl)pyridine-4-carboxylic acid (#29)

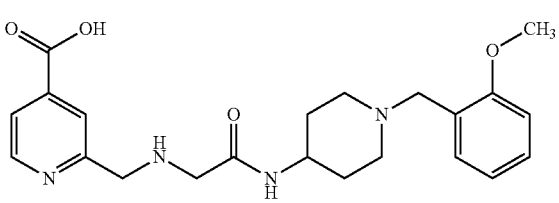 [SMILES: COc1ccccc1CN1CCC(NC(=O)CNCc2cc(C(=O)O)ccn2)CC1]

Synthetic Route E

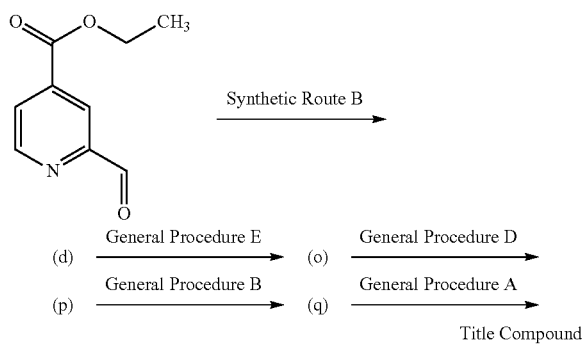

Prepared by General Procedure A from ethyl 2-({2,2,2-trifluoro-N-[({1-[(2-methoxyphenyl)methyl]piperidin-4-yl}carbamoyl)methyl]acetamido}methyl)pyridine-4-carboxylate (q) using 2 equivalents of LiOH. Isolated as lithium salt after work up by dissolving residue in minimum of water and extract with DCM. The aqueous phase was evaporated to dryness yielding the title compound as white solid.

¹H-NMR (300 MHz, CD₃OD): δ 8.54 (d, 1H), 7.82 (s, 1H), 7.65 (d, 1H), 7.26 (m, 2H), 6.94 (m, 2H), 3.90 (s, 2H), 3.85 (s, 3H), 3.72 (m, 3H), 3.62 (s, 2H), 3.24 (s, 2H), 2.94 (m, 2H), 2.24 (m, 2H), 1.90 (m, 3H), 1.60 (m, 2H).
ES-MS: 411 [M−H].

2-({[({4-[benzyl(cyclopropyl)amino]butyl}(methyl)carbamoyl)methyl]amino}methyl)pyridine-4-carboxylic acid (#44)

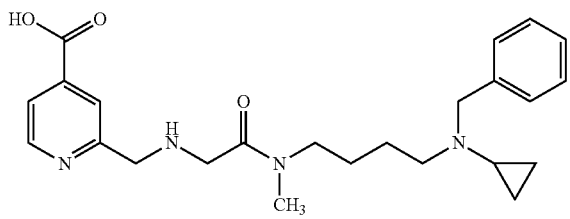 [SMILES: CN(CCCCN(Cc1ccccc1)C1CC1)C(=O)CNCc1cc(C(=O)O)ccn1]

Synthetic Route F

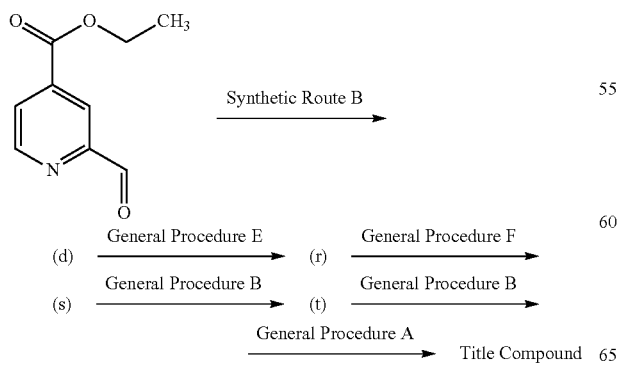

Prepared by General Procedure A from ethyl 2-({N-[({4-benzyl(cyclopropyl)amino]butyl}(methyl)carbamoyl)methyl]-2,2,2-trifluoroacetamido}methyl)pyridine-4-carboxylate (u) using 2.5 equivalents of LiOH. Isolated as lithium salt after work up by dissolving residue in minimum of water and extract with DCM. The aqueous phase was evaporated to dryness yielding the title compound as white solid.

¹H-NMR (300 MHz, CDCl₃): δ 8.50 (d, 1H), 7.80 (s, 1H), 7.70 (d, 1H), 7.25 (m, 5H), 3.90 (s, 2H), 3.70 s, 2H), 3.50-3.40 (m, 3H), 2.25 (m, 1H), 2.95 (s, 3H), 2.55 (m, 2H), 1.75 (m, 1H), 1.50 (m, 4H), 0.50 (m, 2H), 0.40 (m, 2H).
ES-MS: 425 [M+1].

2-{[({[2-(dimethylamino)ethyl](ethyl)carbamoyl}methyl)amino]methyl}-N-(pyridin-4-yl)pyridine-4-carboxamide (#75)

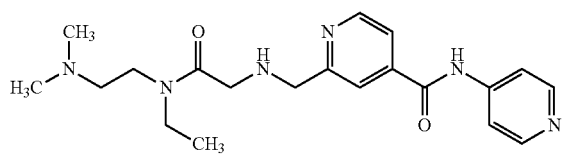

Synthetic Route G

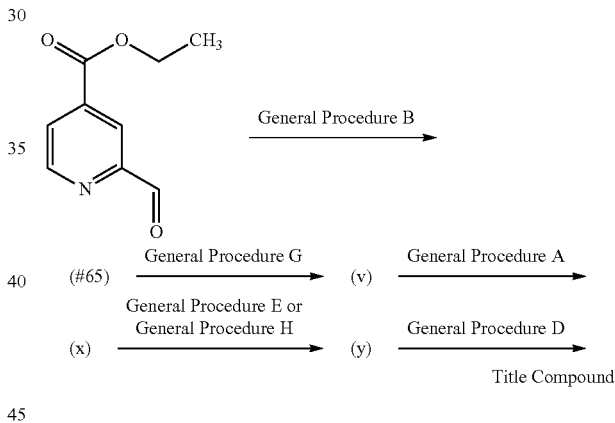

Prepared by general procedure D from tert-butyl N-({[2-(dimethylamino)ethyl](ethyl)carbamoyl}methyl)-N-({4-[(pyridin-4-yl)carbamoyl]pyridin-2-yl}methyl)carbamate (y) to get the title compound as yellow oil.

¹H-NMR (300 MHz, CD₃OD): δ 8.73 (d, 2H), 8.44 (d, 2H), 8.02 (d, 2H), 6.85 (d, 1H), 4.62 (s, 2H), 4.30 (s, 2H), 3.83 (t, 2H), 3.33-3.31 (m, 4H), 2.99 (s, 6H), 1.26 (t, 3H).
ES-MS: 486 [M+1]

4-oxopentan-2-yl 2-{[({[2-(dimethylamino)ethyl](ethyl)carbamoyl}methyl)amino]methyl}pyridine-4-carboxylate (#62)

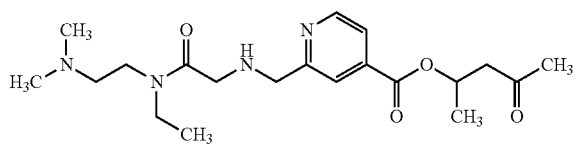

Synthetic Route H

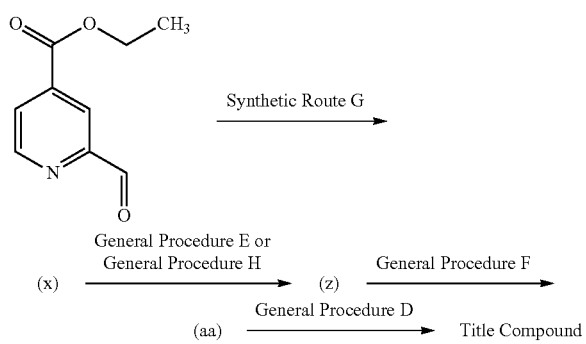

Prepared by General Procedure D from 4-oxopentan-2-yl 2-({[(tert-butoxy)carbonyl]({[2-(dimethylamino)ethyl](ethyl)carbamoyl}methyl)amino}methyl)pyridine-4-carboxylate (aa) to get the title compound as a colorless oil.

$^1$H-NMR (300 MHz, CD3OD): δ 8.75 (d, 1H), 7.90-8.10 (m, 2H), 5.50 (m, 1H), 4.50 (s, 2H), 4.25 (s, 2H), 3.75 (m, 2H), 1.20-1.50 (m, 6H).

ES-MS: 393 [M+1]

2-({ethyl[2-oxo-2-(piperidin-1-yl)ethyl]amino}methyl)pyridine-4-carboxylic acid (#81)

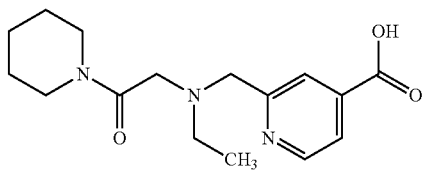 [SMILES: CCN(CC(=O)N1CCCCC1)Cc1cc(C(=O)O)ccn1]

Synthetic Route I

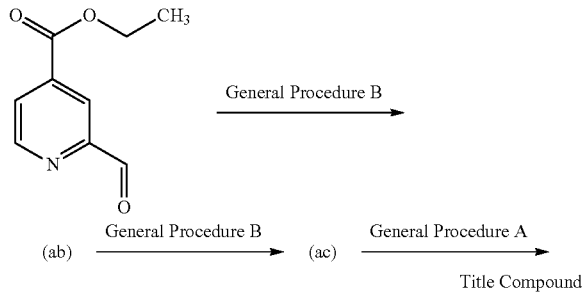

Prepared by general procedure A from ethyl 2-({ethyl[2-oxo-2-(piperidin-1-yl)ethyl]amino}methyl) pyridine-4-carboxylate to get the title compound as yellow solid.

$^1$H NMR (300 MHz, CD$_3$OD) δ 8.48 (d, 1H), 7.94 (s, 1H), 7.70 (d, 1H), 3.80 (s, 2H), 3.47 (m, 4H), 3.36 (s, 2H), 2.63 (q, 2H), 1.54 (m, 6H), 1.10 (t, 3H).

ES-MS: 306 [M+1]

Intermediates

Ethyl 2-({[2-(dimethylamino)ethyl]amino}methyl)pyridine-4-carboxylate (a)

General Procedure B (Reductive Amination)

To a mixture of aldehyde (ethyl 2-formylpyridine-4-carboxylate) (1.0 equiv), and amine (N1,N1-dimethylethane-1,2-diamine) (1.0 equiv), in 1,2-dichloroethane was added AcOH (1.0 equiv), followed by NaBH(OAc)$_3$ (2.5 equiv), and the mixture was stirred at room temperature, overnight. Aqueous work up (EtOAc/NaHCO$_3$) and purification by column chromatography (CH2Cl2/MeOH/NH$_4$OH, 90:10:1) to yield the title compound as a colorless glue.

1H NMR (300 MHz, Methanol-d$_4$): δ 8.68 (dd, 1H), 7.87 (s, 1H), 7.67 (dd, 1H), 4.34 (q, 2H), 3.87 (s, 2H), 2.58 (t, 2H), 2.33 (t, 2H), 2.11 (s, 6H), 1.32 (t, 3H).

Ethyl 2-({[2-(tert-butoxy)-2-oxoethyl]amino}methyl)pyridine-4-carboxylate (b)

Prepared by General Procedure B from ethyl 2-formylpyridine-4-carboxylate and tert-butyl 2-aminoacetate. Title compound isolated as yellow oil by column chromatography (EtOAc/hexanes).

$^1$H-NMR (300 MHz, MeOH-d$_4$): δ 8.7 (d, 1H), 7.8 (s, 1H), 7.7 (d, 1H), 4.4 (s, 2H), 4.3 (q, 2), 3.8 (s, 2H), 3.3 (s, 2H), 1.4 (s, (H), 1.3 (t, 3H)

ES-MS: 295 [M+1].

Ethyl 2-{[(3-hydroxypropyl)amino]methyl}pyridine-4-carboxylate (f)

Prepared by General Procedure B from ethyl 2-formylpyridine-4-carboxylate and 3-aminopropan-1-ol.

$^1$H NMR (300 MHz, CDCl$_3$), δ ppm: 8.72 (d, 1H), 7.98 (s, 1H), 7.75 (d, 1H), 4.45 (q, 2H), 3.95 (s, 2H), 3.70 (t, 2H), 2.80 (t, 2H), 1.75 (m, 2H), 1.40 (t, 3H).

Ethyl 2-({[(3R)-1-[(tert-butoxy)carbonyl]pyrrolidin-3-yl]amino}methyl)pyridine-4-carboxylate (k)

Prepared by General Procedure B from ethyl 2-formylpyridine-4-carboxylate and tert-butyl (3R)-3-aminopyrrolidine-1-carboxylate. Column chromatography (MeOH/DCM) gave the title compound as greenish oil.

$^1$H-NMR (300 MHz, CDCl$_3$): δ 8.70 (d, 1H), 7.86 (s, 1H), 7.74 (d, 1H), 4.50 (q, 2H), 4.00 (s, 2H), 3.60-3.33 (m 4H), 3.25 (m, 1H), 2.09 (m, 1H), 1.90-1.72 (m, 2H), 1.46 (s, 9H), 1.41 (t, 3H).

ES-MS: 350 [M+1]

Ethyl 2-{[2,2,2-trifluoro-N-(3-{[3-(pyrrolidin-1-yl)propyl]amino}propyl)acetamido]methyl}pyridine-4-carboxylate (j)

Prepared by General Procedure B from ethyl 2-{[2,2,2-trifluoro-N-(3-oxopropyl)acetamido]methyl}pyridine-4-carboxylate (i) and 3-(pyrrolidin-1-yl)propan-1-amine. Column chromatography (MeOH/DCM) gave the title compound.

$^1$H NMR (300 MHz, CD$_3$OD): δ 8.66 (dd, 1H), 7.95 (s, 1H), 7.78 (dd, 1H), 4.42 (q, 2H), 3.98 (s, 2H), 3.56 (m, 4H), 2.42-2.75 (m, 8H), 1.86 (m, 8H), 1.40 (t, 3H).

Ethyl 2-{[N-({[4-(cyclopropylamino)butyl](methyl)carbamoyl}methyl)-2,2,2-trifluoroacetamido]methyl}pyridine-4-carboxylate (t)

Prepared by General Procedure B from ethyl 2-[(2,2,2-trifluoro-N-{[methyl(4-oxobutyl)carbamoyl]methyl}acetamido)methyl]pyridine-4-carboxylate (s) and cyclopropylamine. Column chromatography (EtOAc/hexanes) gave the title compound as yellow oil.

$^1$H-NMR (300 MHz, CDCl$_3$): δ 8.70 (dd, 1H), 7.85 (ss, 1H), 7.74 (dd, 1H), 4.95 (dd, 2H), 4.40 (q, 2H), 4.32 (ss, 2H), 3.31 (m, 1H), 3.25 (m, 1H), 2.90 (s, 3H), 2.73 (m, 1H), 2.50 (m, 1H), 2.01 (m, 1H), 1.85-1.30 (m, 8H), 0.53.034 (m, 4H).

ES-MS: 459 [M+1]

Ethyl 2-({2,2,2-trifluoro-N-[(3R)-1-(3-phenylpropyl)pyrrolidin-3-yl]acetamido}methyl)pyridine-4-carboxylate (n)

Prepared by General Procedure B from 3-phenylpropanal ethyl 2-({2,2,2-trifluoro-N-[(3R)-pyrrolidin-3-yl]acetamido}methyl)pyridine-4-carboxylate (m).

$^1$H-NMR (300 MHz, CDCl$_3$): δ 8.70 (d, 1H), 7.80 (s, 1H), 7.72 (dd, 1H), 7.24 (m, 5H), 4.95 (q, 2H), 4.37 (m, 2H), 3.78 (m, 1H), 2.60 (m, 3H), 2.46 (m, 2H), 2.32 (m, 2H), 2.21 (m, 1H), 2.04 (m, 2H), 1.88 (m, 1H), 1.73 (m, 1H), 1.43 (t, 3H).

Ethyl 2-({2,2,2-trifluoro-N-[({1-[(2-methoxyphenyl)methyl]piperidin-4-yl}carbamoyl)methyl]acetamido}methyl)pyridine-4-carboxylate (q)

Prepared by General Procedure B from 2-methoxybenzaldehyde and ethyl 2-[(2,2,2-trifluoro-N-{[(piperidin-4-yl)carbamoyl]methyl}acetamido)methyl]pyridine-4-carboxylate (p).

$^1$H-NMR (300 MHz, CDCl$_3$): δ 8.75 & 8.71 (2d, 1H; rotamer), 7.91-7.78 (m, 2H), 7.36 (m, 1H), 7.25 (m, 1H), 7.99-7.86 (m, 2H), 4.95 & 4.72 (2s, 2H, rotamer), 4.45 (q, 2H), 4.30 & 4.08 (2s, 2H; rotamer), 3.83 (m, 4H), 3.60 (m, 2H) 2.95 (m, 2H), 2.22 (m, 2H), 1.90 (m, 2H), 1.60 (m, 2H), 1.40 (t, 3H).

Ethyl 2-({N-[({4-[benzyl(cyclopropyl)amino]butyl}(methyl)carbamoyl)methyl]-2,2,2-trifluoroacetamido}methyl)pyridine-4-carboxylate (u)

Prepared by General Procedure B from benzaldehyde and ethyl 2-{[N-({[4-(cyclopropylamino)butyl](methyl)carbamoyl}methyl)-2,2,2-trifluoroacetamido]methyl}pyridine-4-carboxylate (t).

$^1$H NMR (300 MHz, CD$_3$OD): δ 8.70 (m, 1H), 7.83 (m, 1H), 7.77 (m, 1H), 7.30 (m, 5H), 4.83 (dd, 2H), 4.40 (m, 3H), 4.23 (m, 1H), 3.65 (m, 1H), 3.31 (m, 1H), 3.19 (m, 1H), 3.01 (m, 1H), 2.91 (m, 3H), 2.49 (m, 2H), 1.70 (m, 1H), 1.40 (m, 7H), 0.50 (m, 2H), 0.45 (m, 2H).

Ethyl 2-({[2-oxo-2-(piperidin-1-yl)ethyl]amino}methyl)pyridine-4-carboxylate (ac)

Prepared by general procedure B from ethyl 2-({ethyl[2-oxo-2-(piperidin-1-yl)ethyl]amino}methyl) pyridine-4-carboxylate and acetaldehyde to get the title compound as yellow oil.

$^1$H NMR (300 MHz, CDCl$_3$) δ 8.67 (m, 1H), 8.04 (m, 1H), 7.71 (m, 1H), 4.40 (q, 2H), 3.89 (s, 2H), 3.46 (m, 4H), 2.68 (q, 2H), 1.77-1.33 (m, 6H), 1.40 (t, 3H), 1.08 (t, 3H).

Ethyl 2-({ethyl[2-oxo-2-(piperidin-1-yl)ethyl]amino}methyl)pyridine-4-carboxylate (ab)

$^1$H NMR (300 MHz, CDCl$_3$) δ 8.68 (d, 1H), 7.93 (s, 1H), 7.71 (d, 1H), 4.40 (q, 2H), 4.02 (s, 2H), 3.56 (t, 2H), 3.47 (s, 2H), 3.28 (t, 2H), 1.58 (m, 6H), 1.40 (t, 3H).

Ethyl 2-({N-[2-(tert-butoxy)-2-oxoethyl]-2,2,2-trifluoroacetamido}methyl)pyridine-4-carboxylate (c)

General Procedure C (Formation of Triflouroacetamide and/or Trifluoroacetate)

DIPEA (1.5 equiv.) was added to a solution of the amine (or alcohol) (Ethyl 2-({[2-(tert-butoxy)-2-oxoethyl]amino}methyl)pyridine-4-carboxylate (b)) in anhydrous DCM. The mixture was stirred at 0° C. and trifluoroacetic anhydride (1.5 equiv.) was added drop wise. After addition, the mixture was allowed to warm to room temperature and stirring was continued for 2 h. The reaction was quenched with aqueous NaHCO$_3$. Aqueous work up gave the title compound.

$^1$H-NMR (300 MHz, CDCl$_3$), (rotamers): δ 8.7 (dd, 1H), 7.8 (ss, 1H), 7.7 (dd, 1H), 4.8 (ss, 2H), 4.3 (q, 2), 4.2 (ss, 2H), 1.4 (s, 9H), 1.3 (t, 3H).

Ethyl 2-[(2,2,2-trifluoro-N-{3-[(trifluoroacetyl)oxy]propyl}acetamido)methyl]pyridine-4-carboxylate (g)

Prepared by General Procedure C from ethyl 2-{[(3-hydroxypropyl)amino]methyl}pyridine-4-carboxylate (f) using 7 equiv. of DIPEA and 5 equiv. of trifluoroacetic anhydride.

$^1$H NMR (300 MHz, CDCl3), (rotamers) δ: 8.75 (two doublets, 1H), 7.80 (m, 2H), 4.80 (two singlets, 2H), 4.40 (m, 4H), 3.70 (two t, 2H), 2.20 (m, 2H), 1.45 (m, 3H).

Ethyl 2-({N-[(3R)-1-[(tert-butoxy)carbonyl]pyrrolidin-3-yl]-2,2,2-trifluoroacetamido}methyl)pyridine-4-carboxylate (l)

Prepared by General Procedure C from ethyl 2-({[(3R)-1-[(tert-butoxy)carbonyl]pyrrolidin-3-yl]amino}methyl)pyridine-4-carboxylate (k). Reaction time 12 hours. Title compound was isolated as yellow oil.

$^1$H-NMR (300 MHz, CDCl$_3$): δ 8.70 (d, 1H), 7.76 (m, 2H), 4.74-4.71 (m, 3H), 4.43 (q, 2H), 3.69-3.27 (m, 4H), 2.19-2.01 (m, 2H), 1.46 (s, 9H), 1.44 (t, 3H).

ES-MS: 446 [M+1].

2-(N-{[4-(ethoxycarbonyl)pyridin-2-yl]methyl}-2,2,2-trifluoroacetamido)acetic acid (d)

General Procedure D (Acids from Tert Butyl Esters or Amines from Tert Butoxy Carbamates)

The ester (or carbamate) (Ethyl 2-({N-[2-(tert-butoxy)-2-oxoethyl]-2,2,2-trifluoroacetamido}methyl)pyridine-4-carboxylate (c)) was dissolved in DCM and before trifluoroacetic acid (0.1-1 equiv. volume of DCM) was added. The mixture was stirred at room temperature for overnight. The solvent was evaporated in vacuum to get the title compound.

¹H-NMR (300 MHz, CD₃OD): δ 8.75 (m, 1H), 7.8 8.00 (m, 2H), 5.45, 4.99 (2s, 2H; rotamer), 4.20-4.40 (m, 4H), 1.40 (t, 3H).

Ethyl 2-({2,2,2-trifluoro-N-[(3R)-pyrrolidin-3-yl]acetamido}methyl)pyridine-4-carboxylate (m)

Prepared by General Procedure D from ethyl 2-({N-[(3R)-1-[(tert-butoxy)carbonyl]pyrrolidin-3-yl]-2,2,2-trifluoroacetamido}methyl)pyridine-4-carboxylate (l).
¹H-NMR (300 MHz, CDCl₃): δ 8.67 (d, 1H), 7.81 (s, 1H), 7.72 (d, 1H), 4.39 (q, 2H), 3.97 (d, 2H), 3.84-3.64 (m, 3H), 3.51-3.45 (m, 2H), 2.11 (m, 1H), 1.97 (m, 1H), 1.39 (t, 3H).
ES-MS: 446 [M+1]

Ethyl 2-[(2,2,2-trifluoro-N-{[(piperidin-4-yl)carbamoyl]methyl}acetamido)methyl]pyridine-4-carboxylate (p)

Prepared by General Procedure D from ethyl 2-({N-[({1-[(tert-butoxy)carbonyl]piperidin-4-yl}carbamoyl)methyl]-2,2,2-trifluoroacetamido}methyl)pyridine-4-carboxylate (o). Purification by column chromatography (MeOH/DCM and 1% NH4OH) gave the title compound as a brown foam.
¹H-NMR (300 MHz, CD₃OD): δ 8.75 (m, 1H), 7.90 (m, 2H), 5.00 & 4.90 (2s, 2H, rotamer), 4.42 (q, 2H), 4.32 & 4.12 (2s, 2H; rotamer), 3.95 (m, 1H), 3.40 (m, 2H) 3.10 (m, 2H), 2.10 (m, 2H), 1.80 (m, 2H), 1.38 (t, 3H).

Ethyl 2-({2,2,2-trifluoro-N-[2-oxo-2-(pyrrolidin-1-yl)ethyl]acetamido}methyl)pyridine-4-carboxylate (e)

General Procedure E (Formation of Esters, Amides, and Sulfonamides)

An amine (pyrrolidine) (or an alcohol or a sulfonamide) (2 equiv.) was added to a solution of an acid (2-(N-{[4-(ethoxycarbonyl)pyridin-2-yl]methyl}-2,2,2-trifluoroacetamido)acetic acid (d)) (1 equiv.) in DMF. Cooled to 0° C. before EDC HCl (1.5 equivalent) and ethyl(hydroxyl iminocyanoaectate (oxyma; 1.5 equivalent) were added. The reaction mixture was allowed to warm slowly to room temperature and stirred overnight. Aqueous work up and purification by column chromatography gave the title compound.
¹H-NMR (300 MHz, CD₃OD): δ 8.75 (m, 1H), 7.90 (s, 1H), 7.85 (m, 1H), 4.90-4.30 (two set of singlet & q, 6H, rotamer), 3.45 (m, 4H), 2.00-1.80 (m, 4H), 1.38 (t, 3H)

Ethyl 2-({N-[({1-[(tert-butoxy)carbonyl]piperidin-4-yl}carbamoyl)methyl]-2,2,2-trifluoroacetamido}methyl)pyridine-4-carboxylate (o)

Prepared by General Procedure E from tert-butyl 4-aminopiperidine-1-carboxylate and 2-(N-{[4-(ethoxycarbonyl)pyridin-2-yl]methyl}-2,2,2-trifluoroacetamido)acetic acid (d) to give the title compound as a brown foam.
¹H-NMR (300 MHz, CDCl₃): δ 8.70 & 8.60 (2d, 1H; rotamer), 7.80 (m, 2H), 4.90 & 4.78 (2s, 2H, rotamer), 4.42 (q, 2H), 4.30 & 4.10 (2s, 2H; rotamer), 4.10 (m, 1H), 2.80 (m, 2H) 2.0 (m, 2H), 1.48 (s, 9H), 1.40 (t, 3H).

Ethyl 2-[(2,2,2-trifluoro-N-{[(4-hydroxybutyl)(methyl)carbamoyl]methyl}acetamido)methyl]pyridine-4-carboxylate (r)

Prepared by General Procedure E from 4-(methylamino)butan-1-ol and 2-(N-{[4-(ethoxycarbonyl)pyridin-2-yl]methyl}-2,2,2-trifluoroacetamido)acetic acid (d).
¹H-NMR (300 MHz, CDCl₃): δ 8.70 (d, 1H), 7.90 (s 1H), 7.8 (m, 1H), 4.95 (d, 1H), 4.85 (d, 1H), 4.41 (m, 3H), 4.34 (s 1H), 3.67 (q, 2H), 3.40 (m, 1H), 3.29 (m, 1H), 2.97 (s, 3H), 1.74-1.52 (m, 5H), 1.43 (t, 3H).
ES-MS: 420 [M+1].

4-hydroxypentan-2-yl 2-({[(tert-butoxy)carbonyl]({[2-(dimethylamino)ethyl](ethyl)carbamoyl} methyl)amino}methyl)pyridine-4-carboxylate (z)

General Procedure E from 2-({[(tert-butoxy)carbonyl]({[2 (dimethylamino)ethyl] (ethyl)carbamoyl}methyl) amino}methyl)pyridine-4-carboxylic acid (x) and pentane-2,4-diol. Purification by column chromatography (10-15% MeOH/DCM gave the title compound as a brown oil.
¹H-NMR (300 MHz, CDCl3): δ 8.50 (d, 1H), 7.90 (m, 1H), 7.50 (m, 1H), 5.30 (m, 1H), 4.55 (m, 2H), 4.20, 4.10 (2s, 2H), 2.25 (2s, 6H), 1.40 (m, 12H), 1.20 (m, 6H).
ES-MS: 495 [M+1]

Ethyl 2-{[2,2,2-trifluoro-N-(3-oxopropyl)acetamido]methyl}pyridine-4-carboxylate (i)

General Procedure F (Swern Oxidation of Alcohols to Aldehydes and Ketones)

DMSO (4.0 equiv) was diluted with DCM and cooled to −78° C., oxalyl chloride (2.0 equiv) was added and the mixture was stirred for 30 minutes. Then a solution of the alcohol (ethyl 2-{[2,2,2-trifluoro-N-(3-hydroxypropyl)acetamido]methyl}pyridine-4-carboxylate (h)) in DCM was added and the mixture was stirred for another 1 h. Then Et₃N (5.0 equiv) was added and the mixtures was slowly warmed to room temperature. Aqueous work up and column chromatography gave the title compound.
¹H NMR (300 MHz, CDCl₃), (rotamers): δ 9.80 (two singlets, 1H), 8.70 (two doublets, 1H), 7.80 (m, 2H), 4.90/4.75 (two singlets, 2H), 4.45 (m, 2H), 3.95/3.75 (m, 2H), 2.90 (two t, 2H), 1.45 (m, 3H).

Ethyl 2-[(2,2,2-trifluoro-N-{[methyl (4-oxobutyl)carbamoyl]methyl}acetamido)methyl]pyridine-4-carboxylate (s)

Prepared by General Procedure F from ethyl 2-[(2,2,2-trifluoro-N-{[(4-hydroxybutyl)(methyl)carbamoyl]methyl}acetamido)methyl]pyridine-4-carboxylate (r). Purified by column chromatography (EtOAc/hexanes).
¹H-NMR (300 MHz, CDCl₃): δ 9.85 (m, 1H), 8.70 (dd, 1H), 7.9 (ss, 1H), 7.80 (dd, 1H), 4.93 (ss, 2H), 4.43 (ss, 2H), 4.35 (q, 2), 3.01 (ss, 3H), 1.44 (t, 3H).
ES-MS: 418 [M+1].

4-oxopentan-2-yl 2-({[(tert-butoxy)carbonyl]({[2-(dimethylamino)ethyl](ethyl)carbamoyl}methyl)amino}methyl)pyridine-4-carboxylate (aa)

Prepared by General Procedure F from 4-hydroxypentan-2-yl 2-({[(tert-butoxy)carbonyl]({[2-(dimethylamino)ethyl](ethyl)carbamoyl}methyl)amino}methyl)pyridine-4-carboxylate (z). Purification by column chromatography (10% MeOH/DCM) gave the title compound as brown oil.
¹H-NMR (300 MHz, CDCl3): δ 8.60 (d, 1H), 7.70 (m, 1H), 7.60 (m, 1H), 5.00 (m, 1H), 4.60 (m, 2H), 4.15, 4.00 (2s, 2H), 2.15 (s, 6H), 1.40 (m, 14H), 1.10 (m, 6H)
ES-MS: 493 [M+1]

Ethyl 2-({[(tert-butoxy)carbonyl]({[2-(dimethylamino)ethyl](ethyl)carbamoyl}methyl)amino}methyl)pyridine-4-carboxylate (v)

General Procedure G (Boc Protection of Amines)
The amine (ethyl 2-{[({[2-(dimethylamino)ethyl](ethyl)carbamoyl}methyl)amino]methyl}pyridine-4-carboxylate (#65)) (1 eq) and Boc$_2$O (1.2 eq) were dissolved in THF/H$_2$O. NaHCO$_3$ solid (4 eq) was added. The reaction mixture was stirred at room temperature overnight. After solvent removal, the residue was purified by column chromatography with a gradient of 0-10% MeOH in DCM to give the title product as yellow oil.
$^1$H-NMR (300 MHz, CDCl$_3$): δ 8.52 (m, 1H), 7.84 (m, 1H), 7.74 (m, 1H), 4.65 (m, 2H), 4.23 (m, 2H), 3.45 (m, 4H), 2.50 (m, 2H), 2.25 (m, 6H), 1.43 (m, 9H), 1.19 (m, 3H).

tert-butyl N-({[2-(dimethylamino)ethyl](ethyl)carbamoyl}methyl)-N-({4-[(pyridin-4-yl)carbamoyl]pyridin-2-yl}methyl)carbamate (y)

General Procedure H (Formation of Esters, Amides, and Sulfonamides)
Et$_3$N (3.0 eq) and propane phosphonic acid anhydride (2.0 eq) were added to a solution of an amine (pyridin-4-amine) (or an alcohol or a sulfonamide) (1.5 eq) and an acid (2-({[(tert-butoxy)carbonyl]({[2-(dimethylamino)ethyl](ethyl)carbamoyl}methyl)amino}methyl)pyridine-4-carboxylic acid (x)) (1.0 eq) in DMF. The reaction mixture was stirred for 12 h at r.t., DMF was removed in vacuum, diluted with DCM and washed with water to get the title compound as brown oil. Purified by column chromatography or used without further purification.
$^1$H-NMR (300 MHz, D$_2$O): δ 8.59 (d, 2H), 8.21 (d, 2H), 7.88 (d, 2H), 6.75 (d, 1H), 4.35-4.32 (m, 2H), 3.71-3.66 (m, 2H), 3.38-3.24 (m, 2H), 3.13-3.06 (m, 4H), 2.90 (s, 6H), 1.20-1.15 (m, 12H).

Ethyl 2-{[2,2,2-trifluoro-N-(3-hydroxypropyl)acetamido]methyl}pyridine-4-carboxylate (h)

Prepared by General Procedure A from ethyl 2-[(2,2,2-trifluoro-N-{3-[(trifluoroacetyl)oxy]propyl}acetamido)methyl]pyridine-4-carboxylate (g). Purified by flash chromatography to yield the title compound.
$^1$H NMR (300 MHz, CDCl3), (rotamers): δ 8.74 (two d, 1H), 7.80 (m, 2H), 4.85 (s, 2H), 4.45 (m, 2H), 3.65 (m, 4H), 1.90 (m, 2H), 1.45 (m, 3H).

2-({[(tert-butoxy)carbonyl]({[2-(dimethylamino)ethyl](ethyl)carbamoyl}methyl)amino}methyl)pyridine-4-carboxylic acid (x)

Prepared by General procedure A from ethyl 2-({[(tert-butoxy)carbonyl]({[2-(dimethylamino)ethyl](ethyl)carbamoyl}methyl)amino}methyl)pyridine-4-carboxylate to get the title compound as yellow solid.
$^1$H NMR (300 MHz, CD$_3$OD) δ 8.67 (m, 1H), 7.67 (m, 1H), 7.73 (m, 1H), 4.70 (m, 2H), 4.42 (m, 2H), 4.14 (m, 2H), 3.36 (m, 4H), 2.44 (m, 2H), 2.24 (m, 6H), 1.43 (m, 12H), 1.15 (m, 3H).

Amine Intermediates

Benzyl N-[(1R)-2-hydroxy-1-{methyl[3-(1-methyl-1H-imidazol-2-yl)propyl]carbamoyl}ethyl]carbamate The reaction mixture comprising of methyl[3-(1-methyl-1H-imidazol-2-yl)propyl]amine (1.1 equiv), (2R)-2-{[(benzyloxy)carbonyl]amino}-3-hydroxypropanoic acid (1.0 equiv), HATU (1.2 equiv), and DIPEA (1.4 equiv), in DMF was stirred at room temperature until TLC showed a complete reaction. Then the reaction mixture was partitioned between EtOAc/satd NaHCO$_3$. The EtOAc extract was concentrated to yield the title compound.

(2R)-2-amino-3-hydroxy-N-methyl-N-[3-(1-methyl-1H-imidazol-2-yl)propyl]propanamide A mixture of the Benzyl N-[(1R)-2-hydroxy-1-{methyl[3-(1-methyl-1H-imidazol-2-yl)propyl]carbamoyl}ethyl]carbamate and 10% Pd/C (5% by weight) in MeOH was stirred under a hydrogen atmosphere (40 PSI) until no starting material was detected by TLC. Then the mixture was filtered through a pad of celite and concentrated to yield the title compound.

2-amino-N-[2-(dimethylamino)ethyl]-N-ethylacetamide

Prepared by General Procedure E from Boc-Glycine and [2-(dimethylamino)ethyl](ethyl)amine. Subsequent treatment with HCl in MeOH gives the title product as hydrochloride.
$^1$H NMR (300 MHz, CDCl$_3$) δ 3.41 (m, 4H), 3.23 (m, 2H), 2.39 (m, 2H), 2.22 (s, 6H), 1.52 (s(br), 2H), 1.11 (m, 3H)

Alcohol Intermediates

2,2,2-trifluoro-N-(3-hydroxybutyl)acetamide

General Procedure I (Formation of Trifluoro Acetamides)
Ethyl 2,2,2-trifluoroacetate was added at 0° C. to a solution of 4-aminobutan-2-ol in MTBE. The mixture was brought to RT and stirring under nitrogen overnight. The solvent was evaporated in vacuum to yield The title compound as colorless oil.
$^1$H NMR (300 MHz, CDCl$_3$), δ 8.0 (brs, 1H), 3.95 (m, 1H), 3.6 (m, 1H), 3.3 (m, 2H), 1.75 (m, 1H), 1.6 (m, 1H), 1.2 (d, 6H).

Tert-butyl N-(3-hydroxybutyl)carbamate

Prepared by General Procedure G from 4-aminobutan-2-ol to give the title product as colorless gum.
$^1$H NMR (300 MHz, CDCl$_3$), δ ppm: 5.0 (brs, 1H), 3.7 (m, 1H), 3.4 brs, 1H), 3.2 (m, 2H), 1.6 (m, 2H), 1.4 (s, 9H), 1.2 (d, 3H).
ES-MS: 224 [M+1].

4-(methylamino)butan-2-ol

LAH was added at 0° C. to a solution of tert-butyl 3-hydroxybutylcarbamate in THF. The mixture was brought to RT and heated at 70° C. with stirring under nitrogen for 3 h. The reaction was quenched with 10% NaOH solution. Aqueous work up gave the title product as colorless oil.
$^1$H NMR (300 MHz, CDCl$_3$), δ ppm: 3.9 (m, 1H), 3.6 (brs, 2H), 2.9 (m, 1H), 2.6 (m, 1H), 2.4 (s, 3H), 1.5 (m, 2H), 1.2 (d, 3H).

2,2,2-trifluoro-N-(3-hydroxybutyl)-N-methylacetamide

Prepared by General Procedure I from 4-(methylamino)butan-2-ol to give the title product as colorless color less oil.

¹H NMR (300 MHz, CDCl₃), δ 3.8 (m, 1H), 3.7 (m, 1H), 3.2 (m, 1H), 3.2 (s, 3H), 1.7 (m, 1H), 1.6 (m, 1H), 1.2 (d, 3H).
ES-MS: 200 [M+1].

2,2,2-trifluoro-N-(3-hydroxypent-4-en-1-yl)acetamide

Prepared by General Procedure I from 5-Aminopent-1-en-3-ol to give the title compound as a brown foam.
¹H-NMR (300 MHz, CDCl₃): δ 7.50 (br s, 1H), 5.90 (m, 1H), 5.28 (d, 1H), 5.20 (d, 1H), 4.40 (m, 1H), 3.75 (m, 1H), 3.40 (m, 1H), 2.00-1.60 (m, 2H).

2,2,2-trifluoro-N-(3-oxopropyl)acetamide

Prepared by General Procedure I from 3,3-diethoxypropan-1-amine and ethyl trifluoracetate to get N-(3,3-diethoxypropyl)-2,2,2-trifluoroacetamide, which was treated with 2M HCl to get the title compound.
¹H-NMR (300 MHz, CDCl₃): δ 9.81 (s, 1H), 7.15 (br s, 1H), 3.64 (q, 2H), 2.83 (t, 2H).

trimethyl({[1-(propan-2-yloxy)ethenyl]oxy})silane

To a solution of propan-2-yl acetate (1 eq) in THF was added LDA (1.1 eq) at −78° C. The reaction mixture was stirred for 30 min and TMSCl (1 eq) added, allowed to warm at rt and stirred for 1 h. Extracted with hexane, washed with water, brine and concentrated to get the title compound.

propan-2-yl 3-hydroxy-5-(trifluoroacetamido)pentanoate

To a solution of 2,2,2-trifluoro-N-(3-oxopropyl)acetamide (1 eq) in DCM was added trimethyl({[1-(propan-2-yloxy)ethenyl]oxy})silane (1 eq) and TiCl₄ (1 eq) at −78° C. The reaction mixture was allowed to warm at rt and stirred for 1 h. Extracted with DCM, washed with water, brine and concentrated to get the title compound.
¹H-NMR (300 MHz, CDCl₃): δ 7.65 (br s, 1H), 5.05 (m, 1H), 4.19 (m, 1H), 3.35 (m, 1H), 2.46 (d, 2H), 1.85-1.61 (m, 2H), 1.25 (d, 6H).

Propan-2-yl 3-hydroxy-4-(trifluoroacetamido)butanoate

Prepared by General Procedure I from propan-2-yl 4-amino-3-hydroxybutanoate.
¹H-NMR (300 MHz, CDCl₃): δ 6.94 (br s, 1H), 5.06 (m, 1H), 4.18 (m, 1H), 3.65 (d, 1H), 3.60 (m, 1H), 3.29 (m, 1H), 2.57-2.40 (m, 2H), 1.27 (d, 6H).

Example 2: Histone Lysine Demethylase AlphaLISA Assays for IC50 Value Determination This example demonstrates the ability of compounds of the invention to inhibit the activity in vitro of tested enzymes (Table 2a).
Assays are performed analogously to the protocol described by Perkin Elmer (Roy et al. Perkin Elmer Technical Note: AlphaLISA #12, April 2011). Results are seen in Table 3.
General Method
Enzymes are dissolved in enzyme buffer and incubated for 10 min before 5 µL is added to 5 µL 3% DMSO solutions of compounds in enzyme buffer. Incubated for another 10 minutes, before 5 µL substrate solution is added and the reaction mixture is incubated at room temperature for the given period. 10 µL acceptor beads, suspended at given dilutions in Epigenetic Buffer (Perkin Elmer AL008) from stock, are added and the suspension is incubated 60 minutes in the dark at room temperature, before 10 µL suspension (at the given dilutions in Epigenetic Buffer) of streptavidin donor beads (Perkin Elmer 6760002) in Epigenetic Buffer is added. After incubation at room temperature in the dark the plates are read. Reaction conditions are seen in Table 2b.
Enzymes:

TABLE 2a

| Protein name | Vendor/source | Sequence | Expression organism |
|---|---|---|---|
| KDM2A (FBXL10) | BPS, Bioscience, US | 1-650 | Bac |
| KDM3B (JMJD1B) | BRIC | 842-1761 | Bac |
| KDM4A (JMJD2A) | BPS, Bioscience, US | 1-350 | E. coli |
| KDM4B (JMJD2B) | BPS | 2-500 | Bac |
| KDM4C (JMJD2C) | BRIC, Denmark | 1-349 | E. coli |
| KDM5 (JARID1C) | BPS | 2-1560 | Bac |
| KDM5B (PLU-1) | BRIC | 1-809 | E. coli |
| KDM6A (UTX) | BRIC | 919-1401 | E. coli |
| KDM6B (JMJD3) | BPS | 1043-end | Bac |
| KDM7 (PHF8) | BRIC | 1-1322 | Bac |
| KDM3A (JMJD1A) | BPS, Bioscience, US | 2-end | Bac |

Substrates:

```
BK9M3:
Biotin-ARTKQTAR(KMe₃)STGGKAPRKQ-NH₂ (Casio,
Denmark)

BK9M2:
Biotin-ARTKQTAR(KMe₂)STGGKAPRKQ-NH₂ (AnaSpec
64359)

BK9M1:
Biotin-ARTKQTAR(KMe₁)STGGKAPRKQ-NH₂ (AnaSpec
64358)

H3K4M3B:
H-ART(Kme3)QTARKSTGGKAPRKQLA-NH-Biotin (Casio,
Denmark)

BK27M3:
Biotin-ATKAAR(Kme3)SAPATGGVKKPHRY-NH2? (Casio,
Denmark)

BH3K36M2:
RKAAPATGGVK(Me2)KPHRYRPGTVK-(BIOTIN)?(Anaspec)

Enzyme Buffer:
50 mM Hepes (pH see table 2b), 0.003% Tween-20,
0.1% BSA; 5 µM (NH₄)₂Fe(SO₄)₂

Buffer A:
50 mM Hepes (pH see table 2b), 0.003% Tween-20,
0.1% BSA
```

Reaction Conditions

TABLE 2b

| Enzyme | Enzyme | Substrate solution | Acceptor Beads | Donor Beads | Incubation Time |
|---|---|---|---|---|---|
| KDM2B | Buffer A, pH 8.0 Final enzyme concentration: 2 nM | Buffer A, pH 8.0 + 25 µM L-Asc, 10 µM α-KG. Final substrate (BH3K36M2) conc: 50 nM | H3K36M1 (PerkinElmer Custom, 10120327RS) Diluted 1:200 from stock | Diluted 1:200 from stock | 60 min |
| KDM3A | Buffer A, pH 7.4 Final enzyme concentration: 1.6 nM | Buffer A, pH 7.4 + 25 µM L-Asc, 10 µM α-KG. Final substrate (BK9M2) conc: 100 nM | H3K9Me1 (self-conjugated) Diluted 1:200 from stock | Diluted 1:200 from stock | 60 min |
| KDM3B | Buffer A, pH 7.4 Final enzyme concentration: 0.1 nM | Buffer A, pH 7.4 + 25 µM L-Asc, 10 µM α-KG. Final substrate (BK9M2) conc: 100 nM | H3K9Me1 (self-conjugated) Diluted 1:200 from stock | Diluted 1:200 from stock | 60 min |
| KDM4A | Buffer A, pH 7.4 Final enzyme concentration: 0.2 nM | Buffer A, pH 7.4 + 25 µM L-Asc, 10 µM α-KG. Final substrate (BK9M3) conc: 100 nM | H3K9Me2 (Cat #AL117, Perkin Elmer) Diluted 1:400 from stock | Diluted 1:400 from stock | 60 min |
| KDM4B | Buffer A, pH 7.4 Final enzyme concentration: 1 nM | Buffer A, pH 7.4 + 25 µM L-Asc, 10 µM α-KG. Final substrate (BK9M3) conc: 100 nM | H3K9Me2 (Cat #AL117, Perkin Elmer) Diluted 1:400 from stock | Diluted 1:400 from stock | 60 min |
| KDM4C | Buffer A, pH 7.4 Final enzyme concentration: 1 nM | Buffer A, pH 7.4 + 25 µM L-Asc, 10 µM α-KG. Final substrate (BK9M3) conc: 200 nM | H3K9Me2 (Cat #AL117, Perkin Elmer) Diluted 1:400 from stock | Diluted 1:400 from stock | 60 min |
| KDM5B | Buffer A, pH 7.4 Final enzyme concentration: 2 nM | Buffer A, pH 7.4 + 25 µM L-Asc, 10 µM α-KG. Final substrate (H3K4M3B) conc: 200 nM | H3K4Me2-1 (Perkin Elmer AL116) Diluted 1:200 from stock | Diluted 1:200 from stock | 20 min |
| KDM5C | Buffer A, pH 7.4 Final enzyme concentration: 1 nM | Buffer A, pH 7.4 + 25 µM L-Asc, 10 µM α-KG. Final substrate (H3K4M3B) conc: 100 nM | H3K4Me2-1 (Perkin Elmer AL116) Diluted 1:200 from stock | Diluted 1:200 from stock | 30 min |
| KDM6A | Buffer A, pH 7.4 Final enzyme concentration: 2 nM | Buffer A, pH 7.4 + 25 µM L-Asc, 10 µM α-KG. Final substrate (BK27M3) conc: 100 nM | H3K27me2-1 (Perkin Elmer AL121) Diluted 1:200 from stock | Diluted 1:200 from stock | 60 min |
| KDM6B | Buffer A, pH 7.4 Final enzyme concentration: 1 nM | Buffer A, pH 7.4 + 25 µM L-Asc, 10 µM α-KG. Final substrate (BK27M3) conc: 50 nM | H3K27me2 (Perkin Elmer AL121) Diluted 1:200 from stock | Diluted 1:200 from stock | 60 min |
| KDM7 | Buffer A, pH 7.4 Final enzyme concentration: 2.5 nM | Buffer A, pH 7.4 + 25 µM L-Asc, 10 µM α-KG. Final substrate | H3K9Me1 (self-conjugated) Diluted 1:200 from stock | Diluted 1:200 from stock | 60 min |

TABLE 2b-continued

| Enzyme | Enzyme | Substrate solution | Acceptor Beads | Donor Beads | Incubation Time |
|---|---|---|---|---|---|
| | | (BK9M2) conc: 100 nM | | | |

HDME Inhibition

TABLE 3

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| (imidazole-propyl-aminomethyl pyridine carboxylic acid structure) | 2-({[3-(1H-imidazol-1-yl)propyl]amino}methyl)pyridine-4-carboxylic acid | ++ | + | +++ |  | +++ |  | + | + | + |  |
| (dimethylamino-ethyl-aminomethyl pyridine carboxylic acid structure) | 2-({[2-(dimethylamino)ethyl]amino}methyl)pyridine-4-carboxylic acid | +++ |  |  | + | +++ | +++ | + | + | + |  |
| (dihydroxypropyl-aminomethyl pyridine carboxylic acid structure) | 2-({[(2R-2,3-dihydroxypropyl]amino}methyl)pyridine-4-carboxylic acid | ++ |  |  |  |  |  |  |  | + | +++ |
| (cyclopropylmethyl-aminomethyl pyridine carboxylic acid structure) | 2-{[(cyclopropylmethyl)amino]methyl}pyridine-4-carboxylic acid | ++ |  |  |  |  |  |  |  | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| (structure) | 2-{[(cyclopropylmethyl)amino]methyl}pyridine-4-carboxylic acid | +++ | +++ | +++ | | +++ | +++ | | | + | +++ |
| (structure) | 2-({[2-(dimethylamino)ethyl](methyl)amino}methyl)pyridine-4-carboxylic acid | ++ | | | | | | | | + | ++ |
| (structure) | 2-({[methyl(prop-2-yn-1-yl)amino]methyl}pyridine-4-carboxylic acid | ++ | | | | | | | | + | ++ |
| (structure) | 2-{[(2-fluoroethyl)amino]methyl}pyridine-4-carboxylic acid | | | | | | | | | + | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 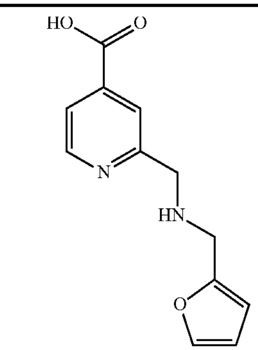 | 2-{[(furan-2-ylmethyl)amino]methyl}pyridine-4-carboxylic acid | +++ | | | | | | | | + | |
| | 2-{[(5-phenylfuran-2-yl)methyl]amino}methyl)pyridine-4-carboxylic acid | + | | | | | | | | + | ‡ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 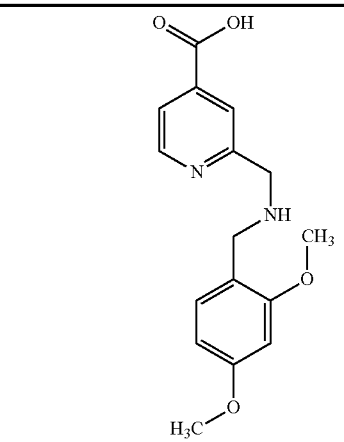 | 2-({[(2,4-dimethoxyphenyl)methyl]amino}methyl)pyridine-4-carboxylic acid | + | | | + | + | + | + | + | + | +++ |
| 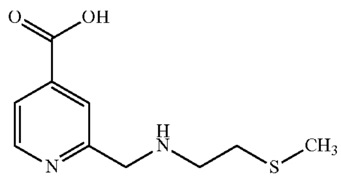 | 2-({[2-(methylsulfanyl)ethyl]amino}methyl)pyridine-4-carboxylic acid | +++ | | | | | | | | + | +++ |
| 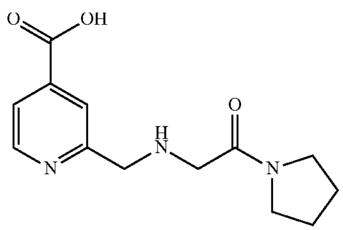 [SMILES: O=C(O)c1ccnc(CNCC(=O)N2CCCC2)c1] | 2-({[2-oxo-2-(pyrrolidin-1-yl)ethyl]amino}methyl)pyridine-4-carboxylic acid | +++ | +++ | +++ | + | +++ | +++ | ++ | + | + | +++ |
| | 2-({[butyl(methyl)carbamoyl]methyl]amino}methyl)pyridine-4-carboxylic acid | +++ | +++ | +++ | + | + | | + | + | + | +++ |

TABLE 3-continued

| Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|
| 2-({[(1-methyl-1H-1,3-benzodiazol-2-yl)methyl]amino}methyl)pyridine-4-carboxylic acid | ++ | | +++ | | +++ | +++ | | + | +++ |
| 2-[({2-[4-(2-methoxyethyl)piperazin-1-yl]-2-oxoethyl}amino)methyl]pyridine-4-carboxylic acid | +++ | | | | | | + | + | +++ |
| 2-[({[bis(prop-2-en-1-yl)carbamoyl]methyl}amino)methyl]pyridine-4-carboxylic acid | +++ | | | | | | + | + | +++ |
| 2-[({2-oxo-2-[(2R)-2-(pyrrolidin-1-ylmethyl)pyrrolidin-1-yl]ethyl}amino)methyl]pyridine-4-carboxylic acid | +++ | | | | | | + | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 2-({[(3R)-1-[(tert-butoxy)carbonyl]pyrrolidin-3-yl]amino}methyl)pyridine-4-carboxylic acid | + | | | | | | | | + | + |
| | 2-({[(3R)-1-[(tert-butoxy)carbonyl]pyrrolidin-3-yl]amino}methyl)pyridine-4-carboxylic acid | + | | | | | | | | + | + |
| 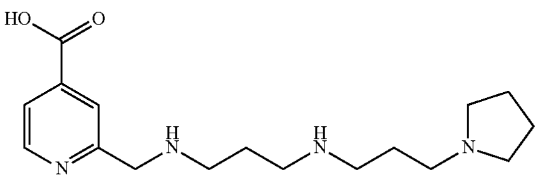 [SMILES: O=C(O)c1ccnc(CNCCCNCCCN2CCCC2)c1] | 2-{[(3-{[3-(pyrrolidin-1-yl)propyl]amino}propyl)amino]methyl}pyridine-4-carboxylic acid | +++ | | | | | | | | + | +++ |
| 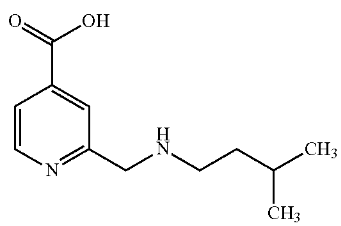 | 2-{[(3-methylbutyl)amino]methyl}pyridine-4-carboxylic acid | ++ | | | | | | | | + | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 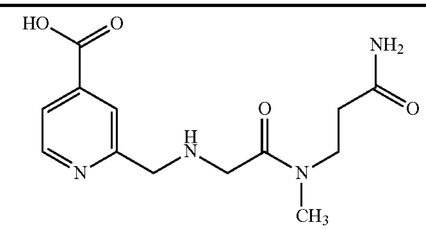 | 2-[({[(2-carbamoylethyl)(methyl)carbamoyl]methyl}amino)methyl]pyridine-4-carboxylic acid | +++ | | | | | | | + | | +++ |
| 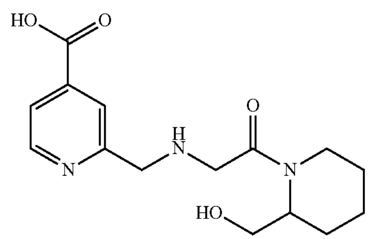 [SMILES: O=C(O)c1ccnc(CNCC(=O)N2CCCCC2CO)c1] | 2-[({2-[2-(hydroxymethyl)piperidin-1-yl]-2-oxoethyl}amino)methyl]pyridine-4-carboxylic acid | +++ | | | | | | | + | | +++ |
| 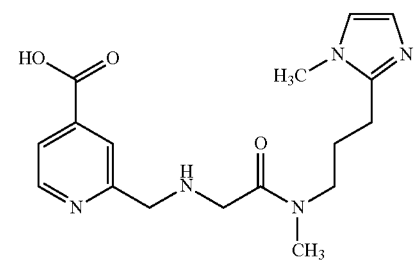 [SMILES: CN(CCCc1nccn1C)C(=O)CNCc1cc(C(=O)O)ccn1] | 2-{[({methyl[3-(1-methyl-1H-imidazol-2-yl)propyl]carbamoyl}methyl)amino]methyl}pyridine-4-carboxylic acid | +++ | | | | | | | + | | +++ |
|  | 2-{[({[(1-ethylpyrrolidin-2-yl)methyl]carbamoyl}methyl)amino]methyl}pyridine-4-carboxylic acid | +++ | | | | | | | + | | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 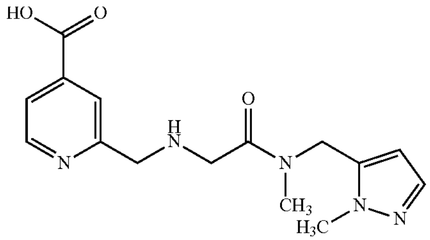 | 2-{[({methyl[(1-methyl-1H-pyrazol-5-yl)methyl]carbamoyl}methyl)amino]methyl}pyridine-4-carboxylic acid | +++ | | | | | | | | + | +++ |
| 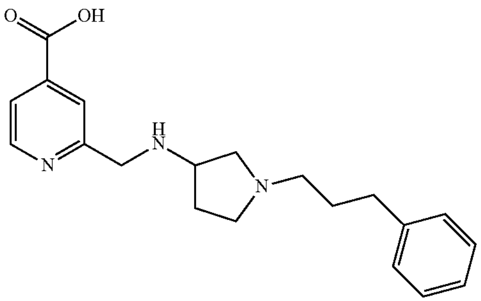 [SMILES: O=C(O)c1ccnc(CNC2CCN(CCCc3ccccc3)C2)c1] | 2-({[(3R)-1-(3-phenylpropyl)pyrrolidin-3-yl]amino}methyl)pyridine-4-carboxylic acid | + | + | +++ | + | +++ | +++ | + | | + | |
| | 2-{[({1-[(2-methoxyphenyl)methyl]piperidin-4-yl}carbamoyl)methyl]amino]methyl}pyridine-4-carboxylic acid | +++ | +++ | +++ | ++ | +++ | +++ | +++ | +++ | +++ | +++ |
| | 2-{[({1-(3-phenylpropyl)piperidin-4-yl]carbamoyl}methyl)amino]methyl}pyridine-4-carboxylic acid | +++ | | | | | | | | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 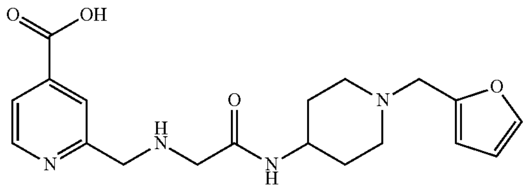 [SMILES: O=C(CNCc1cc(C(=O)O)ccn1)NC1CCN(Cc2ccco2)CC1] | 2-[({[1-(furan-2-ylmethyl)piperidin-4-yl]carbamoyl}methyl)amino]methyl}pyridine-4-carboxylic acid | +++ | | | | | | | ++ | | +++ |
| | 2-{[({1-[(5-phenylfuran-2-yl)methyl]piperidin-4-yl}carbamoyl)methyl]amino}methyl)pyridine-4-carboxylic acid | +++ | | | | | | | + | | +++ |
| 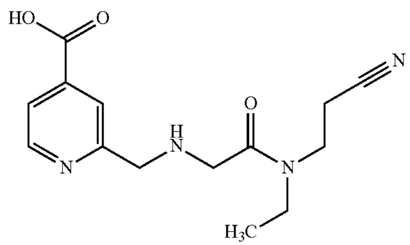 | 2-[({[(2-cyanoethyl)(ethyl)carbamoyl]methyl}amino)methyl]pyridine-4-carboxylic acid | +++ | | | | | | | + | | +++ |
| 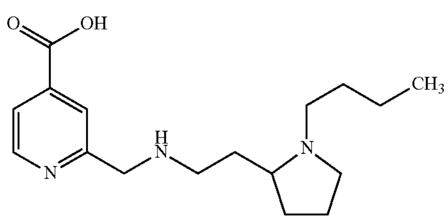 [SMILES: CCCCN1CCCC1CCNCc1cc(C(=O)O)ccn1] | 2-({[2-(1-butylpyrrolidin-2-yl)ethyl]amino}methyl)pyridine-4-carboxylic acid | | | | + | +++ | +++ | + | + | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 2-{[({1-[(3,7-dimethyloct-6-en-1-yl)pyrrolidin-3-yl]carbamoyl}methyl)amino]methyl}pyridine-4-carboxylic acid | +++ | ++ | +++ | | +++ | +++ | ++ | ++ | + | +++ |
| | 2-{[(3-{[(2-fluorophenyl)methyl](methyl)amino]propyl}amino)methyl]pyridine-4-carboxylic acid | +++ | | | | | | | | + | +++ |
| 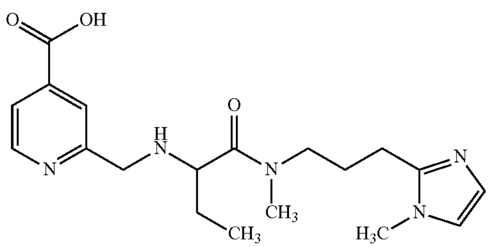 | 2-({[(1R)-2-hydroxy-1-{methyl[3-(1-methyl-1H-imidazol-2-yl)propyl]carbamoyl}ethyl]amino}methyl)pyridine-4-carboxylic acid | +++ | | | + | +++ | +++ | + | + | + | |
| 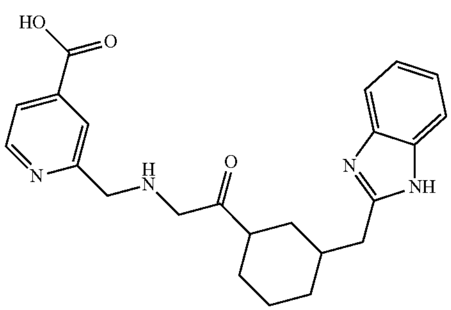 [SMILES: O=C(O)c1ccnc(CNCC(=O)C2CCCC(Cc3nc4ccccc4[nH]3)C2)c1] | 2-[({2-[3-(1H-1,3-benzodiazol-2-ylmethyl)piperidin-1-yl]-2-oxoethyl}amino)methyl]pyridine-4-carboxylic acid | +++ | | | | | | | | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 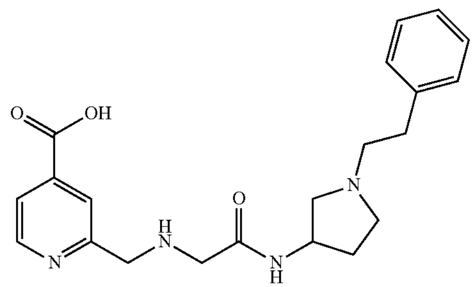 [SMILES: O=C(CNCc1cc(C(=O)O)ccn1)NC1CCN(CCc2ccccc2)C1] | 2-{[({[1-(2-phenylethyl)pyrrolidin-3-yl]carbamoyl}methyl)amino]methyl}pyridine-4-carboxylic acid | +++ | | | | | | | + | | +++ |
| 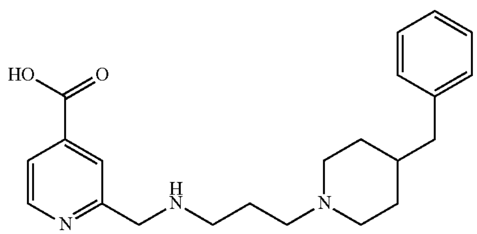 [SMILES: O=C(O)c1ccnc(CNCCCN2CCC(Cc3ccccc3)CC2)c1] | 2-({[3-(4-benzylpiperidin-1-yl)propyl]amino}methyl)pyridine-4-carboxylic acid | +++ | | | | | | | + | | +++ |
| 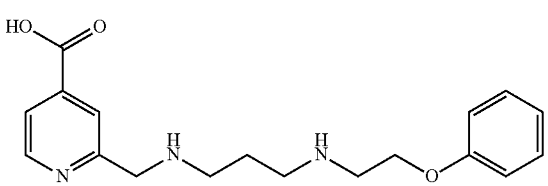 [SMILES: O=C(O)c1ccnc(CNCCCNCCOc2ccccc2)c1] | 2-[({3-[(2-phenoxymethyl)amino]propyl}amino)methyl]pyridine-4-carboxylic acid | +++ | | | | | | | + | | +++ |
| 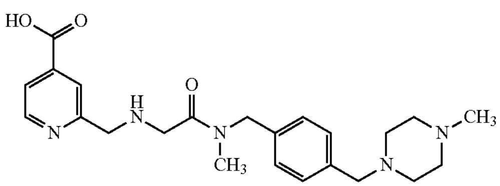 [SMILES: CN1CCN(Cc2ccc(CN(C)C(=O)CNCc3cc(C(=O)O)ccn3)cc2)CC1] | 2-{[({[methyl({4-[(4-methylpiperazin-1-yl)methyl]phenyl}methyl)carbamoyl]methyl}amino)methyl]pyridine-4-carboxylic acid | +++ | | | | | | | ‡ | | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 2-({[2-(2-benzyl]pyrrolidin-1-yl})-2-oxoethyl]amino}methyl)pyridine-4-carboxylic acid | +++ | | | | | | | | + | +++ |
| | 2-({[({4-[benzyl(cyclopropyl)amino]butyl}(methyl)carbamoyl]methyl)amino]methyl)pyridine-4-carboxylic acid | +++ | +++ | +++ | + | +++ | +++ | ++ | | | |
| 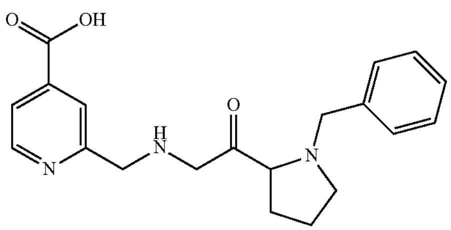 [SMILES: O=C(O)c1ccnc(CNCC(=O)C2CCCN2Cc2ccccc2)c1] | 2-[({2-[(2S)-1-benzylpyrrolidin-2-yl]ethyl}amino)methyl]pyridine-4-carboxylic acid | +++ | | | | | | | | + | +++ |
| 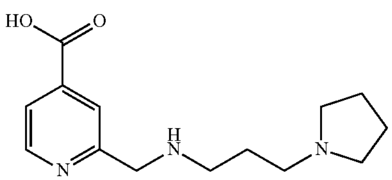 | 2-({[3-(pyrrolidin-1-yl)propyl]amino}methyl)pyridine-4-carboxylic acid | ++ | +++ | +++ | | ++ | +++ | + | + | + | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| (structure) | methyl 2-({[3-(pyrrolidin-1-yl)propyl]amino}methyl)pyridine-4-carboxylate | + | | | | | | | | | ++ |
| (structure) | 2-({[4-(diethylamino)butyl]amino}methyl)pyridine-4-carboxylic acid | +++ | ++ | +++ | + | + | +++ | + | + | | +++ |
| (structure) | 2-{[{[2-(dimethylamino)ethyl](ethyl)carbamoyl}methyl]amino}methyl]pyridine-4-carboxylic acid | +++ | | +++ | + | +++ | +++ | ++ | ++ | | +++ |
| Below | 4-methoxyphenyl 2-({[4-(diethylamino)butyl]amino}methyl)pyridine-4-carboxylate | ++ | | | | | | | + | | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| Below | 2-(ethoxycarbonyl)phenyl 2-({[4-(diethylamino)butyl]amino}methyl)pyridine-4-carboxylate | ++ | | | | | | | + | | +++ |
| 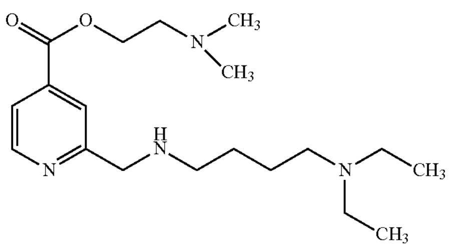 | 2-(dimethylamino)ethyl 2-({[4-(diethylamino)butyl]amino}methyl)pyridine-4-carboxylate | +++ | | | | | | | + | | +++ |
| 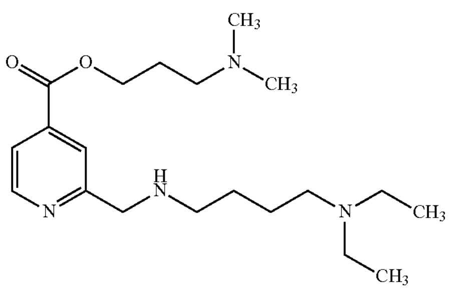 | 3-(dimethylamino)propyl 2-({[4-(diethylamino)butyl]amino}methyl)pyridine-4-carboxylate | ++ | | | | | | | + | | +++ |
| Below | {4-[(ethoxycarbonyl)amino]phenyl} methyl 2-({[4-[(ethoxycarbonyl)amino]phenyl]...} | ++ | | | | | | | + | | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| (structure) | 2-{[(diethylamino)butyl]amino}methyl) pyridine-4-carboxylate | | | | | | | | | | |
| (structure) | 2,6-dimethoxyphenyl 2-({[4-(diethylamino)butyl]amino}methyl) pyridine-4-carboxylate | ++ | | | | | | | + | | +++ |
| (structure) | 2,6-dimethylphenyl 2-({[4-(diethylamino)butyl]amino}methyl) pyridine-4-carboxylate | + | | | | | | | + | | +++ |
| Below | 4-methoxyphenyl 2-{[({2- | ++ | | | | | | | + | | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| Below | 2-(ethoxycarbonyl)phenyl 2-{[({2-(dimethylamino)ethyl](ethyl)carbamoyl}methyl)amino]methyl}pyridine-4-carboxylate | +++ | | | | | | | +++ | +++ | |
| Below | {4-[(ethoxycarbonyl)(methyl)amino]phenyl}methyl 2-({[(4-(diethylamino)butyl]amino]methyl})pyridine-4-carboxylate | + | | | | | | | +++ | +++ | |
| Below | 4-tert-butylphenyl 2-{[({2-(dimethylamino)ethyl](ethyl)carbamoyl}methyl)amino]methyl}pyridine-4-carboxylate | +++ | | | | | | | | | + |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 4-oxopentan-2-yl 2-{[({2-(dimethylamino)ethyl](ethyl)carbamoyl}methyl)amino]methyl}pyridine-4-carboxylate | +++ | | | | | | | | | +++ |
| Below | 4-(trifluoroacetamido)butan-2-yl 2-{[({2-(dimethylamino)ethyl]methyl}amino)methyl]amino]methyl}pyridine-4-carboxylate | ++ | | | | | | | | | ++ |
| Below | 4-(2,2,2-trifluoro-N-methylacetamido)butan-2-yl 2-{[({2-(dimethylamino)ethyl](ethyl)carbamoyl}methyl)amino]methyl}pyridine-4-carboxylate | +++ | | | | | | | + | | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| (structure shown) | ethyl 2-{[({[2-(dimethylamino)ethyl](ethyl)carbamoyl}methyl)amino]methyl}pyridine-4-carboxylate | | | | | | | ++ | +++ | ++ | |
| Below | 5-(trifluoroacetamido)pent-1-en-3-yl 2-{[({[2-(dimethylamino)ethyl](ethyl)carbamoyl}methyl)amino]methyl}pyridine-4-carboxylate | | | | | | | ++ | +++ | ++ | |
| Below | 5-(2,2,2-trifluoro-N-methylacetamido)pent-1-en-3-yl 2-{[({[2-(dimethylamino)ethyl](ethyl)carbamoyl}methyl)amino]methyl}pyridine-4-carboxylate | | | | | | | ++ | +++ | ++ | |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| Below | 2-(2-{[({2-(dimethylamino)ethyl](ethyl)carbamoyl}methyl)amino]methyl}pyridine-4-carbonyloxy)-3-(hexanedecanoyloxy)propyl hexadecanoate | | + | | ++ | | | | +++ | | ++ |
| Below | 1-(2-{[({2-(dimethylamino)ethyl](ethyl)carbamoyl}methyl)amino]methyl}pyridine-4-carbonyloxy)-3-(hexadecanoyloxy)propan-2-yl hexadecanoate | | | | ++ | | | | +++ | | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 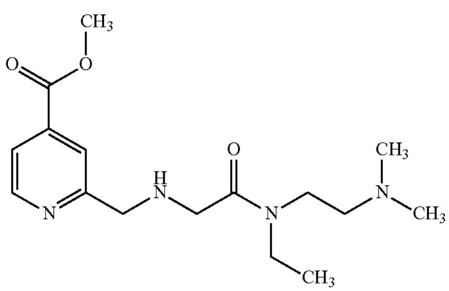 | methyl 2-{[({[2-(dimethylamino)ethyl](ethyl)carbamoyl}methyl)amino]methyl}pyridine-4-carboxylate | | | | | + | +++ | | +++ | +++ | |
| | propan-2-yl 3-(2-{[({[2-(dimethylamino)ethyl](ethyl) | | | | | | ++ | | | + | |
| Below | | | | | | | | | | | |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | carbamoyl]methyl}amino]methyl}pyridine-4-carbonyloxy)-4-(trifluoroacetamide)butanoate | | | | | | | | | | |
| | propan-2-yl 3-(2-{[({[2-(dimethylamino)ethyl][(ethyl)carbamoyl]methyl}amino]methyl}pyridine-4-carbonyloxy)-5-(trifluoroacetamido)pentanoate | | | | | | ++ | | +++ | | |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 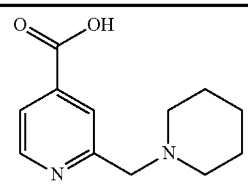 | 2-(piperidin-1-ylmethyl)pyridine-4-carboxylic acid | + | | | | | | | | | + |
| 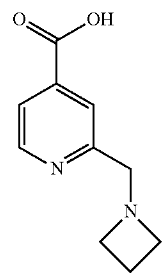 [SMILES: O=C(O)c1ccnc(CN2CCC2)c1] | 2-(azetidin-1-ylmethyl)pyridine-4-carboxylic acid | + | + | | | | | | | | + |
| 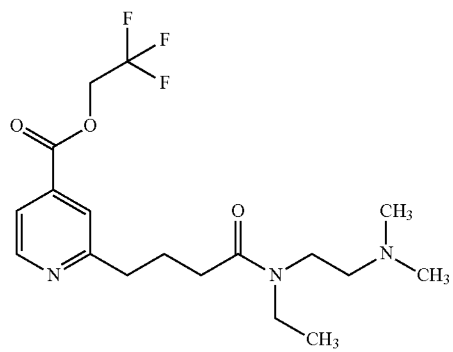 | 2,2,2-trifluoroethyl 2-{[({[2-(dimethylamino)ethyl](ethyl)carbamoyl}methyl)amino]methyl}pyridine-4-carboxylate | +++ | + | | | | | | | | +++ |
| 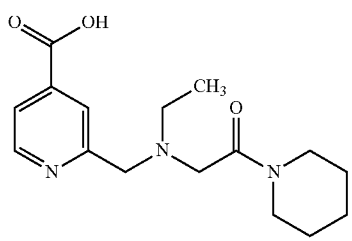 [SMILES: CCN(CC(=O)N1CCCCC1)Cc1cc(C(=O)O)ccn1] | 2-({ethyl[2-oxo-2-(piperidin-1-yl)ethyl]amino}methyl)pyridine-4-carboxylic acid | ++ | ++ | | | | | | | | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| 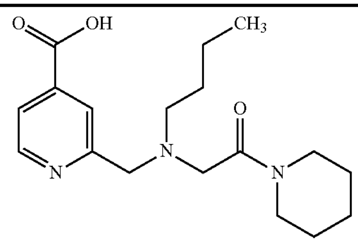 | 2-({butyl[2-oxo-2-(piperidin-1-yl)ethyl]amino}methyl)pyridine-4-carboxylic acid | + | ++ | | | | | | | | + |
| 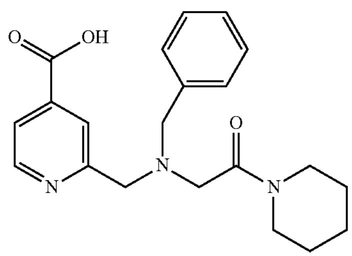 [SMILES: O=C(O)c1ccnc(CN(CC(=O)N2CCCCC2)Cc2ccccc2)c1] | 2-({benzyl[2-oxo-2-(piperidin-1-yl)ethyl]amino}methyl)pyridine-4-carboxylic acid | + | ++ | | | | | | | | + |
| Below | 2,6-bis(propan-2-yloxy)phenyl 2-{[({2-(dimethylamino)ethyl][(ethyl)carbamoyl]}methyl)amino]methyl}pyridine-4-carboxylate | ++ | | | | | | | | | ++ |

TABLE 3-continued

| Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|
| 2-{[(2-methylpropyl)[2-oxo-2-(piperidin-1-yl)ethyl]amino]methyl}pyridine-4-carboxylic acid | + | ++ | | | | | | +++ | +++ | + |
| 2-({[2-oxo-2-(piperidin-1-yl)ethyl](propyl)amino}methyl)pyridine-4-carboxylic acid | + | ++ | | | | | | +++ | +++ | ++ |
| 2-({[2-oxo-2-(piperidin-1-yl)ethyl](propan-2-yl)amino}methyl)pyridine-4-carboxylic acid | + | ++ | | | | | | +++ | +++ | + |
| 2-fluoroethyl 2-{[({2-(dimethylamino)ethyl][(ethyl)carbamoyl]methyl}amino)methyl]}pyridine-4-carboxylate | ++ | + | | | | | | +++ | +++ | +++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 2,2-difluoroethyl 2-{[({2-(dimethylamino)ethyl][(ethyl)carbamoyl]methyl}amino]methyl})pyridine-4-carboxylate | +++ | + | | | | | | | +++ | +++ |
| 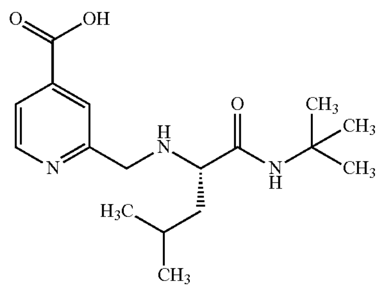 [SMILES: CC(C)C[C@H](NCc1cc(C(=O)O)ccn1)C(=O)NC(C)(C)C] | 2-({[(1S)-1-(tert-butylcarbamoyl)-3-methylbutyl]amino}methyl)pyridine-4-carboxylic acid | + | ++ | | | | | | | ++ | + |
| 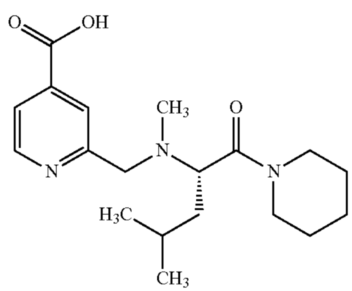 [SMILES: CC(C)C[C@@H](C(=O)N1CCCCC1)N(C)Cc1cc(C(=O)O)ccn1] | 2-({methyl[(2S)-4-methyl-1-oxo-1-(piperidin-1-yl)pentan-2-yl]amino}methyl)pyridine-4-carboxylic acid | + | | | | | | | | | + |

TABLE 3-continued

| Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|
| 2-{[({2-(dimethylamino)ethyl][(ethyl)carbamoyl]methyl})amino]methyl}-N-methanesulfonyl-N-methylpyridine-4-carboxamide | +++ | ++ | | | | | | + | | +++ |
| N-[2-(dimethylamino)ethyl]-N-ethyl-2-({[4-(2-oxo-1,3-oxazolidine-3-carbonyl)pyridin-2-yl]methyl}amino)acetamide | +++ | + | | | | | | | | ++ |
| 2-{[({2-(dimethylamino)ethyl][(ethyl)carbamoyl]methyl})amino]methyl}-N-(pyridin-4-yl)pyridine-4-carboxamide | ++ | | | | | | | | | ++ |

TABLE 3-continued

| Structure | Name | GASC1 | FBXL10 | JARID1C | JMJD1B | JMJD2A | JMJD2B | JMJD3 | PHF8 | UTX | PLU1 |
|---|---|---|---|---|---|---|---|---|---|---|---|
| | 2-{[([2-(dimethylamino)ethyl](ethyl)carbamoyl]methyl)amino]methyl}-N-(5-methyl-1,3,4-oxadiazol-2-yl)pyridine-4-carboxamide | +++ | | | | | | | | | +++ |
| | 2-{[([2-(dimethylamino)ethyl](ethyl)carbamoyl]methyl)amino]methyl}-N-(1-methyl-1H-pyrazol-5-yl)pyridine-4-carboxamide | +++ | | | | | | | | | +++ |
| Below | 2-{[([2-(dimethylamino)ethyl](ethyl)carbamoyl]methyl)amino]methyl}-N-(1,3-oxadiazol-2-yl)pyridine-4-carboxamide | +++ | | | | | | | | | |
| Below | 2-{[([2-(dimethylamino)ethyl](ethyl)carbamoyl]methyl)amino]methyl}-N-(1-methyl-1H-imidazol-2-yl)pyridine-4-carboxamide | ++ | | | | | | | +++ | | +++ |

(a) ++++: IC50 < 100 nM; +++: 100 nM ≤ IC50 ≤ 1000 nM; +: IC50 ≥ 1000 nM

Example 3: Histone Lysine Demethylase Immunofluorescence Assays for IC50 Value Determination in Cell Histone Lysine Demethylase Immunofluorescence Assays for IC50 Value Determination, Non-Transfected Cells This example demonstrates the ability of compounds of the invention to inhibit demethylation of H3K4 in a human osteosarcoma cancer cell line.

General Method

U2OS cells were harvested and seeded into multi well plates into media containing compound. The media used was DMEM containing 5% FBS and pen/strep. 20 hours after incubation of cells with compounds, the cells were washed once in PBS, harvested by fixation with formaldehyde 4% aqueous solution, and washed 2 times in PBS. Subsequently, the cells were permeabilized in PBS with 0.2% Triton X-100 for 10 min at room temperature. Blocking was performed in PBS with 0.2% Triton X-100 and 5% FBS for 45 min at room temperature. The cells were incubated with αH3K4me3 primary antibody (Cell Signaling, #9751S) diluted 1:1000 in blocking solution over night at 4° C. After incubation with primary antibody, the cells were washed 3 times with PBS, incubated with secondary antibody diluted 1:1000 (Alexa fluor 594 goat anti rabbit IgG, Invitrogen, A11012) and Hoechst, 20 μg/ml (Sigma, 33342) in blocking solution, and washed again 3 times with PBS. Finally, PBS was added and high throughput imaging and analysis were performed by an IN Cell Analyzer 1000 (GE Healthcare). The IC50 values seen in Table 4 were based on an average measure of the staining of the H3K4me3 mark in cells.

Histone Lysine Demethylase Inhibition

TABLE 4

| Structure | Name | IC50 |
|---|---|---|
| 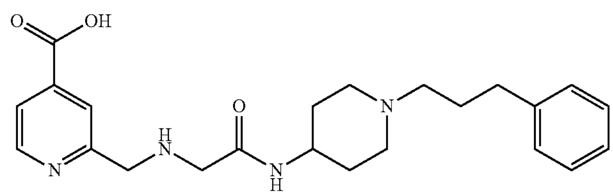 [SMILES: O=C(CNCc1cc(C(=O)O)ccn1)NC1CCN(CCCc2ccccc2)CC1] | 2-{[({[1-(3-phenylpropyl)piperidin-4-yl]carbamoyl}methyl)amino]methyl}pyridine-4-carboxylic acid | + |
| 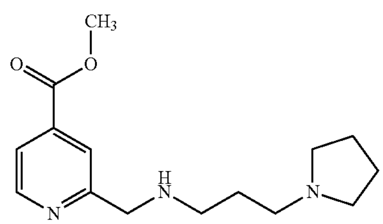 [SMILES: COC(=O)c1ccnc(CNCCCN2CCCC2)c1] | methyl 2-({[3-(pyrrolidin-1-yl)propyl]amino}methyl)pyridine-4-carboxylate | ++ |
| 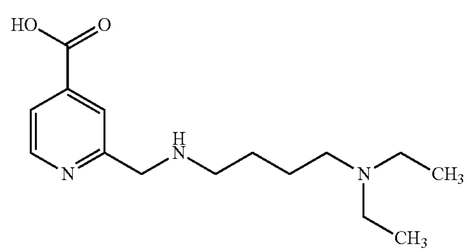 [SMILES: CCN(CC)CCCCNCc1cc(C(=O)O)ccn1] | 2-({[4-(diethylamino)butyl]amino}methyl)pyridine-4-carboxylic acid | ++ |
| 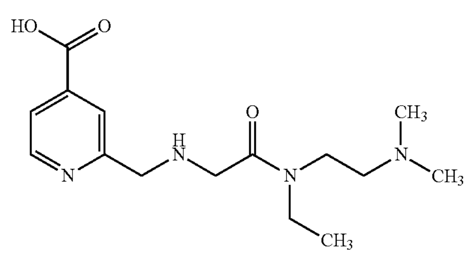 [SMILES: CCN(CCN(C)C)C(=O)CNCc1cc(C(=O)O)ccn1] | 2-{[({[2-(dimethylamino)ethyl](ethyl)carbamoyl}methyl)amino]methyl}pyridine-4-carboxylic acid | ++ |

TABLE 4-continued

| Structure | Name | IC50 |
|---|---|---|
| 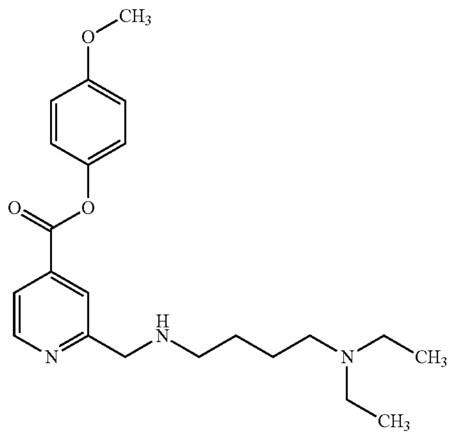 [SMILES: CCN(CC)CCCCNCc1cc(C(=O)Oc2ccc(OC)cc2)ccn1] | 4-methoxyphenyl 2-({[4-(diethylamino)butyl]amino}methyl)pyridine-4-carboxylate | +++ |
| 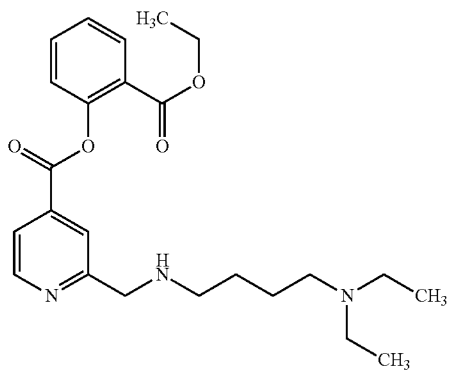 [SMILES: CCOC(=O)c1ccccc1OC(=O)c1ccnc(CNCCCCN(CC)CC)c1] | 2-(ethoxycarbonyl)phenyl 2-({[4-(diethylamino)butyl]amino}methyl)pyridine-4-carboxylate | +++ |
| 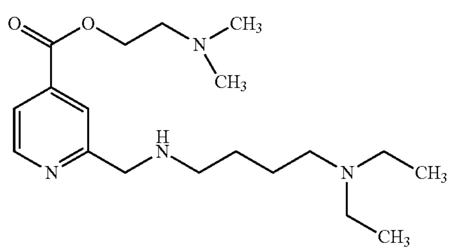 [SMILES: CCN(CC)CCCCNCc1cc(C(=O)OCCN(C)C)ccn1] | 2-(dimethylamino)ethyl 2-({[4-(diethylamino)butyl]amino}methyl)pyridine-4-carboxylate | ++ |
| 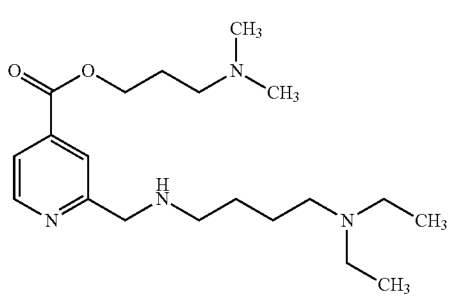 [SMILES: CCN(CC)CCCCNCc1cc(C(=O)OCCCN(C)C)ccn1] | 3-(dimethylamino)propyl 2-({[4-(diethylamino)butyl]amino}methyl)pyridine-4-carboxylate | ++ |

TABLE 4-continued

| Structure | Name | IC50 |
|---|---|---|
| 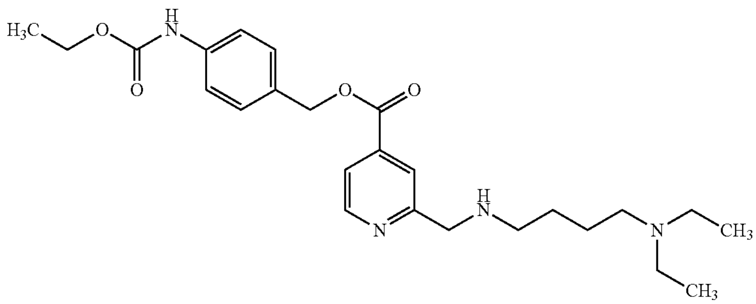 [SMILES: CCOC(=O)Nc1ccc(COC(=O)c2ccnc(CNCCCCN(CC)CC)c2)cc1] | {4-[(ethoxycarbonyl)amino]phenyl}methyl 2-({[4-(diethylamino)butyl]amino}methyl)pyridine-4-carboxylate | +++ |
| | 2,6-dimethoxyphenyl 2-({[4-(diethylamino)butyl]amino}methyl)pyridine-4-carboxylate | +++ |
| | 2,6-dimethoxyphenyl 2-({[4-(diethylamino)butyl]amino}methyl)pyridine-4-carboxylate | +++ |
| | 4-methoxyphenyl 2-{[({2-(dimethylamino)ethyl](ethyl)carbamoyl}methyl)amino]methyl}pyridin-4-carboxylate | +++ |

TABLE 4-continued

| Structure | Name | IC50 |
|---|---|---|
| 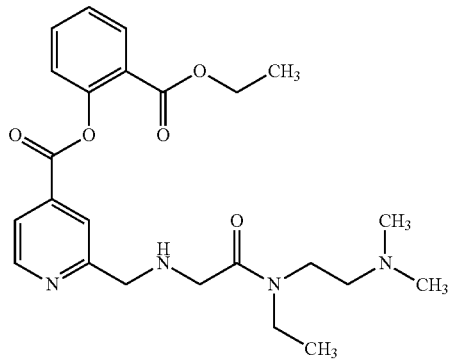 [SMILES: CCOC(=O)c1ccccc1OC(=O)c1ccnc(CNCC(=O)N(CC)CCN(C)C)c1] | 2-(ethoxycarbonyl)phenyl 2-{[({[2-(dimethylamino)ethyl](ethyl)carbamoyl}methyl)amino]methyl}pyridine-4-carboxylate | +++ |
| 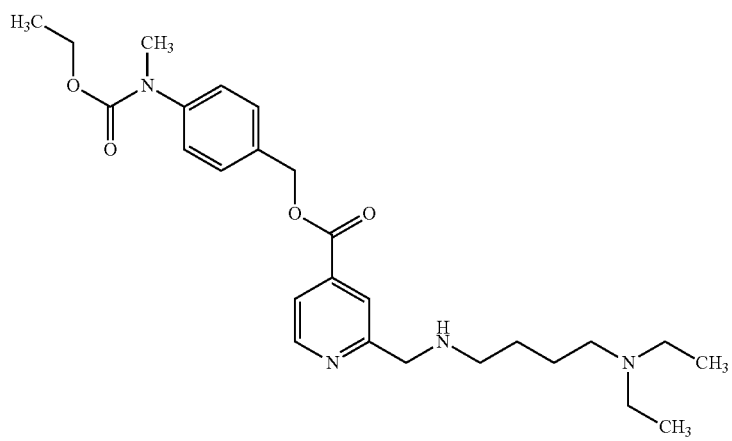 [SMILES: CCOC(=O)N(C)c1ccc(COC(=O)c2ccnc(CNCCCCN(CC)CC)c2)cc1] | {4-[(ethoxycarbonyl)(methyl)amino]phenyl}methyl 2-({[4-(diethylamino)butyl]amino}pyridine-4-carboxylate | +++ |
| 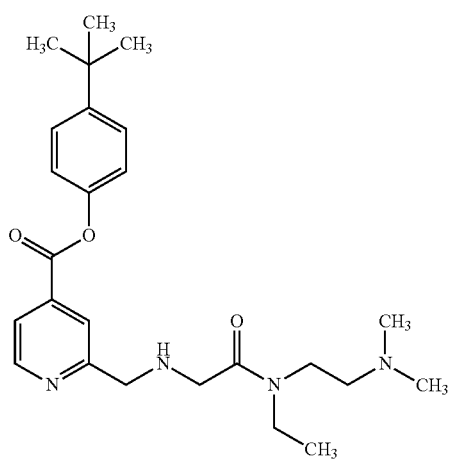 [SMILES: CCN(CCN(C)C)C(=O)CNCc1cc(C(=O)Oc2ccc(C(C)(C)C)cc2)ccn1] | 4-tert-butylphenyl 2-{[({[2-(dimethylamino)ethyl](ethyl)carbamoyl}methyl)amino]methyl}pyridine-4-carboxylate | +++ |
| 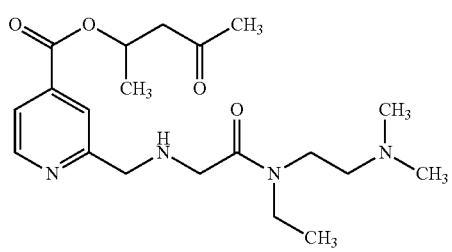 [SMILES: CCN(CCN(C)C)C(=O)CNCc1cc(C(=O)OC(C)CC(C)=O)ccn1] | 4-oxopentan-2-yl 2-{[({[2-(dimethylamino)ethyl](ethyl)carbamoyl}methyl)amino]methyl}pyridine-4-carboxylate | +++ |

TABLE 4-continued

| Structure | Name | IC50 |
|---|---|---|
| 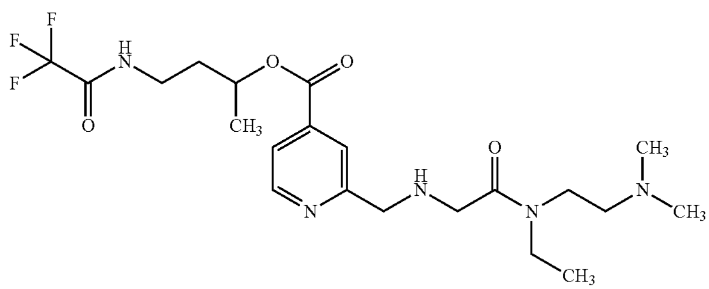 [SMILES: CCN(CCN(C)C)C(=O)CNCc1cc(C(=O)OC(C)CCNC(=O)C(F)(F)F)ccn1] | 4-(trifluoroacetamido)butan-2-yl 2-{[({[2-(dimethylamino)ethyl](ethyl)carbamoyl}methyl)amino]methyl}pyridin-4-carboxylate | +++ |
| 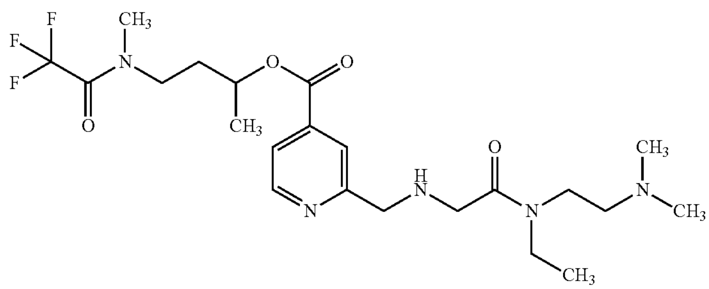 [SMILES: CCN(CCN(C)C)C(=O)CNCc1cc(C(=O)OC(C)CCN(C)C(=O)C(F)(F)F)ccn1] | 4-(2,2,2-trifluoro-N-methylacetamido)butan-2-yl 2-{[({[2-(dimethylamino)ethyl](ethyl)carbamoyl}methyl)amino]methyl}pyridine-4-carboxylate | +++ |
| 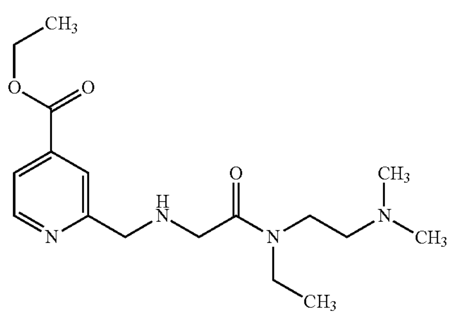 [SMILES: CCOC(=O)c1ccnc(CNCC(=O)N(CC)CCN(C)C)c1] | ethyl 2-{[({[2-(dimethylamino)ethyl](ethyl)carbamoyl}methyl)amino]methyl}pyridine-4-carboxylate | +++ |
| 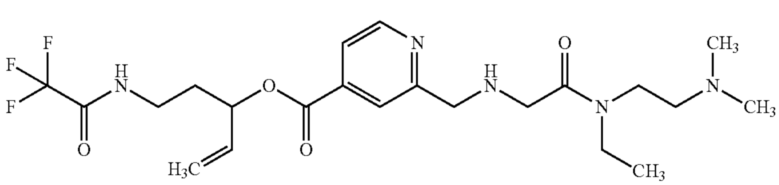 [SMILES: C=CC(CCNC(=O)C(F)(F)F)OC(=O)c1ccnc(CNCC(=O)N(CC)CCN(C)C)c1] | 5-(trifluoroacetamido)pent-1-en-3-yl 2-{[({[2-(dimethylamino)ethyl](ethyl)carbamoyl}methyl)amino]methyl}pyridine-4-carboxylate | +++ |
| 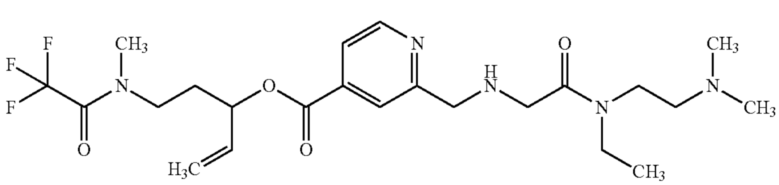 [SMILES: C=CC(CCN(C)C(=O)C(F)(F)F)OC(=O)c1ccnc(CNCC(=O)N(CC)CCN(C)C)c1] | 5-(2,2,2-trifluoro-N-methylacetamido)pent-1-en-3-yl 2-{[({[2-(dimethylamino)ethyl](ethyl)carbamoyl}methyl)amino]methyl}pyridine-4-carboxylate | +++ |

TABLE 4-continued

| Structure | Name | IC50 |
|---|---|---|
| 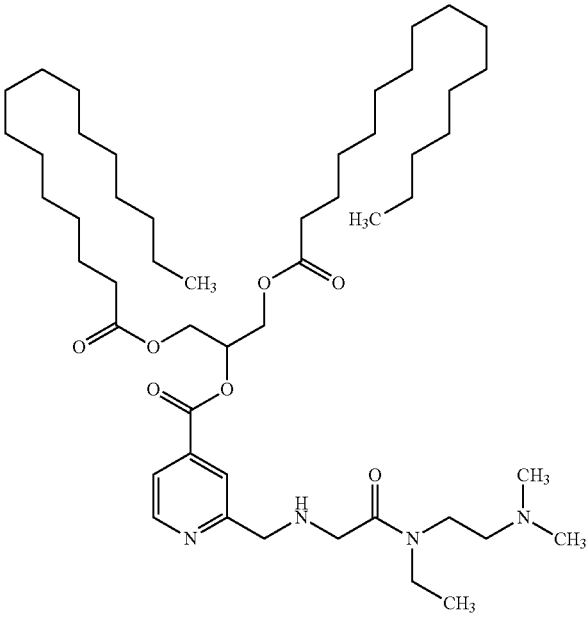 [SMILES: CCCCCCCCCCCCCCCC(=O)OCC(COC(=O)CCCCCCCCCCCCCCC)OC(=O)c1ccnc(CNCC(=O)N(CC)CCN(C)C)c1] | 2-(2-{[({[2-(dimethylamino)ethyl](ethyl)carbamoyl}methyl)amino]methyl}pyridine-4-carbonyloxy)-3-(hexadecanoyloxy)propyl hexadecanoate | +++ |
| 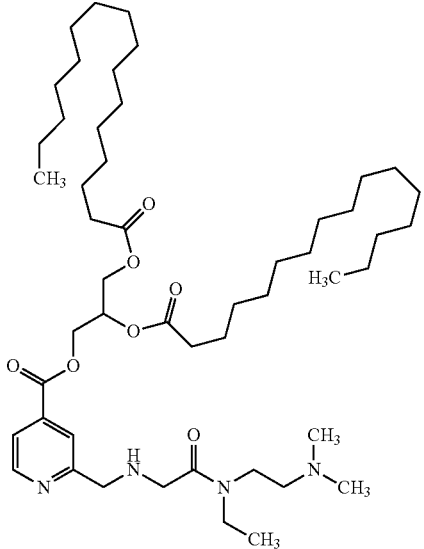 [SMILES: CCCCCCCCCCCCCCCC(=O)OCC(COC(=O)c1ccnc(CNCC(=O)N(CC)CCN(C)C)c1)OC(=O)CCCCCCCCCCCCCCC] | 1-(2-{[({[2-(dimethylamino)ethyl](ethyl)carbamoyl}methyl)amino]methyl}pyridine-4-carbonyloxy)-3-(hexadecanoyloxy)propan-2-yl hexadecanoate | +++ |
| 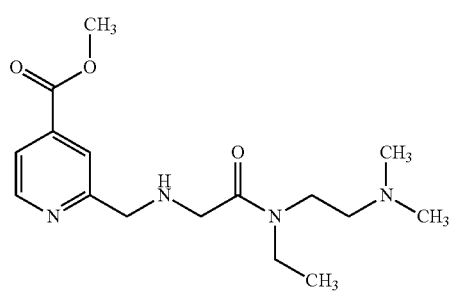 [SMILES: CCN(CCN(C)C)C(=O)CNCc1cc(C(=O)OC)ccn1] | methyl 2-{[({[2-(dimethylamino)ethyl](ethyl)carbamoyl}methyl)amino]methyl}pyridine-4-carboxylate | +++ |

TABLE 4-continued

| Structure | Name | IC50 |
|---|---|---|
| 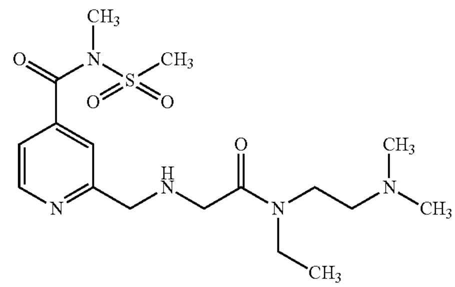 [SMILES: CCN(CCN(C)C)C(=O)CNCc1cc(C(=O)N(C)S(C)(=O)=O)ccn1] | 2-{[({[2-(dimethylamino)ethyl](ethyl)carbamoyl}methyl)amino]methyl}-N-methanesulfonyl-N-methylpyridine-4-carboxamide | ++ |
| 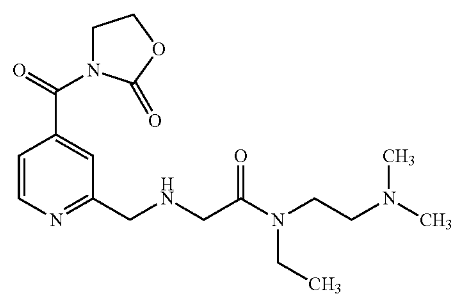 [SMILES: CCN(CCN(C)C)C(=O)CNCc1cc(C(=O)N2CCOC2=O)ccn1] | N-[2-(dimethylamino)ethyl]-N-ethyl-2-({[4-(2-oxo-1,3-oxazolidine-3-carbonyl)pyridin-2-yl]methyl}amino)acetamide | ++ |
| 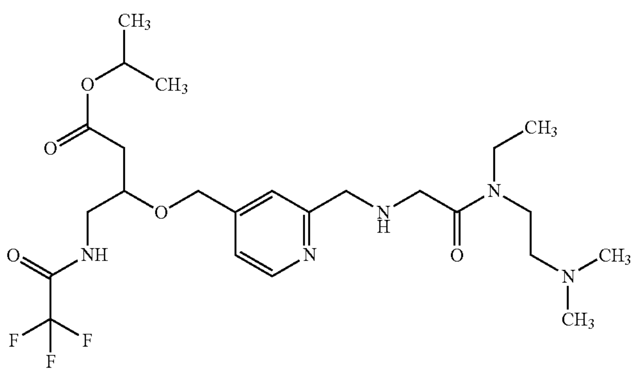 [SMILES: CCN(CCN(C)C)C(=O)CNCc1cc(COC(CNC(=O)C(F)(F)F)CC(=O)OC(C)C)ccn1] | propan-2-yl 3-(2-{[({[2-(dimethylamino)ethyl](ethyl)carbamoyl}methyl)amino]methyl}pyridine-4-carbonyloxy)-4-(trifluoroacetamido)butanoate | +++ |
| 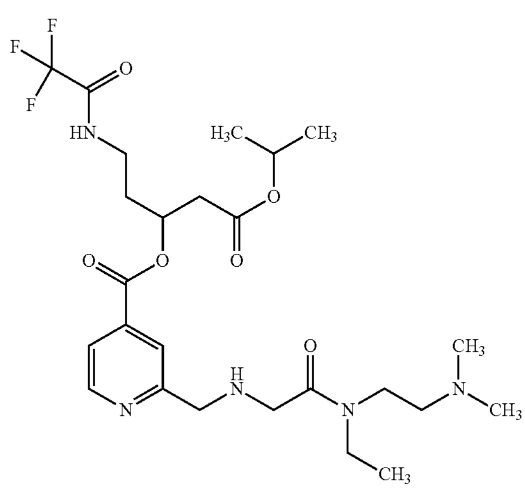 [SMILES: CCN(CCN(C)C)C(=O)CNCc1cc(C(=O)OC(CCNC(=O)C(F)(F)F)CC(=O)OC(C)C)ccn1] | propan-2-yl 3-(2-{[({[2-(dimethylamino)ethyl](ethyl)carbamoyl}methyl)amino]methyl}pyridine-4-carbonyloxy)-5-(trifluoroacetamido)pentanoate | +++ |

TABLE 4-continued

| Structure | Name | IC50 |
|---|---|---|
| 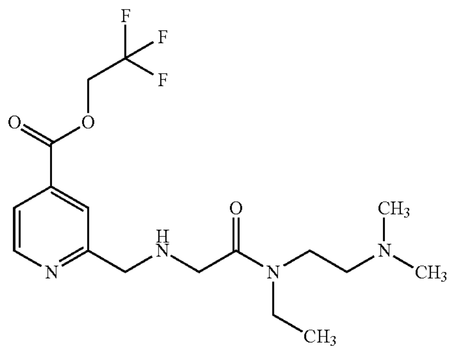 [SMILES: CCN(CCN(C)C)C(=O)CNCc1cc(C(=O)OCC(F)(F)F)ccn1] | 2,2,2-trifluoroethyl 2-{[({[2-(dimethylamino)ethyl](ethyl)carbamoyl}methyl)amino]methyl}pyridine-4-carboxylate | +++ |
| 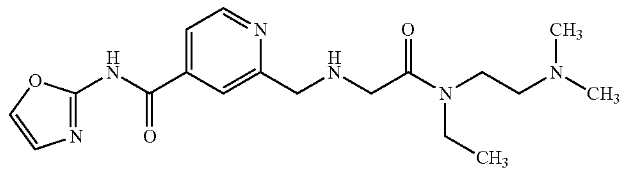 [SMILES: CCN(CCN(C)C)C(=O)CNCc1cc(C(=O)Nc2ncco2)ccn1] | 2-{[({[2-(dimethylamino)ethyl](ethyl)carbamoyl}methyl)amino]methyl}-N-(1,3-oxazol-2-yl)pyridine-4-carboxamide | ++ |
| 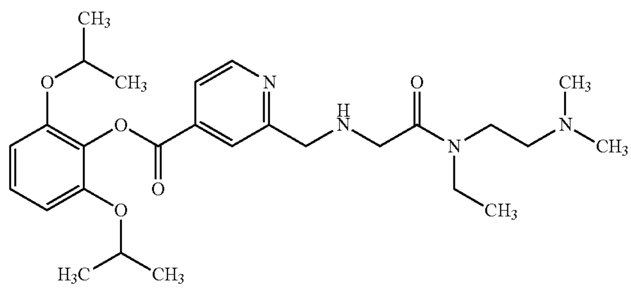 [SMILES: CCN(CCN(C)C)C(=O)CNCc1cc(C(=O)Oc2c(OC(C)C)cccc2OC(C)C)ccn1] | 2,6-bis(propan-2-yloxy)phenyl 2-{[({[2-(dimethylamino)ethyl](ethyl)carbamoyl}methyl)amino]methyl}pyridine-4-carboxylate | ++ |
| 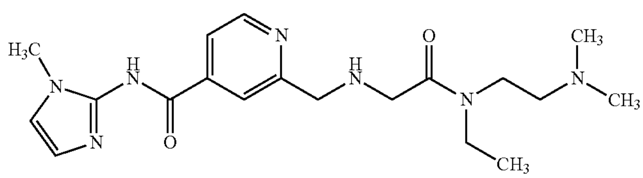 [SMILES: CCN(CCN(C)C)C(=O)CNCc1cc(C(=O)Nc2nccn2C)ccn1] | 2-{[({[2-(dimethylamino)ethyl](ethyl)carbamoyl}methyl)amino]methyl}-N-(1-methyl-1H-imidazol-2-yl)pyridine-4-carboxamide | ++ |
| 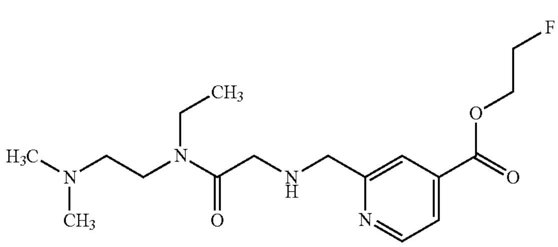 [SMILES: CCN(CCN(C)C)C(=O)CNCc1cc(C(=O)OCCF)ccn1] | 2-fluoroethyl 2-{[({[2-(dimethylamino)ethyl](ethyl)carbamoyl}methyl)amino]methyl}pyridine-4-carboxylate | +++ |
| 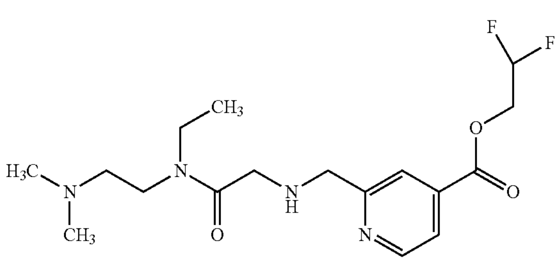 [SMILES: CCN(CCN(C)C)C(=O)CNCc1cc(C(=O)OCC(F)F)ccn1] | 2,2-difluoroethyl 2-{[({[2-(dimethylamino)ethyl](ethyl)carbamoyl}methyl)amino]methyl}pyridine-4-carboxylate | +++ |

(a) +++: IC50 <1 µM; ++: 1 µM ≤ IC50 ≤ 50 µM; +: IC50 > 50 µM

Example 4: Cell Proliferation Assays for EC50 Value Determination

This example demonstrates the ability of the compounds of the invention to inhibit the proliferation of a human breast cancer cell line.

General Method

MCF7 cells were seeded at 1250 cells/well in 50 μl medium/well in black 96 well plates. Cells were incubated for 24 hours before addition of compound. Compounds were diluted in complete medium (50 μl/well) and added to the plates in duplicates. The total volume of medium in the wells was 100 μl, and the final concentration of DMSO 0.5%. Complete medium used was DMEM with GlutaMAX containing 10% FBS and pen/strep.

120 hours after addition of compounds, the plates were harvested and analyzed by ATPlite 1 Step (Perkin Elmer, cat no 6016739) according to the manufactures recommendation. Briefly, 100 μl ATP lite solution was added to each well, plates were vortexed at 700 rpm 2 minutes, followed by 20 minutes incubation in the dark, and then analyzed for luminescence on EnSpire 2300 Mulitilabel reader (Perkin Elmer). EC50 values were calculated using GraphPad Prism 6. Results are seen in Table 5.

TABLE 5

| Structure | Name | EC50 |
|---|---|---|
| 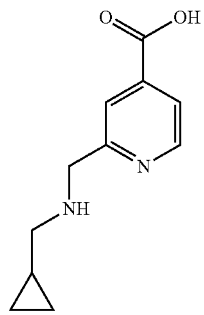 [SMILES: O=C(O)c1ccnc(CNCC2CC2)c1] | 2-{[(cyclopropylmethyl)amino]methyl}pyridine-4-carboxylic acid | ++ |
| 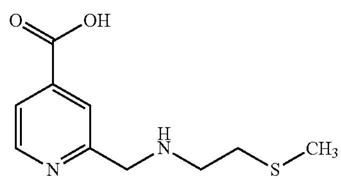 | 2-({[2-(methylsulfanyl)ethyl]amino}methyl)pyridine-4-carboxylic acid | ++ |
| 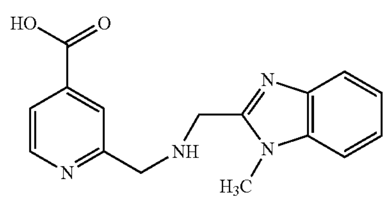 [SMILES: Cn1c(CNCc2cc(C(=O)O)ccn2)nc2ccccc21] | 2-({[(1-methyl-1H-1,3-benzodiazol-2-yl)methyl]amino}methyl)pyridine-4-carboxylic acid]} | ++ |
| 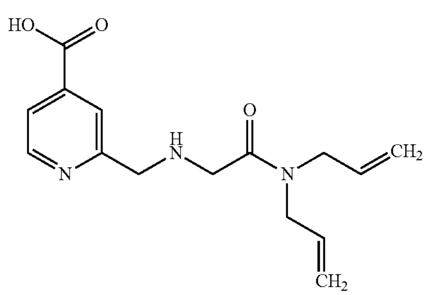 [SMILES: C=CCN(CC=C)C(=O)CNCc1cc(C(=O)O)ccn1] | 2-[({[bis(prop-2-en-1-yl)carbamoyl]methyl}amino)methyl]pyridine-4-carboxylic acid | ++ |
| 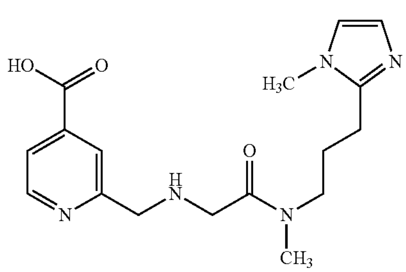 [SMILES: CN(CCCc1nccn1C)C(=O)CNCc1cc(C(=O)O)ccn1] | 2-{[({methyl[3-(1-methyl-1H-imidazol-2-yl)propyl]carbamoyl}methyl)amino]methyl}pyridine-4-carboxylic acid | ++ |

TABLE 5-continued

| Structure | Name | EC50 |
|---|---|---|
| 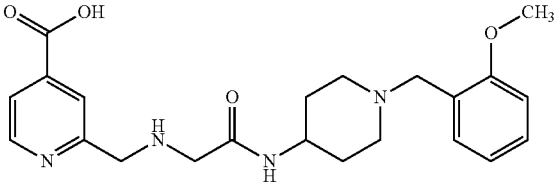 [SMILES: COc1ccccc1CN1CCC(NC(=O)CNCc2cc(C(=O)O)ccn2)CC1] | 2-({[({(1-[(2-methoxy[henyl)methyl]piperidin-4-yl}carbamoyl)methyl]amino}methyl)pyridine-4-carboxylic acid | ++ |
| 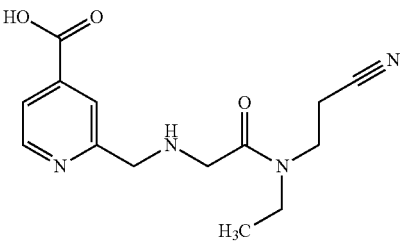 | 2-[({[(2-cyanoethyl)(ethyl)carbamoyl]methyl}amino)methyl]pyridine-4-carboxylic acid | ++ |
| 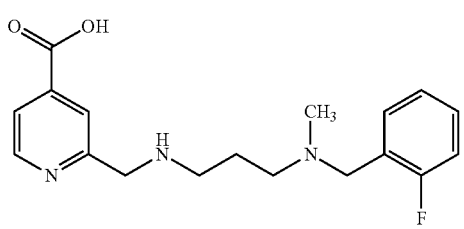 [SMILES: CN(CCCNCc1cc(C(=O)O)ccn1)Cc1ccccc1F] | 2-{[(3-{[(2-fluorophenyl)methyl](methyl)amino}propyl)amino]methyl}pyridine-4-carboxylic acid | ++ |
| 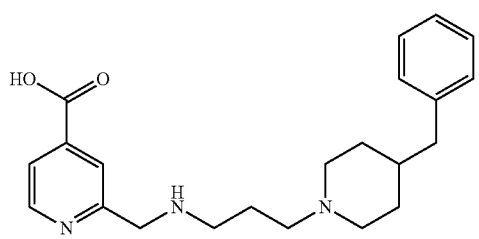 [SMILES: O=C(O)c1ccnc(CNCCCN2CCC(Cc3ccccc3)CC2)c1] | 2-({[3-(4-benzylpiperidin-1-yl)propyl]amino}methyl)pyridine-4-carboxylic acid | ++ |
| 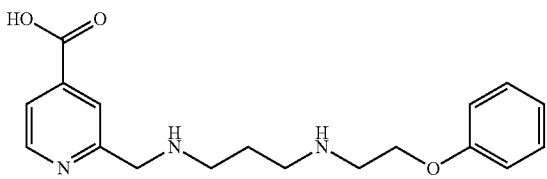 [SMILES: O=C(O)c1ccnc(CNCCCNCCOc2ccccc2)c1] | 2-[({3-[(2-phenoxyethyl)amino]propyl}amino)methyl]pyridine-4-carboxylic acid | ++ |
| 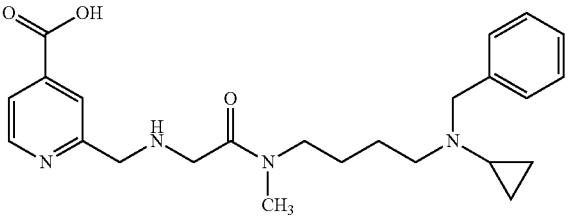 [SMILES: CN(CCCCN(Cc1ccccc1)C1CC1)C(=O)CNCc1cc(C(=O)O)ccn1] | 2-({[({4-[benzyl(cyclopropyl)amino]butyl}(methyl)carbamoyl)methyl]amino}methyl)pyridine-4-carboxylic acid | + |
| 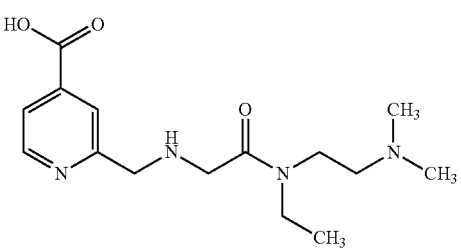 [SMILES: CCN(CCN(C)C)C(=O)CNCc1cc(C(=O)O)ccn1] | 2-{[({[2-(dimethylamino)ethyl](ethyl)carbamoyl}methyl)amino]methyl}pyridine-4-carboxylic acid | ++ |

TABLE 5-continued

| Structure | Name | EC50 |
|---|---|---|
| 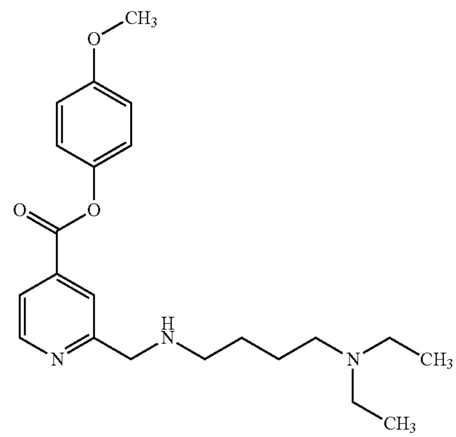 [SMILES: CCN(CC)CCCCNCc1cc(C(=O)Oc2ccc(OC)cc2)ccn1] | 4-methoxyphenyl 2-({[4-(diethylamino)butyl]amino}methyl)pyridine-4-carboxylate | +++ |
| 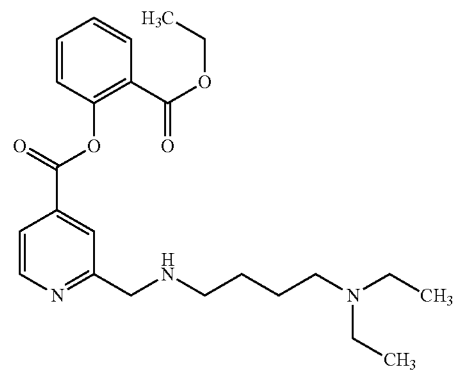 [SMILES: CCOC(=O)c1ccccc1OC(=O)c1ccnc(CNCCCCN(CC)CC)c1] | 2-(ethoxycarbonyl)phenyl 2-({[4-(diethylamino)butyl]amino}methyl)pyridine-4-carboxylate | +++ |
| 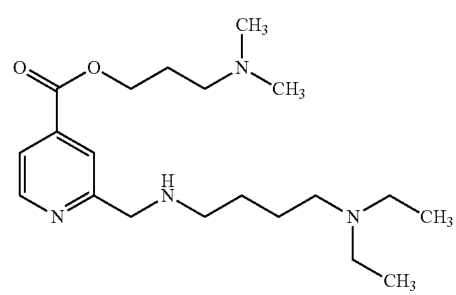 [SMILES: CCN(CC)CCCCNCc1cc(C(=O)OCCCN(C)C)ccn1] | 3-(dimethylamino)propyl 2-({[4-(diethylamino)butyl]amino}methyl)pyridine-4-carboxylate | ++ |
| 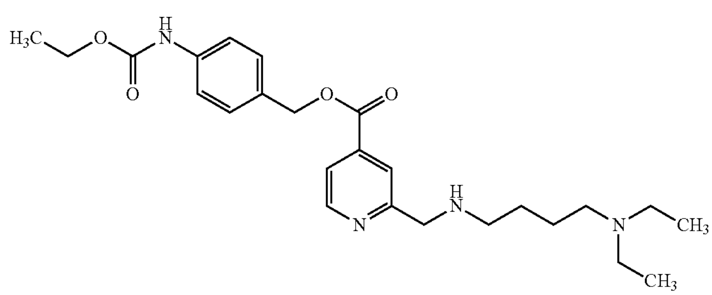 [SMILES: CCOC(=O)Nc1ccc(COC(=O)c2ccnc(CNCCCCN(CC)CC)c2)cc1] | {4-[(ethoxycarbonyl)amino]phenyl}methyl 2-({[4-(diethylamino)butyl]amino}methyl)pyridine-4-carboxylate | ++ |

TABLE 5-continued

| Structure | Name | EC50 |
|---|---|---|
| 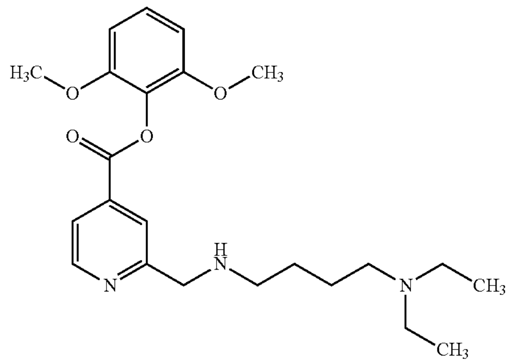 [SMILES: CCN(CC)CCCCNCc1cc(C(=O)Oc2c(OC)cccc2OC)ccn1] | 2,6-dimethoxyphenyl 2-({[4-(diethylamino)butyl]amino}methyl)pyridine-4-carboxylate | +++ |
| 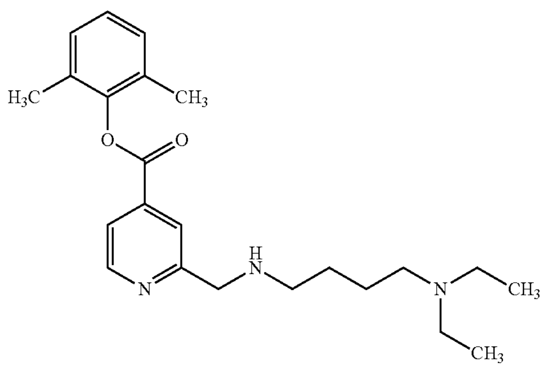 [SMILES: CCN(CC)CCCCNCc1cc(C(=O)Oc2c(C)cccc2C)ccn1] | 2,6-dimethylphenyl 2-({[4-(diethylamino)butyl]amino}methyl)pyridine-4-carboxylate | +++ |
| 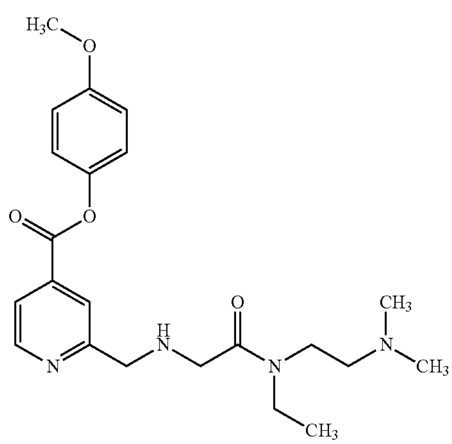 [SMILES: CCN(CCN(C)C)C(=O)CNCc1cc(C(=O)Oc2ccc(OC)cc2)ccn1] | 4-methoxyphenyl 2-{[({[2-(dimethylamino)ethyl](ethyl)carbamoyl}methyl)amino]methyl}pyridine-4-carboxylate | ++ |
| 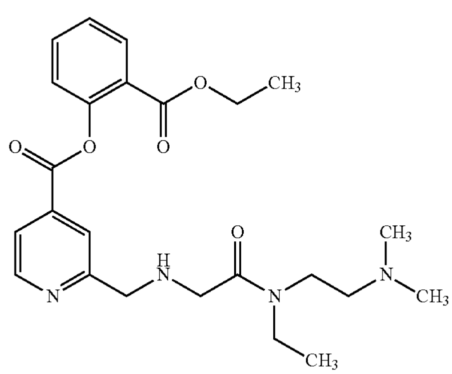 [SMILES: CCOC(=O)c1ccccc1OC(=O)c1ccnc(CNCC(=O)N(CC)CCN(C)C)c1] | 2-(ethoxycarbonyl)phenyl 2-{[({[2-(dimethylamino)ethyl](ethyl)carbamoyl}methyl)amino]methyl}pyridine-4-carboxylate | ++ |

TABLE 5-continued

| Structure | Name | EC50 |
|---|---|---|
| 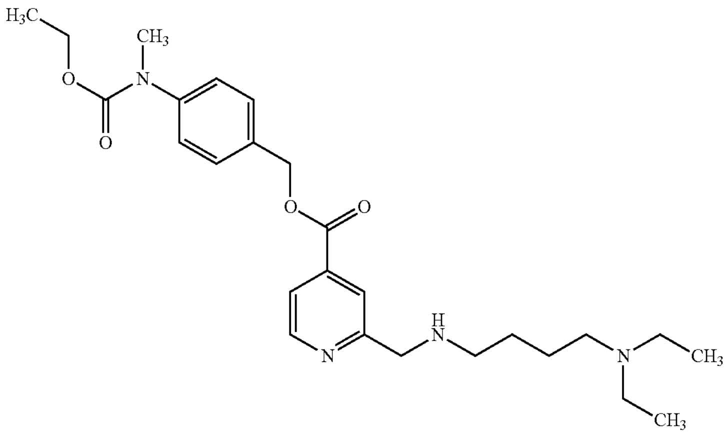 [SMILES: CCOC(=O)N(C)c1ccc(COC(=O)c2ccnc(CNCCCCN(CC)CC)c2)cc1] | {4-[(ethoxycarbonyl)(methyl)amino]phenyl}methyl 2-({[4-(diethylamino)butyl]amino}methyl)pyridine-4-carboxylate | +++ |
| 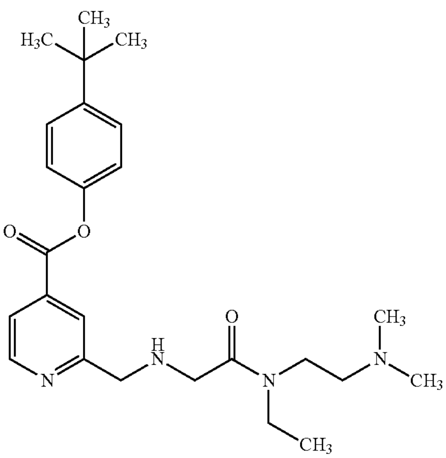 [SMILES: CCN(CCN(C)C)C(=O)CNCc1cc(C(=O)Oc2ccc(C(C)(C)C)cc2)ccn1] | 4-tert-butylphenyl 2-{[({[2-(dimethylamino)ethyl](ethyl)carbamoyl}methyl)amino]methyl}pyridine-4-carboxylate | +++ |
| 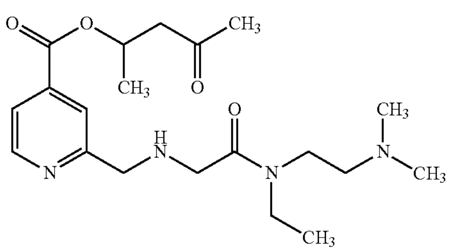 [SMILES: CCN(CCN(C)C)C(=O)CNCc1cc(C(=O)OC(C)CC(C)=O)ccn1] | 4-oxopentan-2-yl 2-{[({[2-(dimethylamino)ethyl](ethyl)carbamoyl}methyl)amino]methyl}pyridine-4-carboxylate | +++ |
| 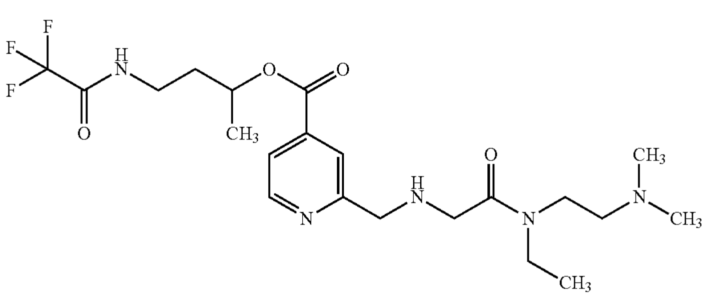 [SMILES: CCN(CCN(C)C)C(=O)CNCc1cc(C(=O)OC(C)CCNC(=O)C(F)(F)F)ccn1] | 4-(trifluoroacetamido)butan-2-yl 2-{[({[2-(dimethylamino)ethyl](ethyl)carbamoyl}methyl)amino]methyl}pyridine-4-carboxylate | +++ |

TABLE 5-continued

| Structure | Name | EC50 |
|---|---|---|
| 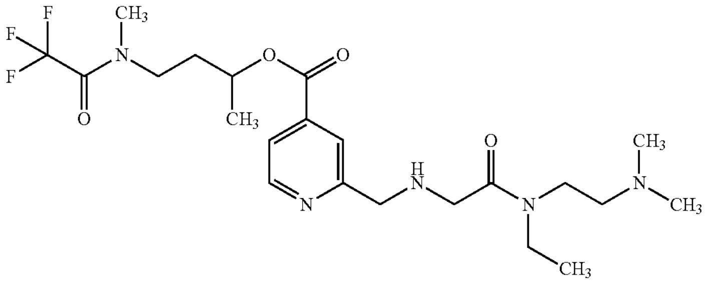 [SMILES: CCN(CCN(C)C)C(=O)CNCc1cc(C(=O)OC(C)CCN(C)C(=O)C(F)(F)F)ccn1] | 4-(2,2,2-trifluoro-N-methylacetamido)butn-2-yl 2-{[({[2-(dimethylamino)ethyl](ethyl)carbamoyl}methyl)amino]methyl}pyridine-4-carboxylate | +++ |
| 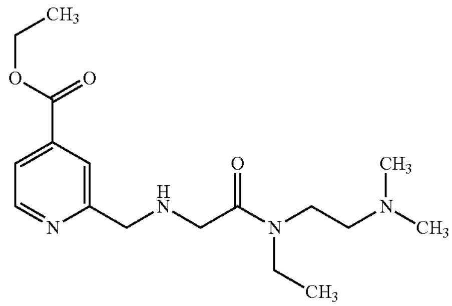 [SMILES: CCOC(=O)c1ccnc(CNCC(=O)N(CC)CCN(C)C)c1] | ethyl 2-{[({[2-(dimethylamino)ethyl](ethyl)carbamoyl}methyl)amino]methyl}pyridine-4-carboxylate | +++ |
| 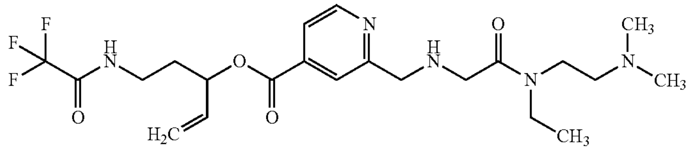 [SMILES: C=CC(CCNC(=O)C(F)(F)F)OC(=O)c1ccnc(CNCC(=O)N(CC)CCN(C)C)c1] | 5-(trifluoroacetamido)pent-1-en-3-yl 2-{[({[2-(dimethylamino)ethyl](ethyl)carbamoyl}methyl)amino]methyl}pyridine-4-carboxylate | +++ |
| 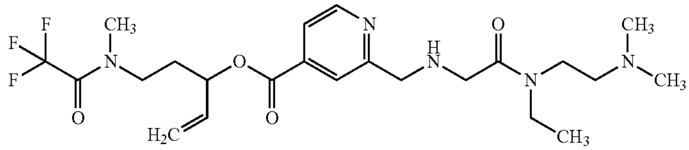 [SMILES: C=CC(CCN(C)C(=O)C(F)(F)F)OC(=O)c1ccnc(CNCC(=O)N(CC)CCN(C)C)c1] | 5-(2,2,2-trifluoro-N-methylacetamido)pent-1-en-3-yl 2-{[({[2-(dimethylamino)ethyl](ethyl)carbamoyl}methyl)amino]methyl}pyridine-4-carboxylate | +++ |
| 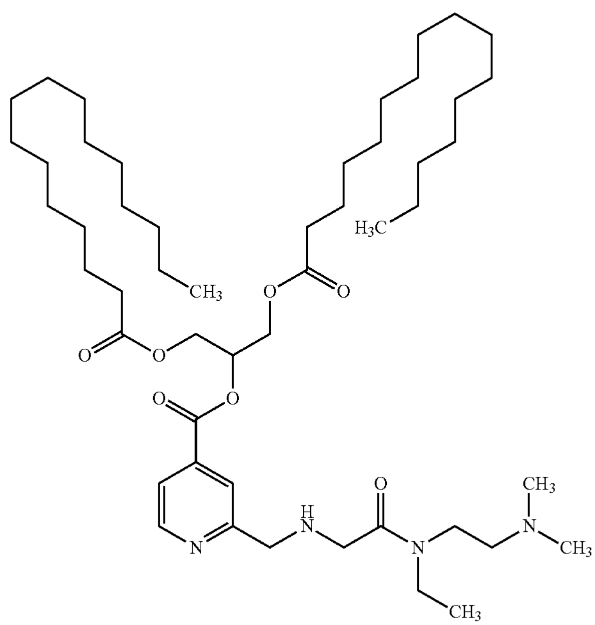 [SMILES: CCCCCCCCCCCCCCCC(=O)OCC(COC(=O)CCCCCCCCCCCCCCC)OC(=O)c1ccnc(CNCC(=O)N(CC)CCN(C)C)c1] | 2-(2-{[({[2-(dimethylamino)ethyl](ethyl)carbamoyl}methyl)amino]methyl}pyridine-4-carbonyloxy)-3-(hexadecanoyloxy)propyl hexadecanoate | +++ |

TABLE 5-continued

| Structure | Name | EC50 |
|---|---|---|
| 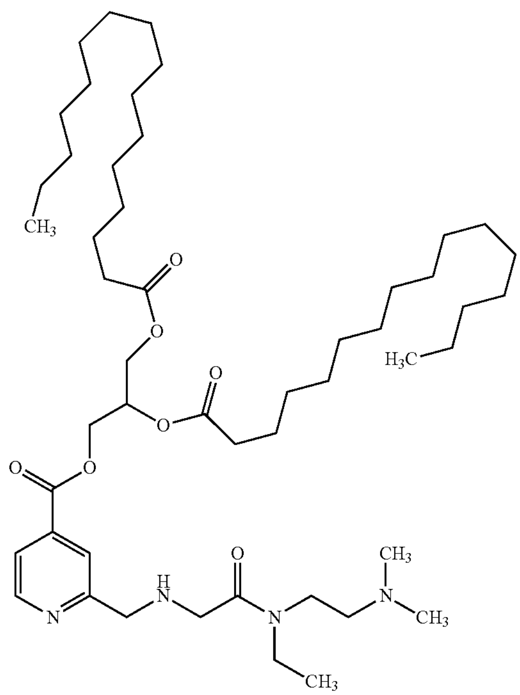 [SMILES: CCCCCCCCCCCCCCCC(=O)OCC(COC(=O)c1ccnc(CNCC(=O)N(CC)CCN(C)C)c1)OC(=O)CCCCCCCCCCCCCCC] | 1-(2-{[({[2-(dimethylamino)ethyl](ethyl)carbamoyl}methyl)amino]methyl}pyridine-4-carbonyloxy)-3-(hexadecanoyloxy)propan-2-yl hexadecanoate | +++ |
| 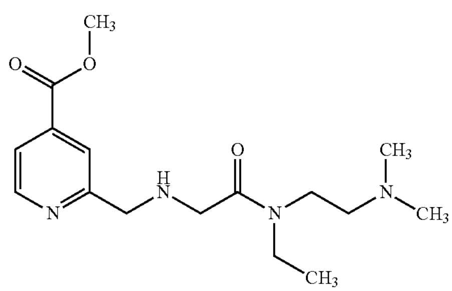 [SMILES: CCN(CCN(C)C)C(=O)CNCc1cc(C(=O)OC)ccn1] | methyl 2-{[({[2-(dimethylamino)ethyl](ethyl)carbamoyl}methyl)amino]methyl}pyridine-4-carboxylate | +++ |
| 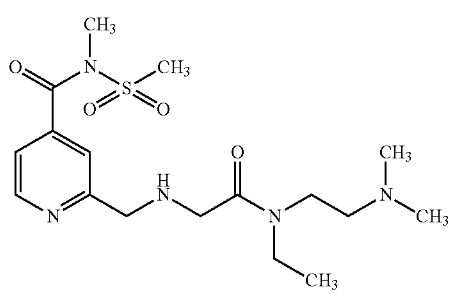 [SMILES: CCN(CCN(C)C)C(=O)CNCc1cc(C(=O)N(C)S(C)(=O)=O)ccn1] | 2-{[({[2-(dimethylamino)ethyl](ethyl)carbamoyl}methyl)amino]methyl}-N-methanesulfonyl-N-methylpyridine-4-carboxamide | +++ |
| 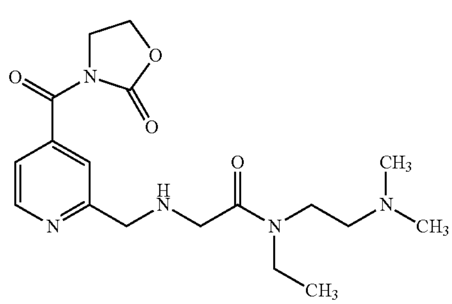 [SMILES: CCN(CCN(C)C)C(=O)CNCc1cc(C(=O)N2CCOC2=O)ccn1] | N-[2-(dimethylamino)ethyl]-N-ethyl-2-({[4-(2-oxo-1,3-oxazolidine-3-carbonyl)pyridin-2-yl]methyl}amino)acetamide | ++ |

TABLE 5-continued

| Structure | Name | EC50 |
|---|---|---|
| 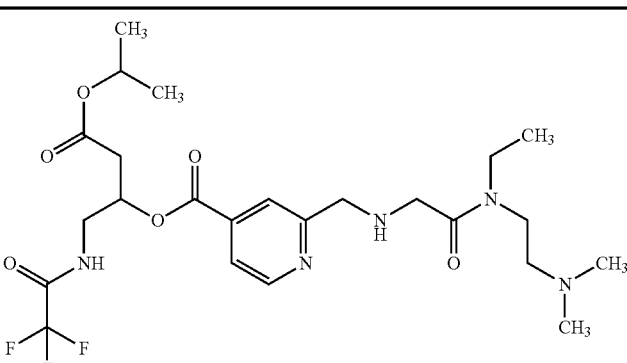 | propan-2-yl 3-(2-{[({[2-(dimethylamino)ethyl](ethyl)carbamoyl}methyl)amino]methyl}pyridine-4-carbonyloxy)-4-(trifluoroacetamido)butanoate | ++ |
| 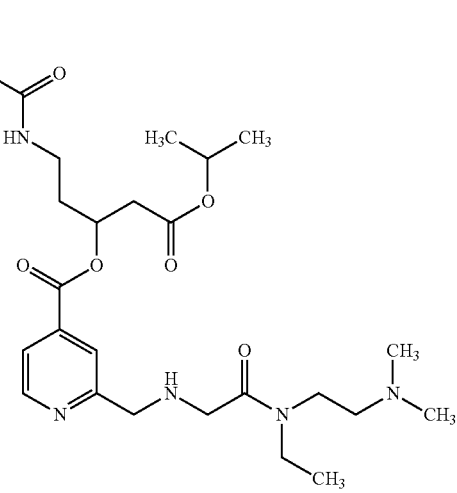 | propen-2-yl 3-(2-{[({[2-(dimethylamino)ethyl](ethyl)carbamoyl}methyl)amino]methyl}pyridine-4-carbonyloxy)-5-(trifluoroacetamido)pentanoate | ++ |
| 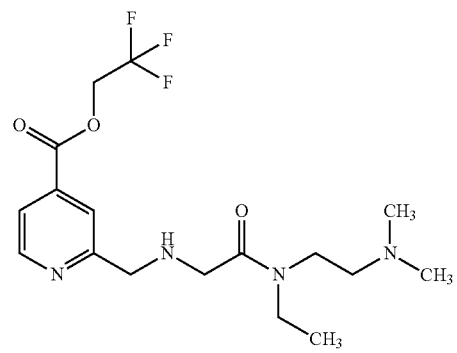 [SMILES: CCN(CCN(C)C)C(=O)CNCc1cc(C(=O)OCC(F)(F)F)ccn1] | 2,2,2-trifluoroethyl 2-{[({[2-(dimethylamino)ethyl](ethyl)carbamoyl}methyl)amino]methyl}pyridine-4-carboxylate | ++ |
| 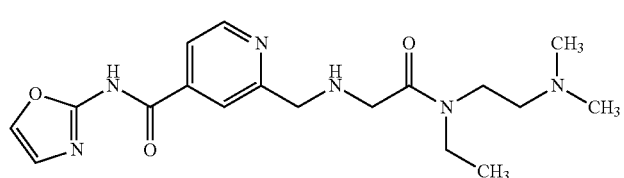 | 2-{[({[2-(dimethylamino)ethyl](ethyl)carbamoyl}methyl)amino]methyl}-N-(1,3-oxazol-2-yl)pyridine-4-carboxamide | ++ |
| 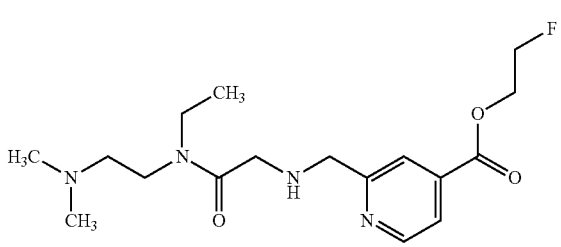 [SMILES: CCN(CCN(C)C)C(=O)CNCc1cc(C(=O)OCCF)ccn1] | 2-fluoroethyl 2-{[({[2-(dimethylamino)ethyl](ethyl)carbamoyl}methyl)amino]methyl}pyridine-4-carboxylate | +++ |

TABLE 5-continued

| Structure | Name | EC50 |
|---|---|---|
| 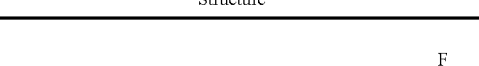 | 2,2-difluoroethyl 2-{[({[2-(dimethylamino)ethyl](ethyl)carbamoyl}methyl)amino]methyl}pyridine-4-carboxylate | +++ |

(a) +++: IC50 <1 μM; ++: 1 μM ≤ IC50 ≤ 50 μM; +: IC50 > 50 μM

Example 5: Histone Lysine Demethylase Immunofluorescence Assays for IC50 Value Determination in Cell This example demonstrates the ability of the compounds of the invention to inhibit demethylation of a specific H3 lysine in a human osteosarcoma cell line transfected to express a specific histone lysine demethylase.

General Method

U2OS cells were seeded 24 hours before transfection. Transfection was performed with Fugene HD transfection reagent as recommended by the manufacturer. 6 hours after transfection, the cells were harvested and seeded into multi well plates into media containing compound. The media used was DMEM containing 5% FBS and pen/strep. 20 hours after incubation of cells with compounds, the cells were washed once in PBS, harvested by fixation with formaldehyde 4% aqueous solution, and washed 2 times in PBS. Subsequently, the cells were permeabilized in PBS with 0.2% Triton X-100 for 10 min at room temperature. Blocking was performed in PBS with 0.2% Triton X-100 and 5% FBS for 45 min at room temperature. The cells were incubated with primary antibodies diluted 1 μg/ml in blocking solution over night at 4° C. The primary antibodies used in the assays were HA.11 (Covance, MMS-101P) and the antibody detecting the mark specified in the Table 6 below.

After incubation with primary antibodies, the cells were washed 3 times with PBS, incubated with secondary antibodies diluted 1:1000 (Alexa fluor 594 goat anti rabbit IgG, Invitrogen, A11012; Alexa flour 488 donkey anti mouse IgG, Invitrogen, A21202) and Hoechst, 20 μg/ml (Sigma, 33342) in blocking solution, and washed again 3 times with PBS. Finally, PBS was added and high throughput imaging and analysis were performed by an IN Cell Analyzer 1000 (GE Healthcare). The robot software analyzed individual cells and divided these into HA+ (transfected cells) and HA− (non-transfected cells). The IC50 values in Table 7 below were based on an average measure of the staining of the mark specified in the Table 6 below in the transfected cells.

TABLE 6

| Construct name | Vendor/source | Sequence | Mark detected | Primary antibody used for detection of mark | Plasmid NCBI ID |
|---|---|---|---|---|---|
| pCMVHA JMJD2C | BRIC | Full length | H3K9me3 | Abcam Ab8898 | NM_014663 |
| pCMVHA JMJD2A | BRIC | Full length | H3K9me3 | Abcam Ab8898 | NM_015061 |
| pCMVHA PLU1 | BRIC | Fragment (1-752) | H3K4me2 | Millipore 07-030 | NM_006618 |

HDME Inhibition

TABLE 7

| Structure | Name | GASC1 (KDM4C) | JMJD2A (KDM4A) | PLU1 (KDM5B) |
|---|---|---|---|---|
| 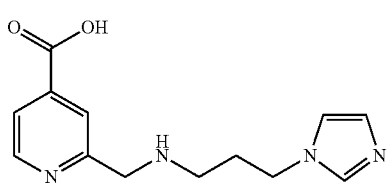 [SMILES: O=C(O)c1ccnc(CNCCCn2ccnc2)c1] | 2-({[3-(1H-imidazol-1-yl)propyl]amino}methyl)pyridine-4-carboxylic acid | + | | ++ |

TABLE 7-continued

| Structure | Name | GASC1 (KDM4C) | JMJD2A (KDM4A) | PLU1 (KDM5B) |
|---|---|---|---|---|
| 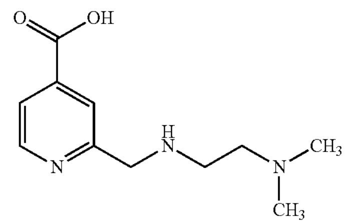 [SMILES: CN(C)CCNCc1cc(C(=O)O)ccn1] | 2-({[2-(dimethylamino)ethyl]amino}methyl)pyridine-4-carboxylic acid | ++ | | ++ |
| 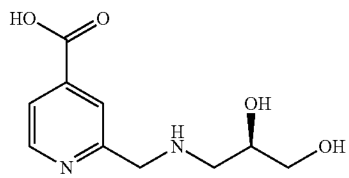 [SMILES: O=C(O)c1ccnc(CNC[C@@H](O)CO)c1] | 2-({[(2R)-2,3-dihydroxypropyl]amino}methyl)pyridine-4-carboxylic acid | + | | + |
| 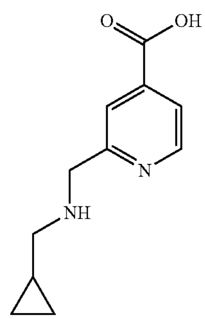 [SMILES: O=C(O)c1ccnc(CNCC2CC2)c1] | 2-{[(cyclopropylmethyl)amino]methyl}pyridine-4-carboxylic acid | + | | ++ |
| 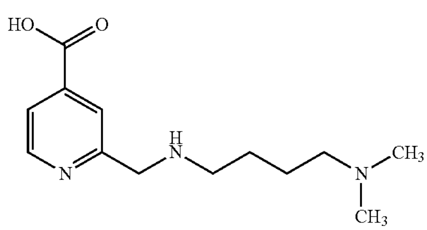 [SMILES: CN(C)CCCCNCc1cc(C(=O)O)ccn1] | 2-({[4-(dimethylamino)butyl]amino}methyl)pyridine-4-carboxylic acid | + | | ++ |
| 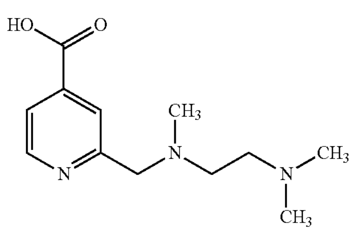 [SMILES: CN(C)CCN(C)Cc1cc(C(=O)O)ccn1] | 2-({[2-(dimethylamino)ethyl](methyl)amino}methyl)pyridine-4-carboxylic acid | + | | + |
| 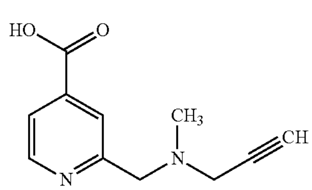 | 2-{[methyl(prop-2-yn-1-yl)amino]methyl}pyridine-4-carboxylic acid | + | | + |

TABLE 7-continued

| Structure | Name | GASC1 (KDM4C) | JMJD2A (KDM4A) | PLU1 (KDM5B) |
|---|---|---|---|---|
| 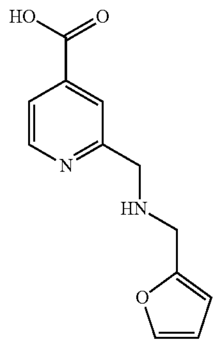 [SMILES: O=C(O)c1ccnc(CNCc2ccco2)c1] | 2-{[(furan-2-ylmethyl)amino]methyl}pyridine-4-carboxylic acid | ++ | ++ | ++ |
| 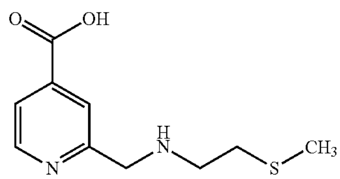 | 2-({[2-(methylsulfanyl)ethyl]amino}methyl)pyridine-4-carboxylic acid | | ++ | |
| 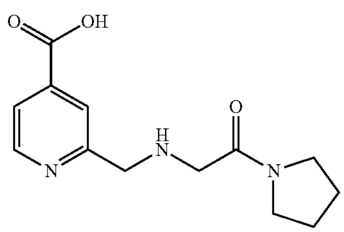 [SMILES: O=C(O)c1ccnc(CNCC(=O)N2CCCC2)c1] | 2-({[2-oxo-2-(pyrrolidin-1-yl)ethyl]amino}methyl)pyridine-4-carboxylic acid | ++ | | + |
| 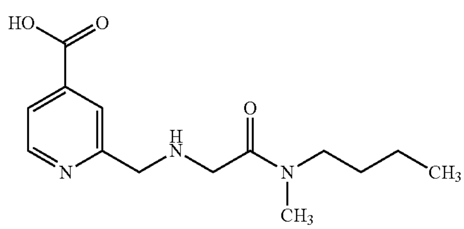 [SMILES: CCCCN(C)C(=O)CNCc1cc(C(=O)O)ccn1] | 2-[({[butyl(methyl)carbamoyl]methyl}amino)methyl]pyridine-4-carboxylic acid | ++ | | + |
| 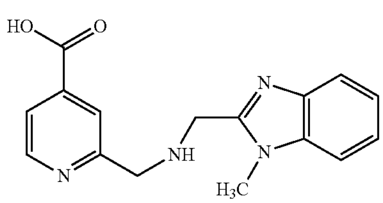 | 2-({[(1-methyl-1H-1,3-benzodiazol-2-yl)methyl]amino}methyl)pyridine-4-carboxylic acid | + | | ++ |
| 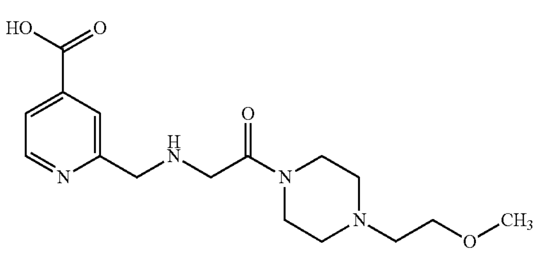 [SMILES: COCCN1CCN(C(=O)CNCc2cc(C(=O)O)ccn2)CC1] | 2-[({2-[4-(2-methoxyethyl)piperazin-1-yl]-2-oxoethyl}amino)methyl]pyridine-4-carboxylic acid | + | | + |

TABLE 7-continued

| Structure | Name | GASC1 (KDM4C) | JMJD2A (KDM4A) | PLU1 (KDM5B) |
|---|---|---|---|---|
| 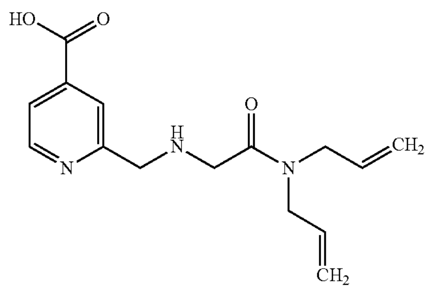 [SMILES: C=CCN(CC=C)C(=O)CNCc1cc(C(=O)O)ccn1] | 2-[({[bis(prop-2-en-1-yl)carbamoyl]methyl}amino)methyl]pyridine-4-carboxylic acid | ++ | | ++ |
| 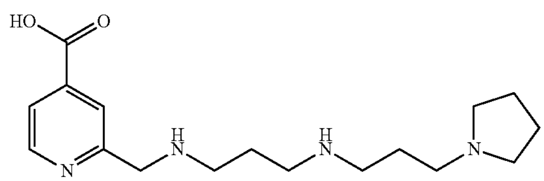 [SMILES: O=C(O)c1ccnc(CNCCCNCCCN2CCCC2)c1] | 2-{[(3-{[3-(pyrrolidin-1-yl)propyl]amino}propyl)amino]methyl}pyridine-4-carboxylic acid | + | | + |
| 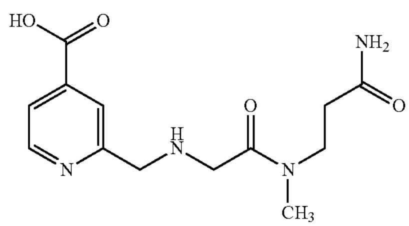 [SMILES: CN(CCC(N)=O)C(=O)CNCc1cc(C(=O)O)ccn1] | 2-[({[(2-carbamoylethyl)(methyl)carbamoyl]methyl}amino)methyl]pyridine-4-carboxylic acid | + | | |
| 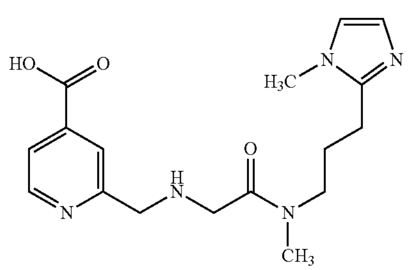 [SMILES: CN(CCCc1nccn1C)C(=O)CNCc1cc(C(=O)O)ccn1] | 2-{[({methyl[3-(1-methyl-1H-imidazol-2-yl)propyl]carbamoyl}methyl)amino]methyl}pyridine-4-carboxylic acid | ++ | | ++ |
| 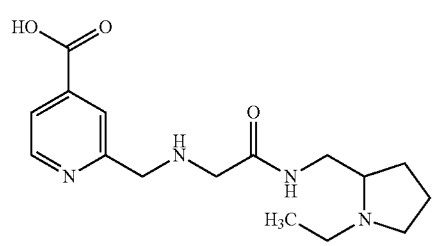 [SMILES: CCN1CCCC1CNC(=O)CNCc1cc(C(=O)O)ccn1] | 2-{[({[(1-ethylpyrrolidin-2-yl)methyl]carbamoyl}methyl)amino]methyl}pyridine-4-carboxylic acid | + | | ++ |
| 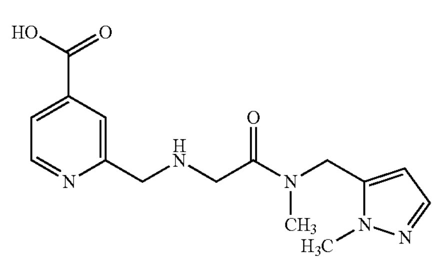 [SMILES: CN(Cc1ccnn1C)C(=O)CNCc1cc(C(=O)O)ccn1] | 2-{[({methyl[(1-methyl-1H-pyrazol-5-yl)methyl]carbamoyl}methyl)amino]methyl}pyridine-4-carboxylic acid | + | | + |

TABLE 7-continued

| Structure | Name | GASC1 (KDM4C) | JMJD2A (KDM4A) | PLU1 (KDM5B) |
|---|---|---|---|---|
| 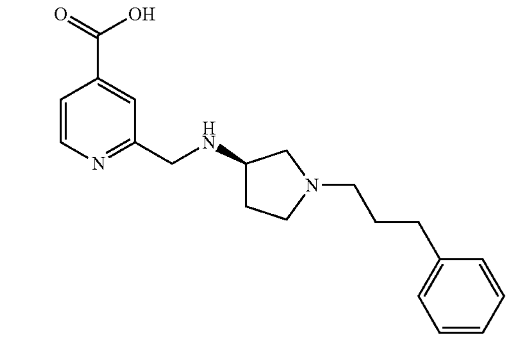 [SMILES: O=C(O)c1ccnc(CN[C@@H]2CCN(CCCc3ccccc3)C2)c1] | 2-({[(3R)-1-(3-phenylpropyl) pyrrolidin-3-yl]amino}methyl)pyridine-4-carboxylic acid | + | | ++ |
| 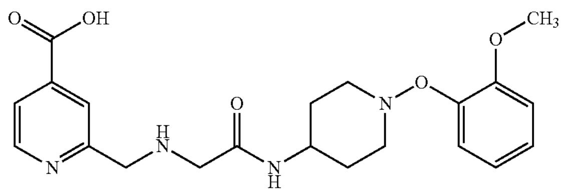 [SMILES: COc1ccccc1ON1CCC(NC(=O)CNCc2cc(C(=O)O)ccn2)CC1] | 2-({[({1-[(2-methoxyphenyl) methyl]piperidin-4-yl}carbamoyl)methyl]amino} methyl)pyridine-4-carboxylic acid | | | ++ |
| 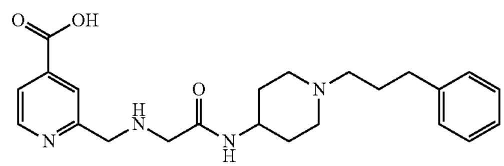 [SMILES: O=C(CNCc1cc(C(=O)O)ccn1)NC1CCN(CCCc2ccccc2)CC1] | 2-{[({[1-(3-phenylpropyl) piperidin-4-yl]carbamoyl}methyl)amino] methyl}pyridine-4-carboxylic acid | + | | + |
| 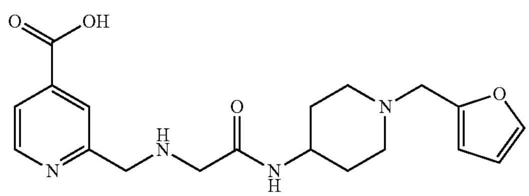 [SMILES: O=C(CNCc1cc(C(=O)O)ccn1)NC1CCN(Cc2ccco2)CC1] | 2-{[({[1-(furan-2-ylmethyl)piperidin-4-yl]carbamoyl}methyl)amino] methyl}pyridine-4-carboxylic acid | + | | + |
| 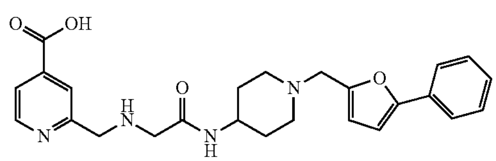 [SMILES: O=C(CNCc1cc(C(=O)O)ccn1)NC1CCN(Cc2ccc(-c3ccccc3)o2)CC1] | 2-({[({1-[(5-phenylfuran-2-yl)methyl]piperidin-4-yl}carbamoyl)methyl]amino} methyl)pyridine-4-carboxylic acid | + | | + |
| 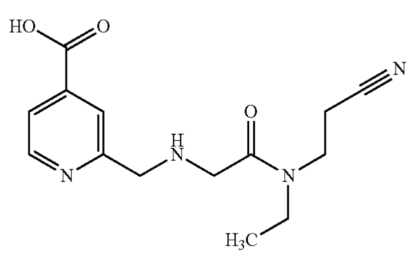 [SMILES: CCN(CCC#N)C(=O)CNCc1cc(C(=O)O)ccn1] | 2-[({[(2-cyanoethyl)(ethyl)carbamoyl] methyl}amino)methyl] pyridine-4-carboxylic acid | | | ++ |
| 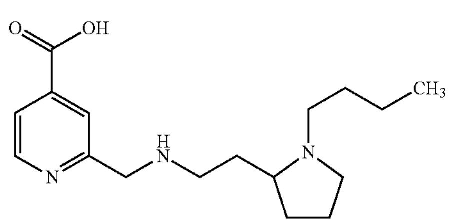 [SMILES: CCCCN1CCCC1CCNCc1cc(C(=O)O)ccn1] | 2-({[2-(1-butylpyrrolidin-2-yl)ethyl]amino}methyl) pyridine-4-carboxylic acid | | | ++ |

TABLE 7-continued

| Structure | Name | GASC1 (KDM4C) | JMJD2A (KDM4A) | PLU1 (KDM5B) |
|---|---|---|---|---|
| 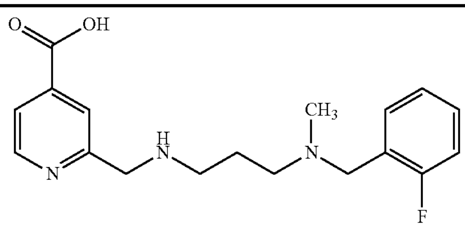 | 2-{[(3-{[(2-fluorophenyl)methyl](methyl)amino}propyl)amino]methyl}pyridine-4-carboxylic acid | + | | ++ |
| 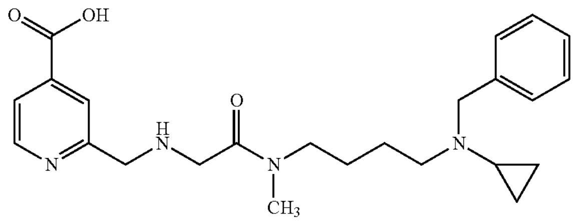 [SMILES: CN(CCCCN(Cc1ccccc1)C1CC1)C(=O)CNCc1cc(C(=O)O)ccn1] | 2-({[({4-benzyl(cyclopropyl)amino]butyl}(methyl)carbamoyl)methyl]amino}methyl)pyridine-4-carboxylic acid | | | + |
| 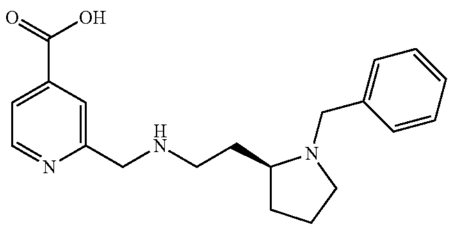 [SMILES: O=C(O)c1ccnc(CNCC[C@@H]2CCCN2Cc2ccccc2)c1] | 2-[({2-[(2S)-1-benzylpyrrolidin-2-yl]ethyl}amino)methyl]pyridine-4-carboxylic acid | + | | ++ |
| 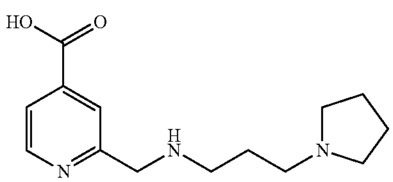 [SMILES: O=C(O)c1ccnc(CNCCCN2CCCC2)c1] | 2-({[3-(pyrrolidin-1-yl)propyl]amino}methyl)pyridine-4-carboxylic acid | ++ | | ++ |
| 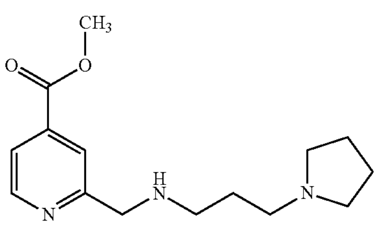 [SMILES: COC(=O)c1ccnc(CNCCCN2CCCC2)c1] | methyl 2-({[3-(pyrrolidin-1-yl)propyl]amino}methyl)pyridine-4-carboxylate | ++ | | ++ |
| 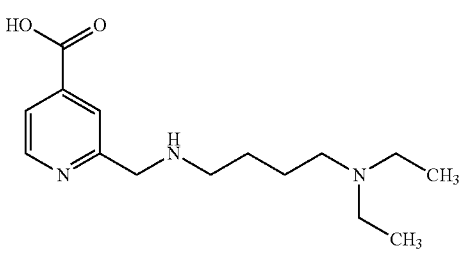 [SMILES: CCN(CC)CCCCNCc1cc(C(=O)O)ccn1] | 2-({[4-(diethylamino)butyl]amino}methyl)pyridine-4-carboxylic acid | ++ | | ++ |
| | 2-{[({2-(dimethylamino)ethyl](ethyl)carbamoyl}methyl)amino]methyl}pyridine-4-carboxylic acid | + | ++ | ++ |

TABLE 7-continued

| Structure | Name | GASC1 (KDM4C) | JMJD2A (KDM4A) | PLU1 (KDM5B) |
|---|---|---|---|---|
| 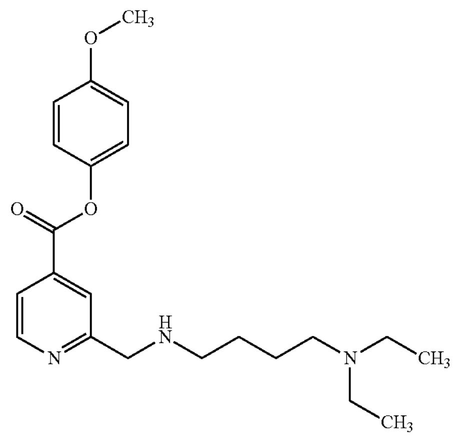 [SMILES: CCN(CC)CCCCNCc1cc(C(=O)Oc2ccc(OC)cc2)ccn1] | 4-methoxyphenyl 2-({[4-(diethylamino)butyl]amino}methyl)pyridine-4-carboxylate | ++ | | +++ |
| 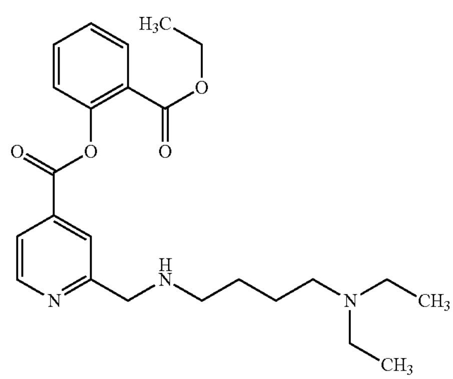 [SMILES: CCOC(=O)c1ccccc1OC(=O)c1ccnc(CNCCCCN(CC)CC)c1] | 2-(ethoxycarbonyl)phenyl 2-({[4-(diethylamino)butyl]amino}methyl)pyridine-4-carboxylate | ++ | | +++ |
| 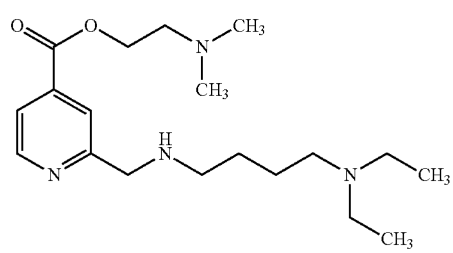 [SMILES: CCN(CC)CCCCNCc1cc(C(=O)OCCN(C)C)ccn1] | 2-(dimethylamino)ethyl 2-({[4-(diethylamino)butyl]amino}methyl)pyridine-4-carboxylate | ++ | | ++ |
| 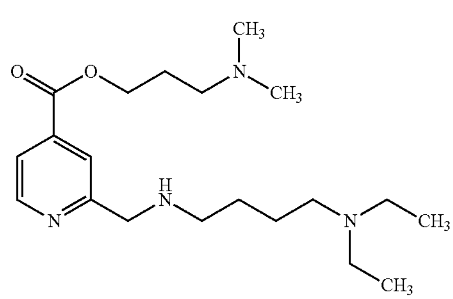 [SMILES: CCN(CC)CCCCNCc1cc(C(=O)OCCCN(C)C)ccn1] | 3-(dimethylamino)propyl 2-({[4-(diethylamino)butyl]amino}methyl)pyridine-4-carboxylate | ++ | | ++ |

TABLE 7-continued

| Structure | Name | GASC1 (KDM4C) | JMJD2A (KDM4A) | PLU1 (KDM5B) |
|---|---|---|---|---|
| [structure] | {4-[(ethoxycarbonyl)(methyl)amino]phenyl}methyl 2-({[4-(diethylamino)butyl]amino}methyl)pyridine-4-carboxylate | +++ | | |
| [structure] | 2-(2-{[({[2-(dimethylamino)ethyl](ethyl)carbamoyl}methyl)amino]methyl}pyridine-4-carbonyloxy)-3-(hexadecanoyloxy)propyl hexadecanoate | ++ | | |

(a) + + + : IC50 < 1 μM;
++: 1 μM ≤ IC50 ≤ 50 μM;
+ : IC50 > 50 μM

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

LIST OF REFERENCES

Catchpole S et al., Int. J. Oncol. 38, 1267-77, 2011
Cloos, P. a. C. et al. (2008), Genes. Dev. 22; 115-1140
Cloos, P. Et al., Nature 442, 307-11, 2006
Fischle, W., et. Al., Curr. Opinion Cell Biol. 15, 172-83, 2003
Hayami S. et al. (2010) Mol. Cancer 9
He J et al., Blood 117 (14), 3869-80, 2011
He J et al. Nat Struct Mol Biol 15(11), 2008
Kelly, T. K. et al. (2010), "Epigenetic modifications as therapeutic targets", Nat. Biotechnol. 28; 1069-1078
Klose, R. J. et al., Nature 442, 312-16, 2006
Liu, G. Et al., Oncogene 28, 4491-500, 2009
Margueron, R., et al., Curr. Opinion Genet. Dev. 15, 163-76, 2005
Morton and Houghton, "Establishment of human tumor xenografts in immunodeficient mice", Nature Protocols, 2 (2) 247-250, 2007
Pfau R et al., PNAS 105(6), 1907-12, 2008
Queguiner, G. and Pastour, P., Comptes Rendus des Séances de l'Académie des Sciences, Série C: Sciences Chimiques, 268(2) 182-5, 1969.
Quina, A. S. et al. (2006), "Chromatin structure and epigenetics", Biochem. Pharmacol. 72; 1563-1569
Roy et al. PerkinElmer Technical Note: AlphaLISA #12, April 2011
Tzatsos A et al., PNAS 106 (8), 2641-6, 2009
Yamane K. et al., Mol. Cell 25, 801-12, 2007
Xiang Y. et al. (2007) PNAS 104

The invention claimed is:
1. A method of inhibiting a histone demethylase (HDME), comprising contacting a cell with a compound of the general Formula (I)

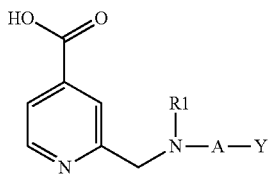

wherein
A is selected from —CHR$^2$C(O)— and C$_{1-8}$ alkylene, which alkylene may optionally be substituted with one or more R$^3$;
Y is selected from —H, —NR$^6$R$^7$, —OR$^7$, C$_{1-8}$ alkyl, C$_{2-8}$ alkenyl, C$_{2-8}$ alkynyl, C$_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R$^3$ and may form a cyclic structure with R$^2$;
R$^1$ is selected from —H and C$_{1-8}$ alkyl, which alkyl may be optionally substituted with one or more selected from —OH, aryl, C$_{1-6}$ alkoxy, heteroaryl, aryloxy, heteroaryloxy, F, and C$_{3-6}$ cycloalkyl;
R$^2$ is selected from —H, C$_{1-8}$ alkyl, C$_{2-8}$ alkenyl, C$_{2-8}$ alkynyl, and C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl, and may form a cyclic structure with Y;
each R$^3$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$;
Z is selected from a single bond, C$_{1-4}$ alkylene, heterocyclylene and C$_{3-6}$ cycloalkylene;
each R$^4$ is independently selected from C$_{1-6}$ alkyl, C$_{1-4}$ fluoroalkyl, C$_{1-4}$ hydroxyalkyl, C$_{1-4}$ alkoxy, C$_{3-10}$ cycloalkyl, —N(R$^1$)$_2$, carbamoyl, and —OH;
each R$^5$ is independently selected from C$_{1-6}$ alkyl, C$_{1-4}$ fluoroalkyl, C$_{1-4}$ hydroxyalkyl, C$_{1-4}$ alkoxy, C$_{3-6}$ cycloalkyl, —CN, —F, —Cl, —Br, carbamoyl and —OH;
each of R$^6$ and R$^7$ is independently selected from —H, C$_{1-8}$ alkyl, C$_{1-4}$ fluoroalkyl, C$_{1-4}$ perfluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected R$^8$; or, alternatively, R$^6$ and R$^7$ may together with the N-atom to which they are attached form an N-heterocyclic ring optionally substituted with one or more independently selected R$^8$;
each R$^8$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from C$_{1-4}$ alkyl, C$_{1-4}$ fluoroalkyl, C$_{1-4}$ hydroxyalkyl, C$_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more R$^4$ as defined above, and wherein any heteroaryl and any aryl may be further substituted with one or more R$^5$ as defined above, and
each R$^9$ is independently selected from —H, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-aryl, and —Z-heteroaryl, wherein any heterocyclyl may be substituted with one or more R$^4$ as defined above, and wherein any heteroaryl and any aryl may be substituted with one or more R$^5$ as defined above;
each of R$^{10}$ and R$^{11}$ is independently selected from —H, C$_{1-6}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, heterocyclyl, heteroaryl, and aryl, wherein any heterocyclyl may be substituted with one or more R$^4$ as defined above, and wherein any heteroaryl and any aryl may be substituted with one or more R$^5$ as defined above, or, alternatively, R$^{10}$ and R$^{11}$ may together with the N-atom to which they are attached form an N-heterocyclic ring optionally substituted with one or more R$^4$ as defined above;
with the proviso that Y is not H when A is —CH$_2$—;
in an amount effective to produce a concentration sufficient to inhibit the demethylation of a histone in the cell.
2. The method of claim 1, wherein Y is —NR$^6$R$^7$.
3. The method of claim 2, wherein A is —CHR$^2$C(O)—.
4. The method of claim 3, wherein A is —CH$_2$—C(O)—.
5. The method of claim 2, wherein Y is

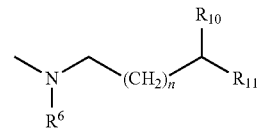

wherein n is from 1 to 3 and each of R$_{10}$ and R$_{11}$ independently is as defined in claim 1.
6. The method of claim 5, wherein Y is

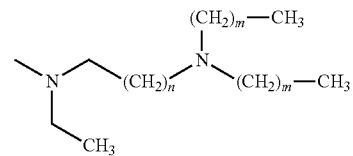

wherein n is from 1 to 3 and each m independently is from 0 to 2.
7. The method of claim 1, wherein Y is selected from heterocyclyl, heteroaryl and aryl, which may be optionally substituted with one or more R$^3$.
8. The method of claim 1, wherein the compound of Formula (I) has a molecular weight of 130-1,000 g/mol, such as 180-800 g/mol, e.g. 225-600 g/mol or 250-500 g/mol.

9. The method of claim 1, wherein the moiety -A-Y includes 1-3 cyclic moieties selected from monocyclic cycloalkyl, monocyclic heterocyclyl, monocyclic heteroaryl, dicyclic heteroaryl and monocyclic aryl.

10. The method of claim 1, wherein $R^1$ is selected from —H and $C_{1-4}$ alkyl.

11. The method of claim 1, wherein the HDME is a member of the KDM5 family.

12. A method of treating a HDME dependent disease in a subject, comprising administering to said subject a pharmaceutical composition comprising a compound of the general Formula (I)

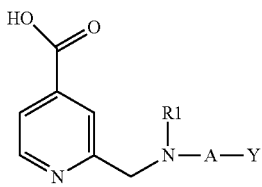

wherein

A is selected from —CHR$^2$C(O)— and $C_{1-8}$ alkylene, which alkylene may optionally be substituted with one or more $R^3$;

Y is selected from —H, —NR$^6$R$^7$, —OR$^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$ and may form a cyclic structure with $R^2$;

$R^1$ is selected from —H and $C_{1-8}$ alkyl, which alkyl may be optionally substituted with one or more selected from —OH, aryl, $C_{1-6}$ alkoxy, heteroaryl, aryloxy, heteroaryloxy, F, and $C_{3-6}$ cycloalkyl;

$R^2$ is selected from —H, $C_{1-8}$ alkyl, $C_{2-8}$ alkenyl, $C_{2-8}$ alkynyl, and $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl, and may form a cyclic structure with Y;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N(R$^1$)$_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

with the proviso that Y is not H when A is —CH$_2$—;

or a pharmaceutically acceptable salt thereof, and optionally one or more pharmaceutically acceptable excipients, diluents or carriers, wherein the HDME dependent disease is a cancer.

13. The method of claim 12, wherein said pharmaceutical composition comprises one or more further active substances.

* * * * *